(12) United States Patent
Bartels et al.

(10) Patent No.: US 9,920,072 B2
(45) Date of Patent: Mar. 20, 2018

(54) BACE1 INHIBITORS

(71) Applicant: Hoffmann-La Roche Inc., Little Falls, NJ (US)

(72) Inventors: Bjoern Bartels, Schopfheim (DE); Cosimo Dolente, Allschwil (CH); Wolfgang Guba, Muellheim (DE); Wolfgang Haap, Loerrach (DE); Ulrike Obst Sander, Reinach BL (CH); Jens-Uwe Peters, Grenzach-Wyhlen (DE); Mark Rogers-Evans, Bottmingen (CH); Didier Rombach, Mulhouse (FR); Thomas Woltering, Freiburg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/522,877

(22) PCT Filed: Oct. 30, 2015

(86) PCT No.: PCT/EP2015/075196
§ 371 (c)(1),
(2) Date: Apr. 28, 2017

(87) PCT Pub. No.: WO2016/071211
PCT Pub. Date: May 12, 2016

(65) Prior Publication Data
US 2017/0334930 A1   Nov. 23, 2017

(30) Foreign Application Priority Data
Nov. 3, 2014  (EP) ..................... 14191420

(51) Int. Cl.
*C07D 513/04*   (2006.01)

(52) U.S. Cl.
CPC ................. *C07D 513/04* (2013.01)

(58) Field of Classification Search
CPC ...................................... C07D 513/04
USPC ......................................... 544/48
See application file for complete search history.

(56) References Cited

FOREIGN PATENT DOCUMENTS

| WO | 2013174781 A1 | 11/2013 |
|---|---|---|
| WO | 2014150331 A1 | 9/2014 |
| WO | 2014150340 A1 | 9/2014 |

OTHER PUBLICATIONS

The International Search Report and Written Opinion, dated Dec. 8, 2015, in the related PCT Application No. PCT/EP2015/075196.

*Primary Examiner* — Kahsay Habte

(57) ABSTRACT

The present invention provides a compound of formula (I), having BACE1 inhibitory activity, their manufacture, pharmaceutical compositions containing them and their use as therapeutically active substances. The active compounds of the present invention are useful in the therapeutic and/or prophylactic treatment of e.g. Alzheimer's disease.

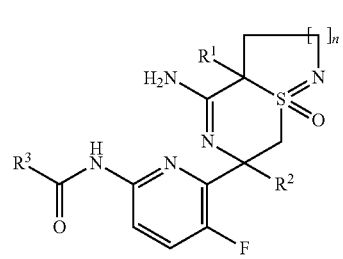

13 Claims, No Drawings

BACE1 INHIBITORS

CROSS-REFERENCE TO RELATED APPLICATIONS

This application is a National Stage Application of PCT/EP2015/075196 filed Oct. 30, 2015, which claims priority from European Patent Application No. 14191420.0, filed on Nov. 3, 2014. The priority of both said PCT and European Patent Application are claimed. Each of prior mentioned applications is hereby incorporated by reference herein in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994;10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat Neurosci*. 2001 March; 4(3):231-2, Roberds et al., BACE knockout mice are healthy despite lacking the primary beta-secretase activity in brain: implications for Alzheimer's disease therapeutics, *Hum Mol Genet*. 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol Chem*. 2007Sep. 7; 282(36):26326). It is thus presumed that inhibitors of BACE1 activity can be useful agents for therapeutic intervention in Alzheimer's disease (AD). Several patent applications have been filed describing BACE 1 inhibitors of various structures, e.g. WO2009103626, WO2010128058, WO2011020806, WO2011029803, WO2011069934, WO2011070029, WO2011138293, WO2012019966, WO2012028563, WO2012098064, WO2012104263, WO2012107371, WO2012110459, WO2012119883, WO2012126791, WO2012136603, WO2012139993, WO2012156284, WO2012163790, WO2012168164, WO2012168175, WO2013004676, WO2013041499, WO2013110622, WO2013174781, WO2014001228, WO2014114532, WO2014150331, WO2014150340 and WO2014150344.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, medicaments based on a compound in accordance with the invention and their production as well as the use of compounds of formula I in the control or prevention of illnesses such as Alzheimer's disease.

FIELD OF THE INVENTION

The present invention provides substituted [1,4]thiazino[2,1-g][1,2]thiazepines having BACE1 inhibitory properties, their manufacture, pharmaceutical compositions containing them and their use as therapeutically active substances.

SUMMARY OF THE INVENTION

The present invention provides a compound of formula I,

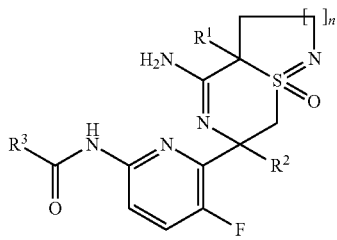

wherein the substituents and variables are as described below and in the claims, or a pharmaceutically acceptable salt thereof.

The present compounds have Asp2 (β-secretase, BACE1 or Memapsin-2) inhibitory activity and may therefore be used in the therapeutic and/or prophylactic treatment of diseases and disorders characterized by elevated β-amyloid levels and/or β-amyloid oligomers and/or β-amyloid plaques and further deposits, particularly Alzheimer's disease.

DETAILED DESCRIPTION OF THE INVENTION

The present invention provides a compound of formula I and their pharmaceutically acceptable salts thereof, the preparation of the above mentioned compounds, medicaments containing them and their manufacture as well as the use of the above mentioned compounds in the therapeutic and/or prophylactic treatment of diseases and disorders which are associated with inhibition of BACE1, such as Alzheimer's disease. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which may be linear or branched, with single or multiple branching, wherein the alkyl group in general comprises 1 to 6 carbon atoms, for example, methyl (Me), ethyl (Et), propyl, isopropyl (i-propyl), n-butyl, i-butyl (isobutyl), 2-butyl (sec-butyl), t-butyl (cert-butyl), isopentyl, 2-ethyl-propyl (2-methyl-propyl), 1,2-dimethyl-propyl and the like. Particular "$C_{1-6}$-alkyl" are "$C_{1-3}$-alkyl". Specific groups are methyl and ethyl. Most specific group is methyl.

The term "halogen-$C_{1-6}$-alkyl" or "$C_{1-6}$-alkyl-halogen", alone or in combination with other groups, refers to $C_{1-6}$-alkyl as defined herein, which is substituted by one or multiple halogen, particularly 1-5 halogen, more particularly 1-3 halogen. Particular halogen is fluoro. Particular "halogen-$C_{1-6}$-alkyl" is fluoro-$C_{1-6}$-alkyl and a particular "halogen-$C_{1-3}$-alkyl" is fluoro-$C_{1-3}$-alkyl. Examples are trifluoromethyl, difluoromethyl, fluoromethyl and the like. A specific group is fluoromethyl.

The term "cyano", alone or in combination with other groups, refers to N≡C—(NC—).

The term "halogen", alone or in combination with other groups, denotes chloro (Cl), iodo (I), fluoro (F) and bromo (Br). Particular "halogen" are Cl, I and F. A specific group is F.

The term "heteroaryl", alone or in combination with other groups, refers to an aromatic carbocyclic group of having a single 4 to 8 membered ring, in particular 5 to 8, or multiple condensed rings comprising 6 to 14, in particular 6 to 10 ring atoms and containing 1, 2 or 3 heteroatoms individually selected from N, O and S, in particular 1N or 2N, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl (pyridyl), pyrimidinyl (pyrimidyl), pyrrolyl, quinolinyl, tetrazolyl, thiazolyl, thienyl, triazolyl, 6,7-dihydro-5H-[1]pyrindinyl and the like. A particular "heteroaryl" group is pyridinyl.

The term "aryl" denotes a monovalent aromatic carbocyclic mono- or bicyclic ring system comprising 6 to 10 carbon ring atoms. Examples of aryl moieties include phenyl and naphthyl. Particular "aryl" is phenyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid (sulphuric acid), tartaric acid, trifluoroacetic acid and the like. Particular acids are formic acid, trifluoroacetic acid and hydrochloric acid. A specific acid is trifluoroacetic acid.

The term "amino", alone or in combination with other groups, refers to —NH$_2$.

The terms "hydroxyl" or "hydroxy", alone or in combination with other groups, refer to —OH.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein, in particular 1 $C_{2-6}$-alkynyl.

The term "$C_{2-6}$-alkynyl", alone or in combination with other groups, denotes a monovalent linear or branched saturated hydrocarbon group of 2 to 6 carbon atoms, in particular from 2 to 4 carbon atoms, and comprising one, two or three triple bonds. Examples of $C_{2-6}$-alkynyl include ethynyl, propynyl, and n-butynyl.

The term "$C_{1-6}$-alkoxy-$C_{1-6}$-alkyl", alone or in combination with other groups, refers to $C_{1-6}$-alkyl as defined herein, which is substituted by one or multiple $C_{1-6}$-alkoxy, as defined herein, particularly 1 $C_{1-6}$-alkoxy. Particular "$C_{1-6}$-alkoxy-$C_{1-6}$-alkyl" is methoxy-$C_{1-6}$-alkyl. Examples are methoxymethyl, methoxyethyl and the like.

The term "$C_{3-6}$-cycloalkyl" refers to a 3 to 8 membered carbon ring, for example cyclopropyl, cyclobutyl, cyclopentyl, cyclohexyl, cycloheptyl or cyclooctyl. Particular are cycloalkyl groups having a 3, 4, 5 or 6 membered carbon ring. Specific is cyclopropyl.

The term "$C_{1-6}$-alkoxy", alone or in combination with other groups, stands for an —O—$C_{1-6}$-alkyl radical which may be linear or branched, with single or multiple branching, wherein the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" are groups with 1 to 4 carbon atoms. Specific are ethoxy and methoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy. Specific "halogen-$C_{1-6}$-alkoxy" are $CHF_2$—$CF_2$—$CH_2$—O—, $CHF_2$—O— and $CF_2$—O—.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Particularly it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (-log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (-log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as particularly, more particularly and most particularly definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught and A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure as pure stereoisomers as well as mixtures thereof.

The invention also provides pharmaceutical compositions, methods of using, and methods of preparing the aforementioned compounds.

All separate embodiments may be combined.

One embodiment of the invention provides a compound of formula I,

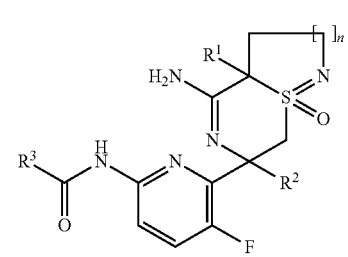

wherein
n is 2 or 3;
$R^1$ is selected from the group consisting of
  i) H,
  ii) halogen,
  iii) $C_{1-6}$-alkyl, and
  iv) halogen-$C_{1-6}$-alkyl;
$R^2$ is selected from the group consisting of
  i) H,
  ii) halogen,
  iii) $C_{1-6}$-alkyl, and
  iv) halogen-$C_{1-6}$-alkyl;
$R^3$ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;

iii) heteroaryl, and iv) heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;

or pharmaceutically acceptable salts thereof.

A certain embodiment of the invention provides a compound of formula I as described herein, wherein $R^1$ is $C_{1-6}$-alkyl.

A certain embodiment of the invention provides a compound of formula I as described herein, wherein $R^1$ is methyl.

A certain embodiment of the invention provides a compound of formula I as described herein, wherein $R^2$ is $C_{1-6}$-alkyl or halogen-$C_{1-6}$-alkyl.

A certain embodiment of the invention provides a compound of formula I as described herein, wherein $R^2$ is methyl or $CH_2F$.

A certain embodiment of the invention provides a compound of formula I as described herein, wherein $R^2$ is $C_{1-6}$-alkyl.

A certain embodiment of the invention provides a compound of formula I as described herein, wherein $R^2$ is methyl.

A certain embodiment of the invention provides a compound of formula I as described herein, wherein $R^3$ is heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy.

A certain embodiment of the invention provides a compound of formula I as described herein, wherein $R^3$ is heteroaryl substituted by cyano and $C_{1-6}$-alkyl.

A certain embodiment of the invention provides a compound of formula I as described herein, wherein $R^3$ is pyridinyl substituted by cyano and methyl.

A certain embodiment of the invention provides a compound of formula I as described herein, which is of formula Ia, wherein n, $R^1$ and $R^2$ are as described in claim 1 and $R^4$ is individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy

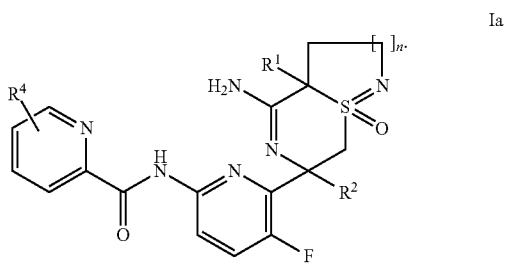

A certain embodiment of the invention provides a compound of formula I as described herein that is selected from the group consisting of N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-cyano-3-methylpyridine-2-carboxamide, N-[6-(6-amino-5a,8-dimethyl-10-oxido-3,4,5,5a,8,9-hexahydro-2H-1M$^4$41,4]thiazino[2,1-g][1,2]thiazepin-8-yl)-5-fluoropyridin-2-yl]-5-cyano-3-methylpyridine-2-carboxamide, N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-methoxypyrazine-2-carboxamide, N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-3,5-dichloropyridine-2-carboxamide, N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-fluoro-3-methylpyridine-2-carboxamide, N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-3-chloro-5-cyanopyridine-2-carboxamide, N-[6-(5-amino-4a,7-dimethyl-9-oxido-2,3,4,4a,7,8-hexahydro-9$\lambda^4$- [1,4]thiazino[2,1-f][1,2]thiazin-7-yl)-5-fluoropyridin-2-yl]-5-(difluoromethoxy)pyridine-2-carboxamide, N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-(2,2-difluoroethoxy)pyridine-2-carboxamide, N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-(2,2,3,3-tetrafluoropropoxy)pyridine-2-carboxamide, N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-5-methoxypyrazine-2-carboxamide, N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-3,5-dichloropyridine-2-carboxamide, N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-5-fluoro-3-methylpyridine-2-carboxamide, N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-3-chloro-5-cyanopyridine-2-carboxamide, N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-(difluoromethoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-(2,2-difluoroethoxy)pyridine-2-carboxamide, and N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-(2,2,3,3-tetrafluoropropoxy)pyridine-2-carboxamide, or pharmaceutically acceptable salts thereof.

A certain embodiment of the invention provides a compound of formula I as described herein that is selected from the group consisting of N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-methoxypyrazine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-3,5-dichloropyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-fluoro-3-methylpyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-(difluoromethoxy)pyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-(2,2-difluoroethoxy)pyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-(2,2,3,3-tetrafluoropropoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-cyano-3-methylpyridine-2-carboxamide (stereoisomer A), N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-cyano-3-methylpyridine-2-carboxamide (stereoisomer B), N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-cyano-3-methylpyridine-2-carboxamide (stereoisomer D), N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-methoxypyrazine-2-carboxamide, N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-3,5-dichloropyridine-2-carboxamide, N-[6-(6-amino-5a,8-dimethyl-10-oxido-3,4,5,5a,8,9-hexahydro-2H-10λ$^4$-[1,4]thiazino[2,1-g][[1,2]thiazepin-8-yl)-5-fluoropyridin-2-yl]-5-fluoro-3-methylpyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-3-chloro-5-cyanopyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-(difluoromethoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-(2,2-difluoroethoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-(2,2,3,3-tetrafluoropropoxy)pyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl]-5-cyano-3-methylpyridine-2-carboxamide N-{6-[(4aS,7R)-5-Amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl]-5-cyano-3-methylpyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl]-3-chloro-5-cyanopyridine-2-carboxamide, N-{6-[(4aS,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl]-3-chloro-5-cyanopyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl]-5-(2,2,3,3-tetrafluoropropoxy)pyridine-2-carboxamide, N-{6-[(4aS,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-Amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-Amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aR,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aS,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7R)-5-Amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide, N-{6-[(4aS,7S)-5-Amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, and N-{6-[(4aR,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, or pharmaceutically acceptable salts thereof.

A certain embodiment of the invention provides a compound of formula I as described herein that is selected from the group consisting of N-{6-[(4aS,7R)-5-Amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide, N-[6-(6-amino-5a,8-dimethyl-10-oxido-3,4,5,5a,8,9-hexahydro-2H-10λ⁴-[1,4]thiazino[2,1-g][1,2]thiazepin-8-yl)-5-fluoropyridin-2-yl]-5-cyano-3-methylpyridine-2-carboxamide (stereoisomer A), N-[6-(6-amino-5a,8-dimethyl-10-oxido-3,4,5,5a,8,9-hexahydro-2H-10λ⁴-1,4]thiazino[2,1-g][1,2]thiazepin-8-yl)-5-fluoropyridin-2-yl]-5-cyano-3-methylpyridine-2-carboxamide (stereoisomer B), N-[6-(6-amino-5a,8-dimethyl-10-oxido-3,4,5,5a,8,9-hexahydro-2H-10λ⁴-1,4]thiazino[2,1-g][1,2]thiazepin-8-yl)-5-fluoropyridin-2-yl]-5-cyano-3-methylpyridine-2-carboxamide (stereoisomer D), N-{6-[(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide N-{6-[(4aS,7R)-5-Amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-3-chloro-5-cyanopyridine-2-carboxamide, N-{6-[(4aS,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-3-chloro-5-cyanopyridine-2-carboxamide, N-{6-[(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aS,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-Amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aS,7S)-5-Amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aR,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aS,7S)-5-Amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, N-{6-[(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, and N-{6-[(4aR,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methyl-pyridine-2-carboxamide, or pharmaceutically acceptable salts thereof.

A certain embodiment of the invention provides a compound of formula I as described herein that is selected from the group consisting of N-(6-(5-Amino-4a,7-dimethyl-9-oxido-2,3,4,4a,7,8-hexahydro-[1,4]thiazino[2,1-f][1,2]thiazin-7-yl)-5-fluoropyridin-2-yl)-5-cyano-3-methylpicolinamide, N-(6-(6-Amino-5a,8-dimethyl-10-oxido-3,4,5,5a,8,9-hexahydro-2H-[1,4]thiazino[2,1-g][1,2]thiazepin-8-yl)-5-fluoropyridin-2-yl)-5-cyano-3-methylpicolinamide (stereoisomer A), N-(6-(6-Amino-5a,8-dimethyl-10-oxido-3,4,5,5a,8,9-hexahydro-2H-[1,4]thiazino[2,1-g][1,2]thiazepin-8-yl)-5-fluoropyridin-2-yl)-5-cyano-3-methylpicolinamide (stereoisomer B), and N-(6-(6-Amino-5a,8-dimethyl-10-oxido-3,4,5,5a,8,9-hexahydro-2H-[1,4]thiazino[2,1-g][1,2]thiazepin-8-yl)-5-fluoropyridin-2-yl)-5-cyano-3-methylpicolinamide (stereoisomer D), or pharmaceutically acceptable salts thereof.

A certain embodiment of the invention provides a compound of formula I as described herein whenever prepared by a process as described herein.

A certain embodiment of the invention provides a compound of formula I as described herein for use as therapeutically active substance.

A certain embodiment of the invention provides a compound of formula I as described herein for the use as inhibitor of BACE1 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides a compound of formula I as described herein for the use in inhibition of BACE1 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits or Alzheimer's disease.

A certain embodiment of the invention provides a compound of formula I as described herein for the use in the therapeutic and/or prophylactic treatment of Alzheimer's disease.

A certain embodiment of the invention provides a method for the use in inhibition of BACE1 activity, particularly for the therapeutic and/or prophylactic treatment of diseases and disorders characterized by elevated β-amyloid levels and/or β-amyloid oligomers and/or β-amyloid plaques and further deposits or Alzheimer's disease, which method comprises administering compound of formula I as described herein to a human being or animal.

A certain embodiment of the invention provides a method for the use in the therapeutic and/or prophylactic treatment of Alzheimer's disease, which method comprises administering a compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric form

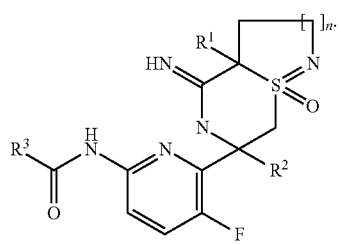

If

All tautomeric forms are encompassed in the present invention.

The compounds of formula I may contain one or more asymmetric centers and can therefore occur as racemates, racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography.

In the embodiments, where optically pure enantiomers are provided, optically pure enantiomer means that the compound contains >90% of the desired isomer by weight, particularly >95% of the desired isomer by weight, or more particularly >99% of the desired isomer by weight, said weight percent based upon the total weight of the isomer(s) of the compound. Chirally pure or chirally enriched compounds may be prepared by chirally selective synthesis or by separation of enantiomers. The separation of enantiomers may be carried out on the final product or alternatively on a suitable intermediate.

Scheme 1: general scheme A

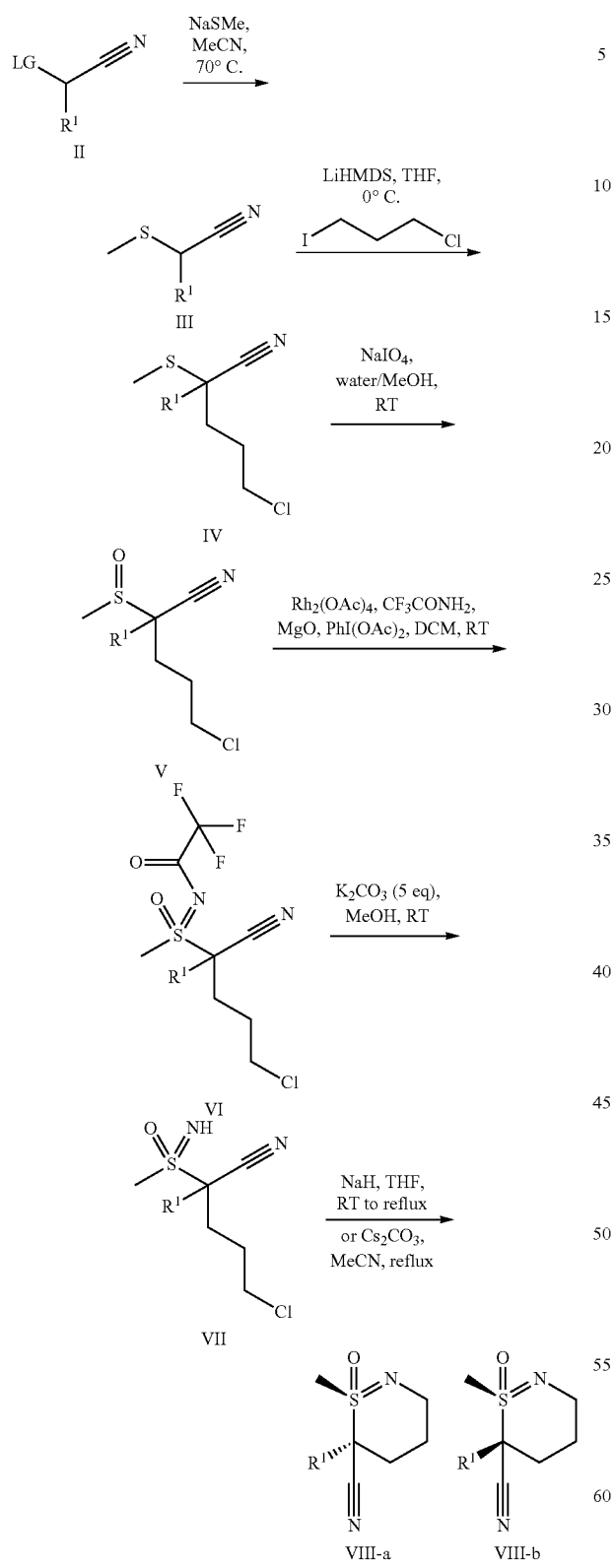

chloride or bromide) in a solvent such as acetonitrile at room temperature to reflux. Compounds of formula IV are obtained according to methods known in the art, e.g. by consecutive treatment of a compound of formula III with an organic base such as lithium diisopropylamide or lithium bis(trimethylsilyl)amide and an electrophilic reactant such as 1-chloro-3-iodopropane. Sulfoxide intermediates of formula V are obtained by treatment of a compound of formula IV with an oxidizing reagent such as sodium periodate in a solvent mixture such as 1,4-dioxane and water at room temperature. Compounds of formula VI are obtained from sulfoxide intermediate of formula V by methods known in the art, e.g. by treatment with iodobenzene diacetate, trifluoroacetamide and magnesium oxide in a solvent such as dichloromethane at room temperature using a catalytic amount of dirhodiumacetate dimer. Sulfoximine intermediates of formula VII can be prepared by hydrolysis of compounds of formula VI using potassium carbonate in methanol. Intermediates of formula VIII-a and VIII-b can be prepared from intermediates of formula VII by intramolecular alkylation in a solvent such as tetrahydrofuran at room temperature to reflux using a base such as sodium hydride. Alternatively intermediates of formula VIII-a and VIII-b can be prepared by intramolecular alkylation in a solvent such as acetonitrile at room temperature to reflux using a base such as cesium or potassium carbonate.

Scheme 2: general scheme B

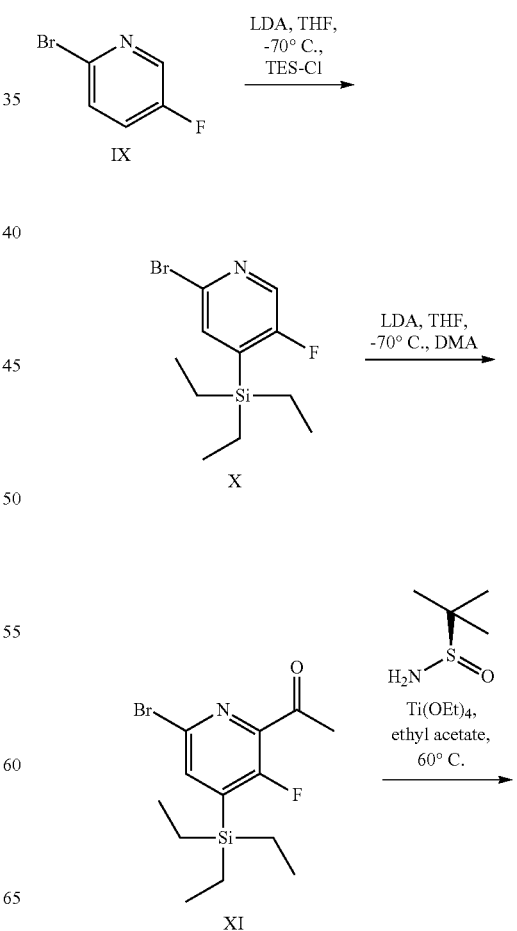

(Methylthiopropane)nitrile intermediates of formula III can be prepared by reaction of a sodium methoxide with a nitrile of formula II (wherein LG is a leaving group like -continued

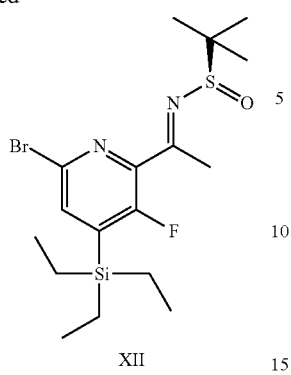

XII

An intermediate of formula X can be prepared by consecutive treatment of a compound of formula IX with a base such as lithium diisopropylamide in tetrahydrofuran at −78° C. and triethylchlorosilane. An intermediate of formula XI can be prepared by consecutive treatment of a compound of formula X with a base such as lithium diisopropylamide in tetrahydrofuran at −78° C. and dimethylacetamide. Treatment of an intermediate of formula XI with (R)-2-methylpropane-2-sulfinamide in ethyl acetate at 60° C. using titanium (IV) ethoxide gives a ketimine intermediate of formula XII.

Scheme 3: general scheme C

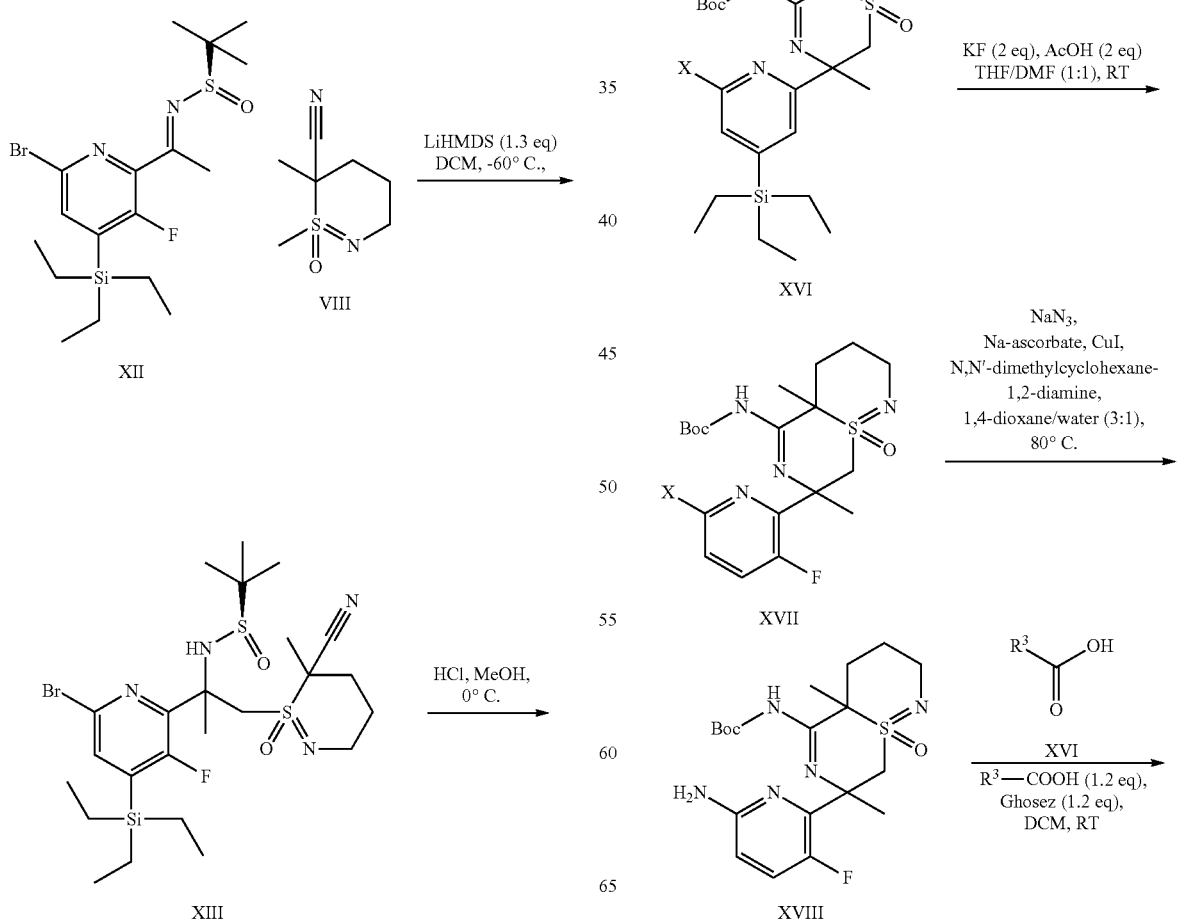

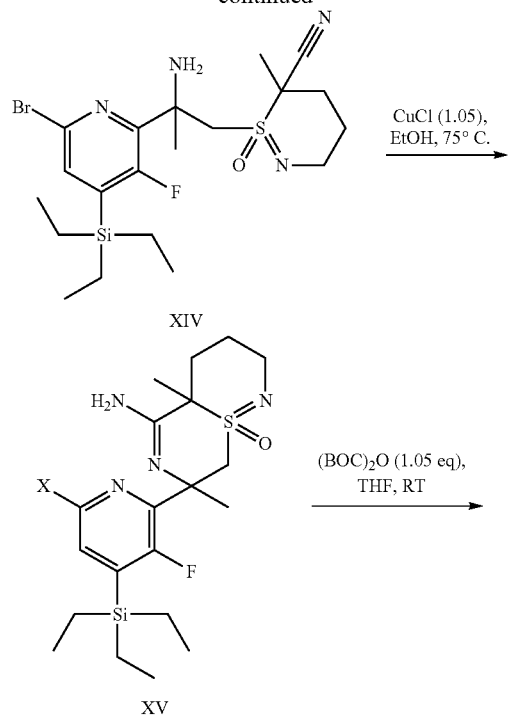

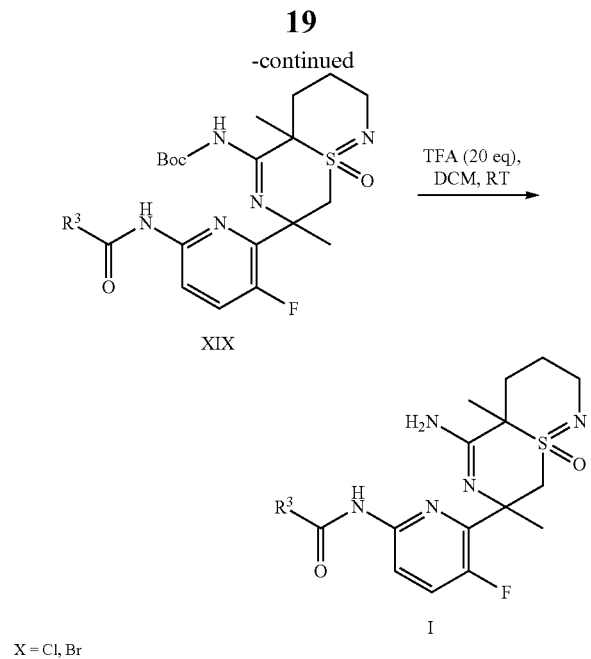

XIX

X = Cl, Br

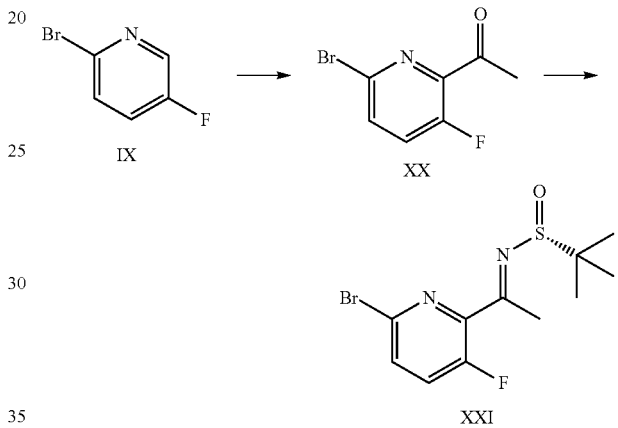

I

Intermediates of formula XIII can be prepared by consecutive treatment of a sulfoximine intermediate of formula VIII with lithium bis(trimethylsilyl)amide in dichloromethane at −60° C. and a ketimine intermediate of formula XII. Alternatively an intermediate of formula XIII can be prepared by consecutive treatment of a sulfoximine intermediate of formula VIII with n-butyllithium in tetrahydrofuran at −78° C. and a ketimine intermediate of formula XIII. Deprotection of an intermediate of formula XIII with hydrogen chloride in methanol at 0° C. gives an intermediate of formula XIV, which can be cyclized to an intermediate of formula XV according to methods known in the art, e.g. treatment with copper(I) chloride in ethanol at 75° C. or treatment with aluminumtrimethyl in toluene at room temperature to 60° C. Treatment of an intermediate of formula XV with di-tert-butyl dicarbonate in tetrahydrofuran at room temperature gives an intermediate of formula XVI, which can be converted to an intermediate of formula XVII by treatment with potassium fluoride and acetic acid in tetrahydrofuran/N,N-dimethylformamide at room temperature Aminopyridine intermediates of formula xxx can be prepared from intermediate of formula XVIII by treatment with sodium azide and sodium ascorbate in 1,4-dioaxne/water at 70° C. using copper(I) iodide and trans-N,N'-dimethylcyclohexane-1,2-diamine. Intermediates of formula XIX can be prepared by treatment of aminopyridine intermediates of formula XVIII with acid intermediates of formula XVI, which are either commercially available or easily prepared according to methods and starting materials well known in the art, with an activating agent such as 1-chloro-N,N,2-trimethylprop-1-en-1-amine or oxalyl chloride in dichloromethane. Treatment of an intermediate of formula XIX with trifluoroacetic acid in dichloromethane gives compounds of formula I.

Scheme 4: general scheme D

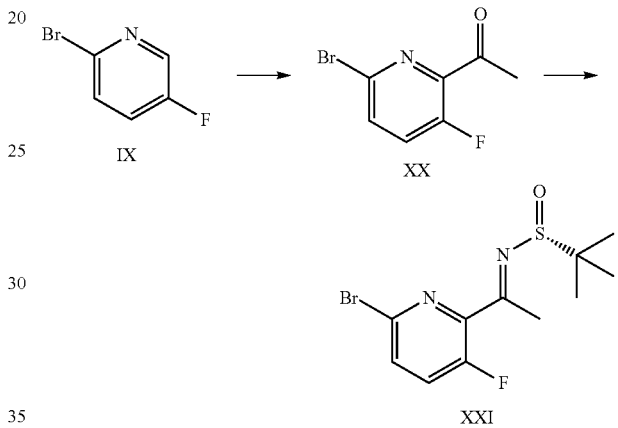

An intermediate of formula XX can be prepared by consecutive treatment of a compound of formula IX with a base such as n-butyllithium in dry diethylether at −78° C. and n-methoxy-n-methylacetamide. Treatment of the intermediate of formula XX with (R)-2-methylpropane-2-sulfinamide in dry tetrahydrofuran at 60° C. using titanium (IV) ethoxide gives a ketimine intermediate of formula XXI.

Scheme 5: general scheme E

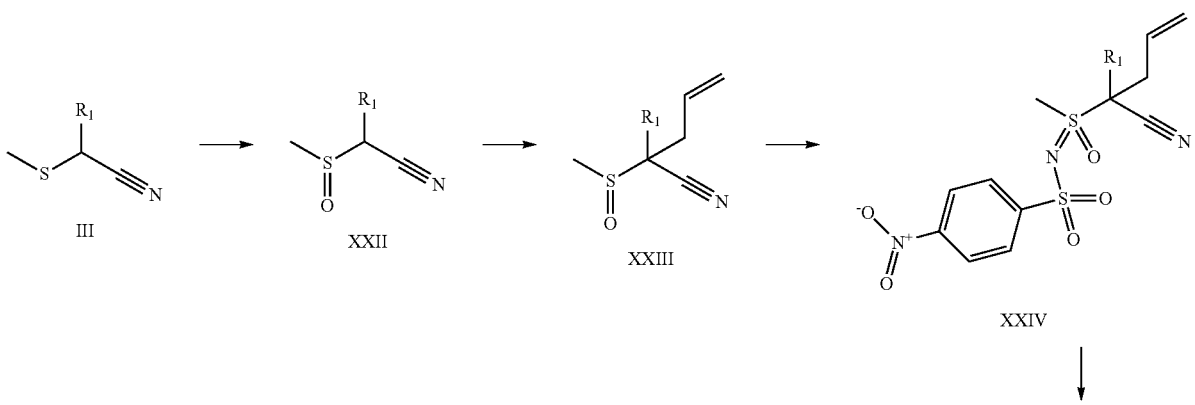

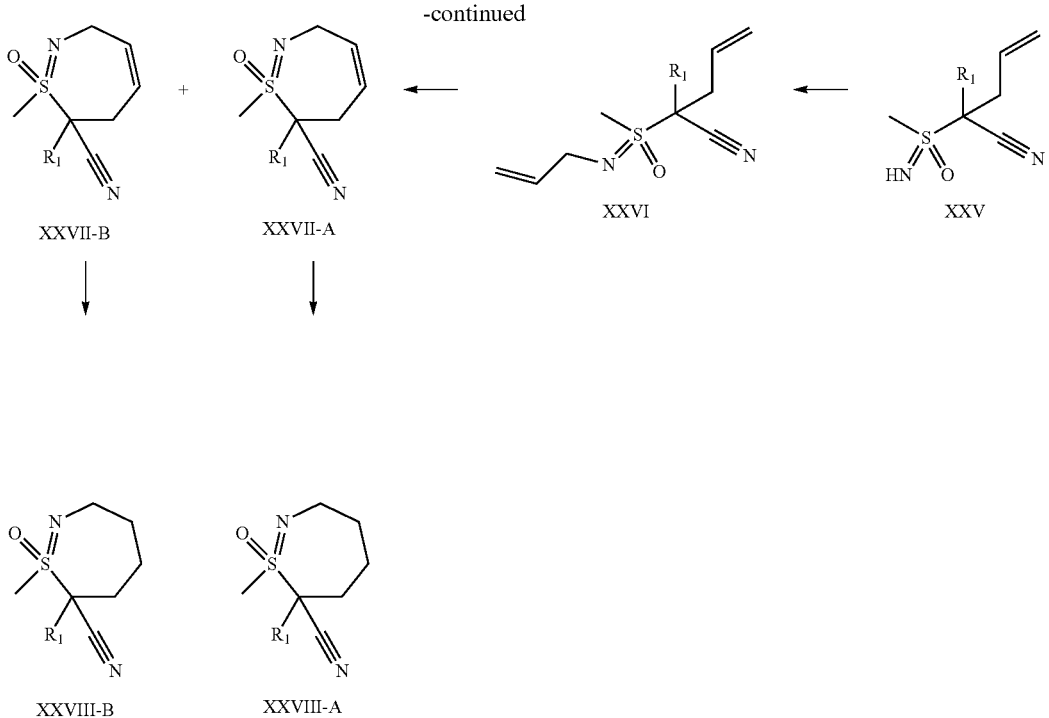

Compounds of formula XXII are obtained according to methods known in the art, e.g. by treatment of a compound of formula III with an oxidizing reagent such as sodium periodate in a solvent mixture such as 1,4-dioxane and water at room temperature or m-CPBA in dichloromethane at 0° C. Compounds of formula XXIII are obtained by treatment of compounds XXII with an appropriate base, such as sodium hydride or lithium bis(trimethylsilyl)amide and an electrophilic reactant such as allyl bromide in a solvent such as tetrahydrofuran. Sulfoximine intermediates of formula XXIV are prepared from compounds of formula XXIII by methods known in the art, e.g. by treatment with diacetoxyiodosobenzene, 4-nitrobenzenesulfonamide in a solvent such as acetonitrile at 60° C. using a catalytic amount of silver nitrate and a suitable ligand such as 4,4',4'''-tri-tert-Butyl-2,2':6',2''-terpyridine. Sulfoximine of formula XXV can be prepared by hydrolysis of compounds of formula XXIV using thiophenol and cesium carbonate in acetonitrile. Intermediates of formula XXVI are synthesized from compounds XXV by consecutive treatment with an appropriate base such as sodium hydride and an electrophile such as allyl iodide in dimethoxyethane as solvent. Ring structures of formula XXVII are obtained from compounds XXVI by a metathesis reaction using a catalytic amount of second generation Grubbs' catalyst producing a mixture of four stereoisomers that can be separated by chromatography on silica into two racemic mixtures XXVII-A and XXVII-B. Cyclic sulfoximine structures of formula XXVIII-A amd XXVIII-B are prepared by reduction of intermediates XXVII-A and XVII-B respectively using an appropriate catalyst such as palladium on charcoal under a pressurized hydrogen atmosphere in a suitable solvent such as ethanol or methanol.

Scheme 6: general scheme F

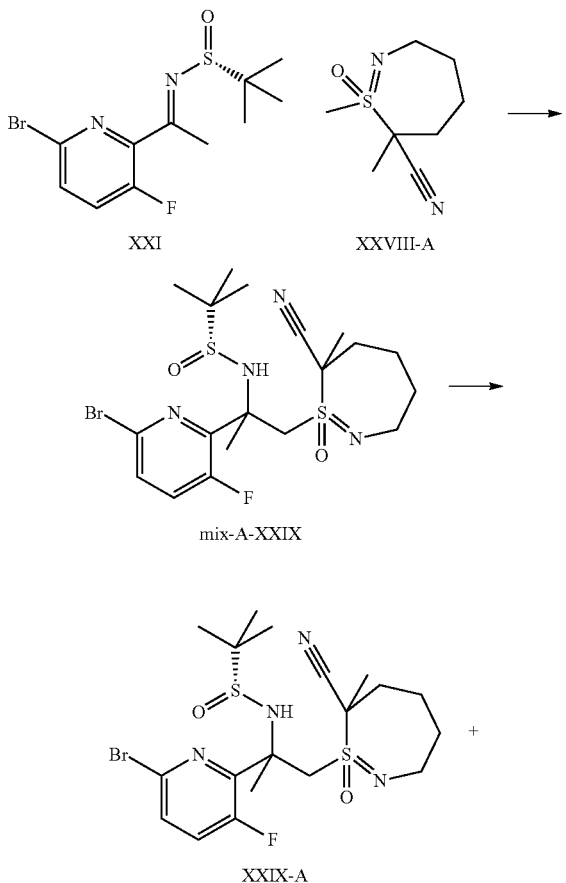

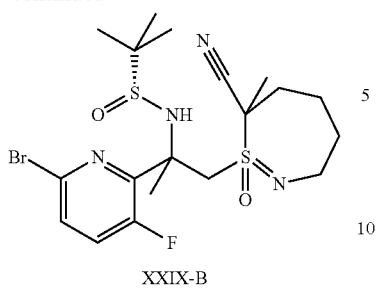

XXIX-B

Ketimine intermediate XXI can then be reacted with sulfoximine XXVIII-A in the presence of a strong base, e.g. an alkali hexamethyldisilazide, such as lithium hexamethyldisilazide, alkali diisopropylamide, such as lithium diisopropylamide, or alkyl lithium, such as n-butyl lithium, under anhydrous conditions in a suitable aprotic solvent, e.g. tetrahydrofuran, to form intermediate mix-A-XXIX as a mixture of 2 major stereoisomers. The single stereoisomers XXIX-A and XXIX-B can be separated at this stage by chromatography on silica.

Scheme 7: general scheme G

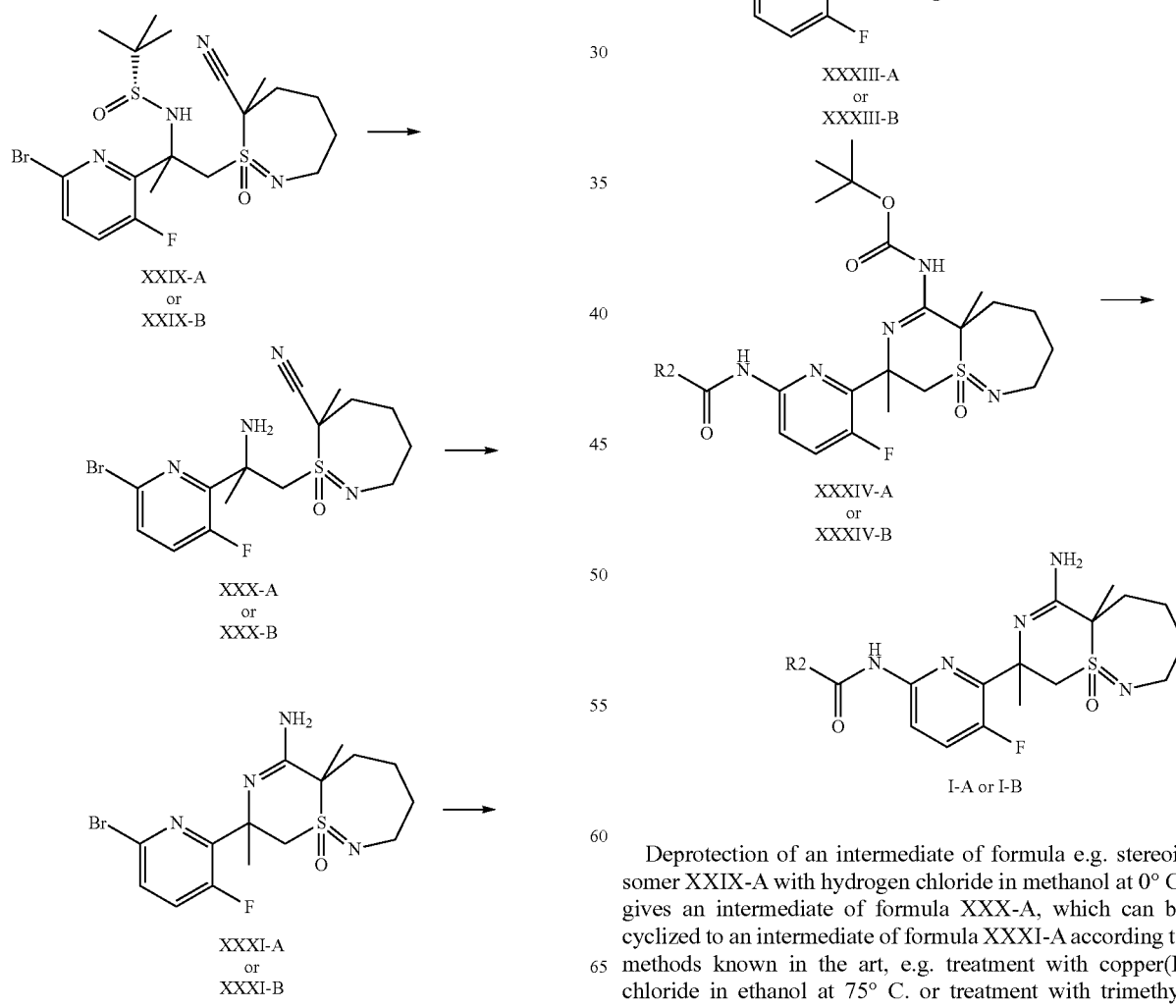

XXIX-A or XXIX-B

XXX-A or XXX-B

XXXI-A or XXXI-B

XXXII-A or XXXII-B

XXXIII-A or XXXIII-B

XXXIV-A or XXXIV-B

I-A or I-B

Deprotection of an intermediate of formula e.g. stereoisomer XXIX-A with hydrogen chloride in methanol at 0° C. gives an intermediate of formula XXX-A, which can be cyclized to an intermediate of formula XXXI-A according to methods known in the art, e.g. treatment with copper(I) chloride in ethanol at 75° C. or treatment with trimethyl aluminum in toluene at room temperature to 60° C. Treatment of an intermediate of formula XXXI-A with di-tert-butyl dicarbonate and a suitable base such as triethylamine or diisopropylethylamine in tetrahydrofuran at room temperature gives an intermediate of formula XXXII-A. Aminopyridine intermediates of formula XXXIII-A can be prepared from intermediate of formula XXXII-A by treatment with sodium azide and sodium ascorbate in a mixture of 1,4-dioxane/water at 70° C. using a catalytic amount of copper(I) iodide and a suitable diamine ligand such as trans-N,N'-dimethylcyclohexane-1,2-diamine. Intermediates of formula XXXIV-A can be prepared by treatment of aminopyridine intermediates of formula XXXIII-A with carboxylic acids, which are either commercially available or easily prepared according to methods and starting materials well known in the art, with an activating agent such as 1-chloro-N,N,2-trimethylprop-1-en-1-amine in dichloromethane. Final deprotection of an intermediate of formula XXXIV-A with trimethylsilyltriflate and 1,3-dimethoxybenzene in dry dichloromethane at 0° C. gives compounds of formula I-A as a single stereoisomer.

In analogy to the chemistry described above in Scheme 7 for the transformation of intermediate XXIX-A into intermediate I-A, intermediate XXIX-B can be transformed into compound I-B as a single stereoisomer.

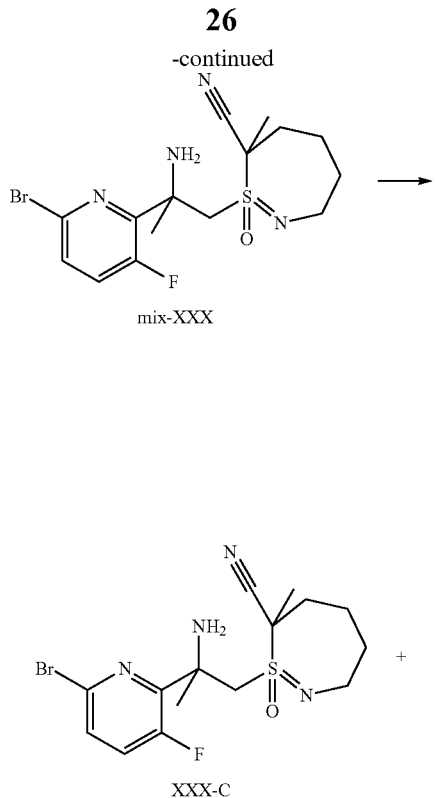

Scheme 8: general scheme H

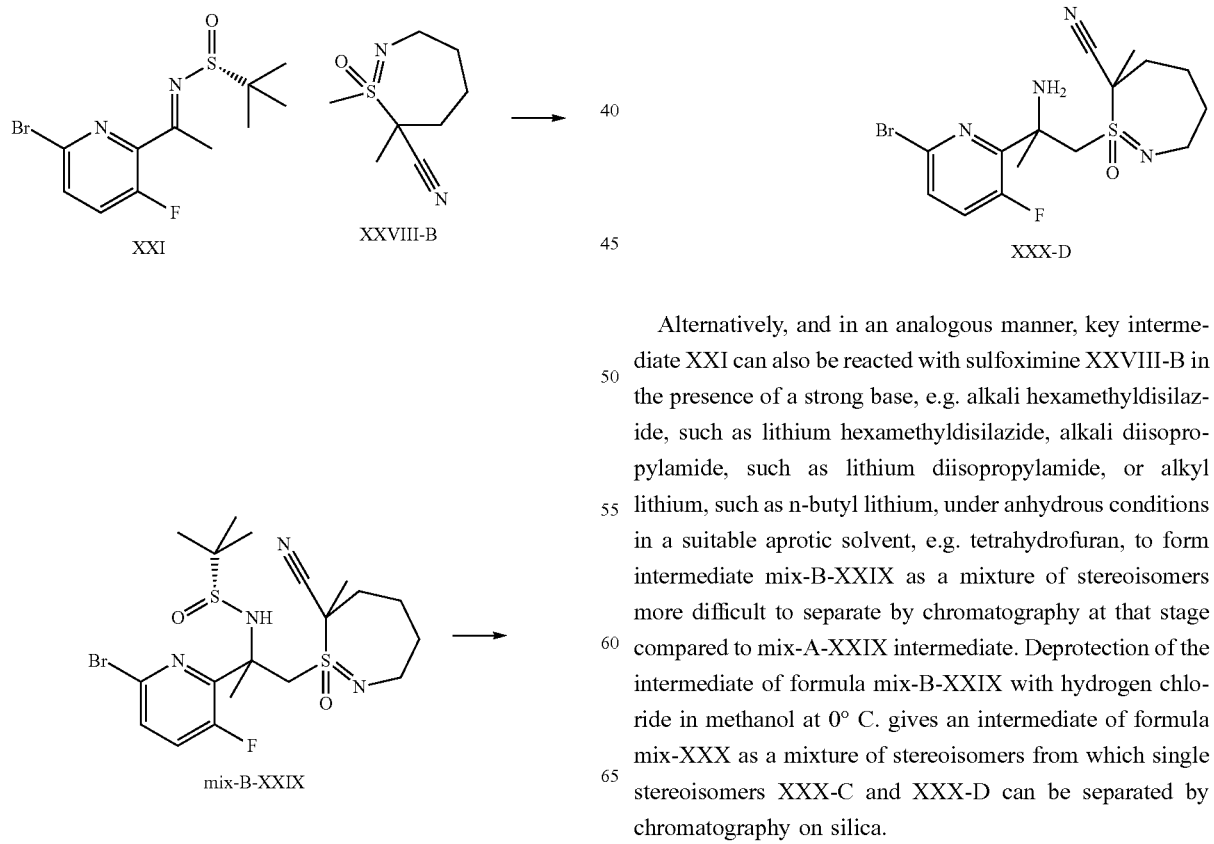

Alternatively, and in an analogous manner, key intermediate XXI can also be reacted with sulfoximine XXVIII-B in the presence of a strong base, e.g. alkali hexamethyldisilazide, such as lithium hexamethyldisilazide, alkali diisopropylamide, such as lithium diisopropylamide, or alkyl lithium, such as n-butyl lithium, under anhydrous conditions in a suitable aprotic solvent, e.g. tetrahydrofuran, to form intermediate mix-B-XXIX as a mixture of stereoisomers more difficult to separate by chromatography at that stage compared to mix-A-XXIX intermediate. Deprotection of the intermediate of formula mix-B-XXIX with hydrogen chloride in methanol at 0° C. gives an intermediate of formula mix-XXX as a mixture of stereoisomers from which single stereoisomers XXX-C and XXX-D can be separated by chromatography on silica.

Scheme 9: general scheme I

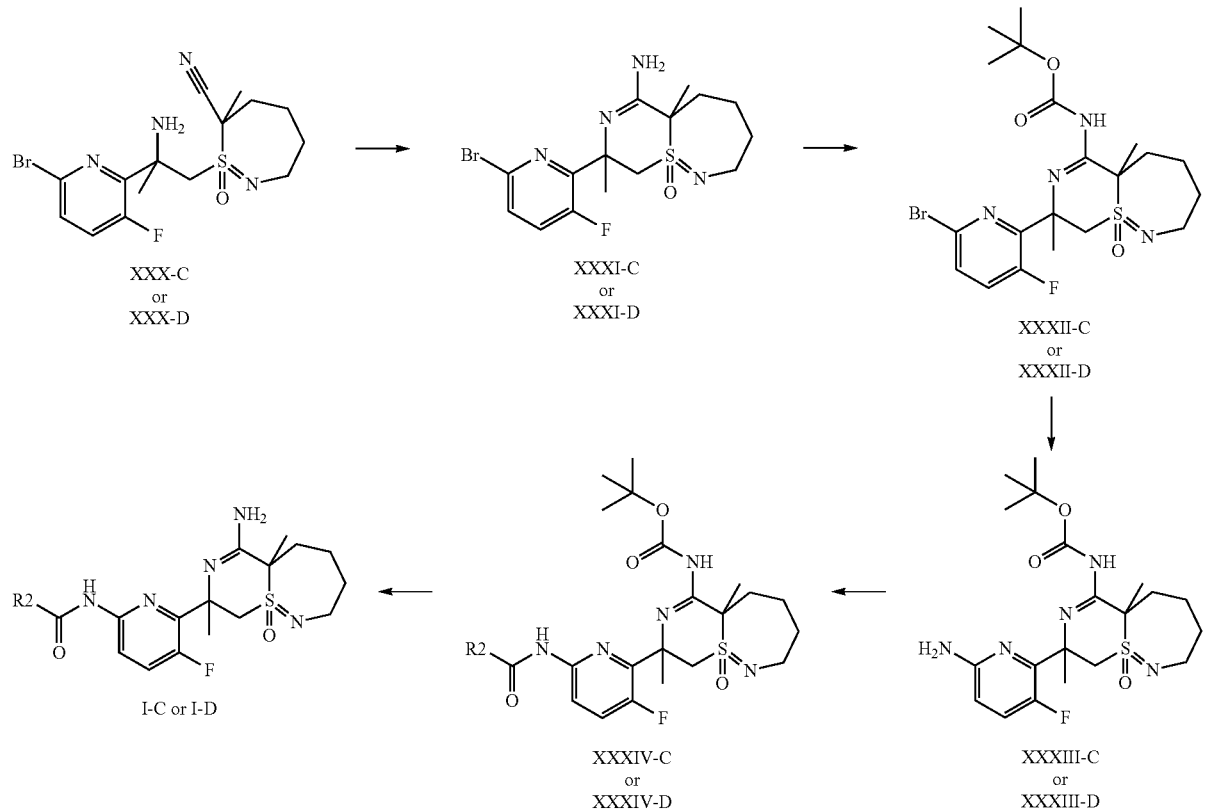

In analogy to the chemistry described above in Scheme 7 for the transformation of intermediate XXX-A into intermediate I-A, more polar intermediate XXX-D can be transformed into I-D.

Scheme 10: general scheme J

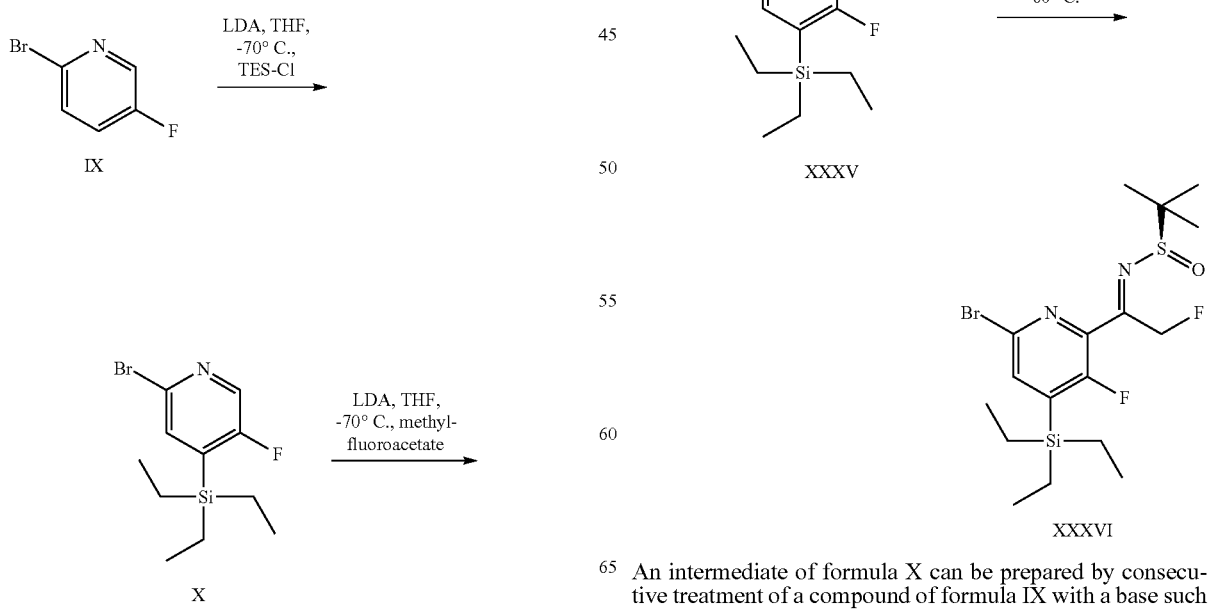

An intermediate of formula X can be prepared by consecutive treatment of a compound of formula IX with a base such as lithium diisopropylamide in tetrahydrofuran at −78° C.

and triethylchlorosilane. An intermediate of formula XXXV can be prepared by consecutive treatment of a compound of formula X with a base such as lithium diisopropylamide in tetrahydrofuran at −78° C. and methyl fluoroacetate. Treatment of an intermediate of formula XXXV with (R)-2-methylpropane-2-sulfinamide in ethyl acetate at 60° C. using titanium (IV) ethoxide gives a ketimine intermediate of formula XXXVI.

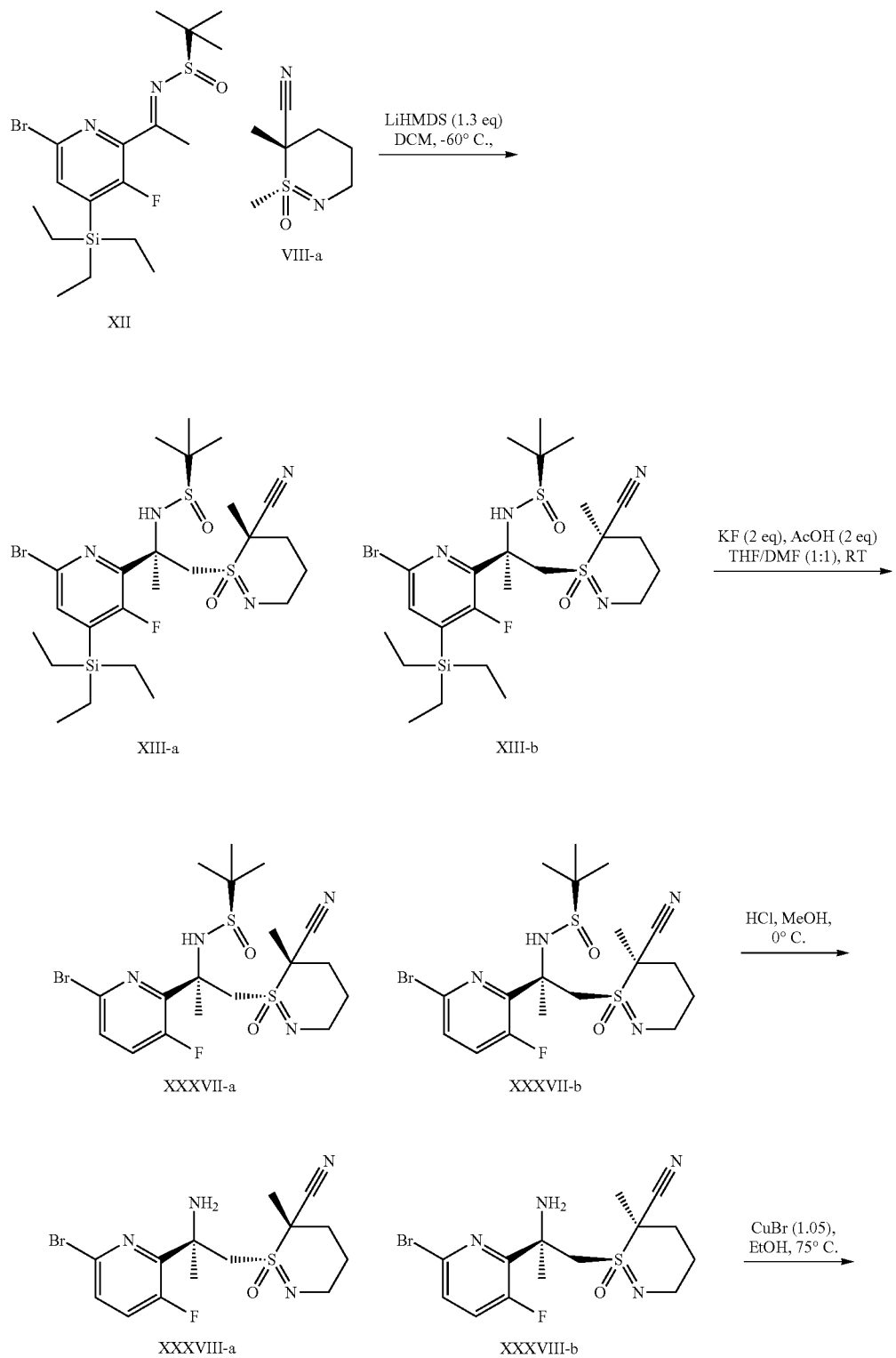

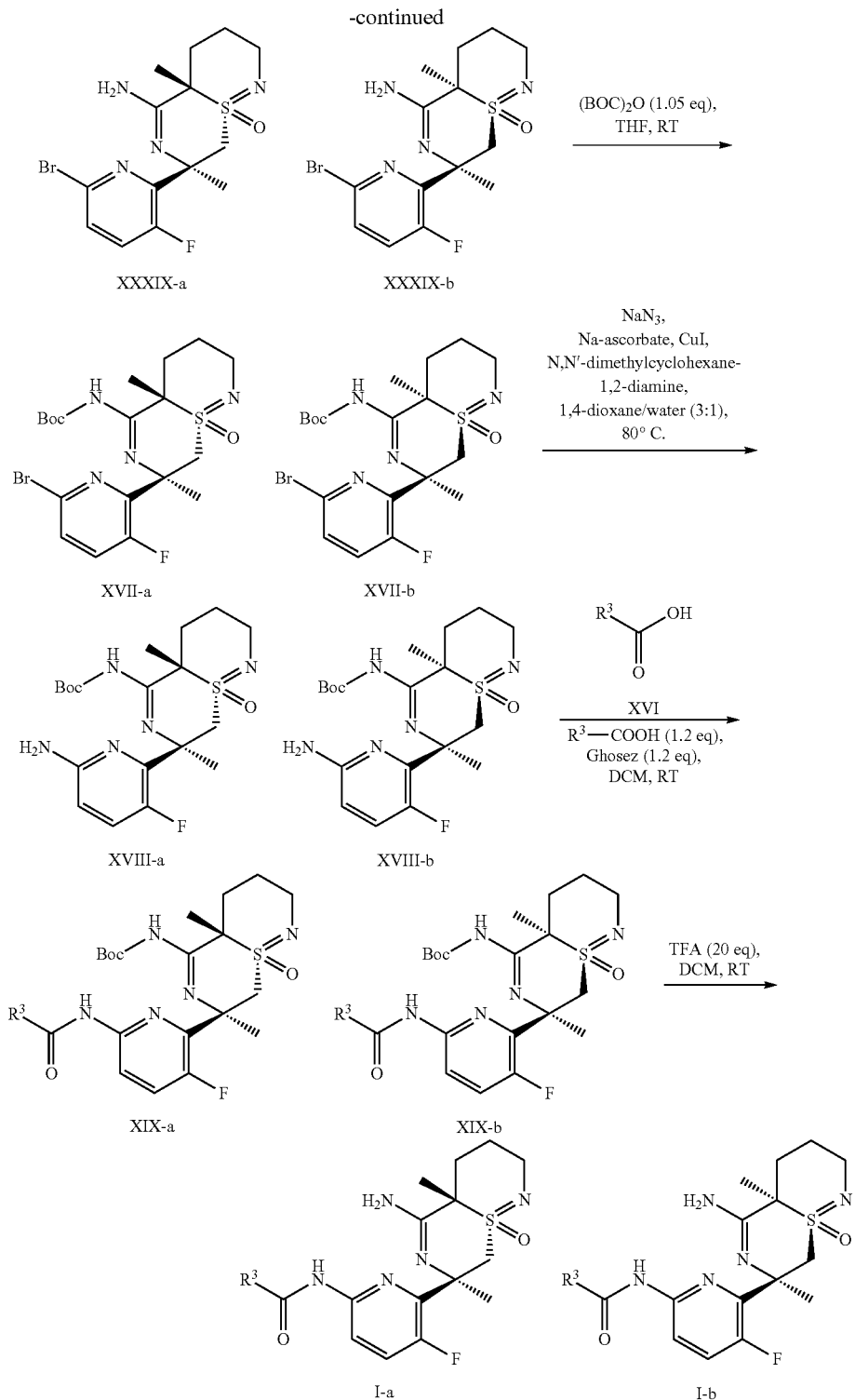

Intermediates of formula XIII-a and XIII-b can be obtained by consecutive treatment of a sulfoximine intermediate of formula VIII-a with lithium bis(trimethylsilyl)amide in dichloromethane at −60° C. and a ketimine intermediate of formula XII. Alternatively intermediates of formula XIII-a and XIII-b can be prepared by consecutive treatment of a sulfoximine intermediate of formula VIII-a with n-butyllithium in tetrahydrofuran at −78° C. and a ketimine intermediate of formula XII. Treatment of and intermediate of formula XIII-a or XIII-b with potassium fluoride and acetic acid in a tetrahydrofuran/N,N-dimethylformamide mixture at room temperature gives an intermediate of formula XXXVII-a or XXXVII-b. Deprotection of an intermediate of formula XXXVII-a or XXXVII-b with hydrogen chloride in methanol at 0° C. gives an intermediate of formula XXXVIII-a or XXXVIII-b, which can be cyclized to an intermediate of formula XXXIX-a or XXXIX-b according to methods known in the art, e.g. treatment with copper(I) bromide in ethanol at 75° C. or treatment with aluminumtrimethyl in toluene at room temperature to 60° C. Treatment of an intermediate of formula XXXIX-a or XXXIX-b with di-tert-butyl dicarbonate in tetrahydrofuran at room temperature gives an intermediate of formula XVII-a or XVII-b Aminopyridine intermediates of formula XVIII-a or XVIII-b can be prepared from an intermediate of formula XVII-a or XVII-b by treatment with sodium azide and sodium ascorbate in 1,4-dioxane/water at 70° C. using copper(I) iodide and trans-N,N'-dimethylcyclohexane-1,2-diamine. Intermediates of formula XIX-a or XIX-b can be prepared by treatment of an aminopyridine intermediate of formula XVIII-a or XVIII-b with acid intermediates of formula XVI, which are either commercially available or easily prepared according to methods and starting materials well known in the art, with an activating agent such as 1-chloro-N,N,2-trimethylprop-1-en-1-amine or oxalyl chloride in dichloromethane. Alternatively an intermediate of formula XIX-a or XIX-b can be prepared by treatment of an aminopyridine intermediate of formula XVIII-a or XVIII-b with acid intermediates of formula XVI, which are either commercially available or easily prepared according to methods and starting materials well known in the art, with an activating agent such propylphosphonic anhydride and a base such as triethylamine or Hunig's Base in a solvent such as tetrahydrofuran at room temperature to reflux. Treatment of an intermediate of formula XIX-a or XIX-b with excess trifluoroacetic acid in dichloromethane at room temperature gives compounds of formula I-a or I-b.

Scheme 12: general scheme L

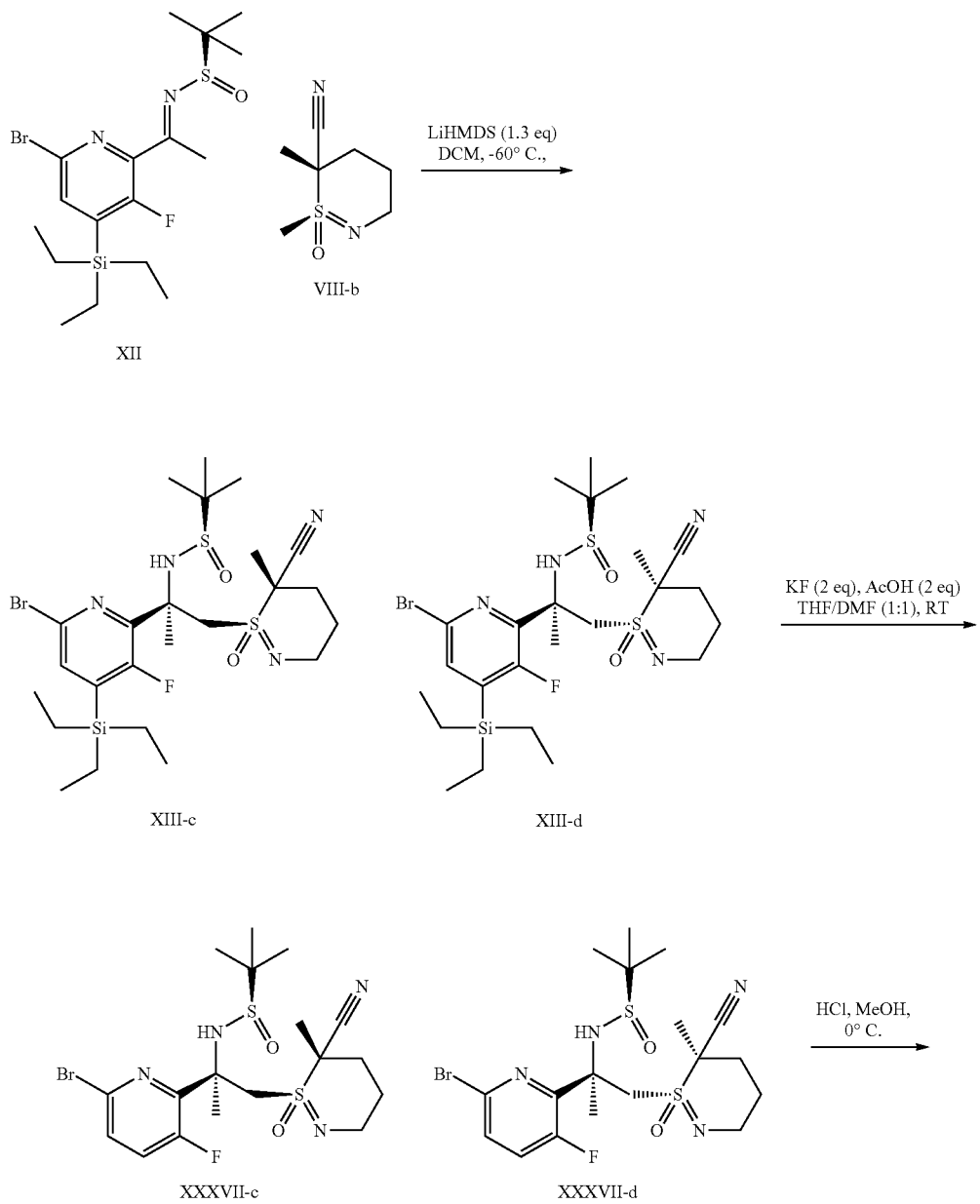

-continued
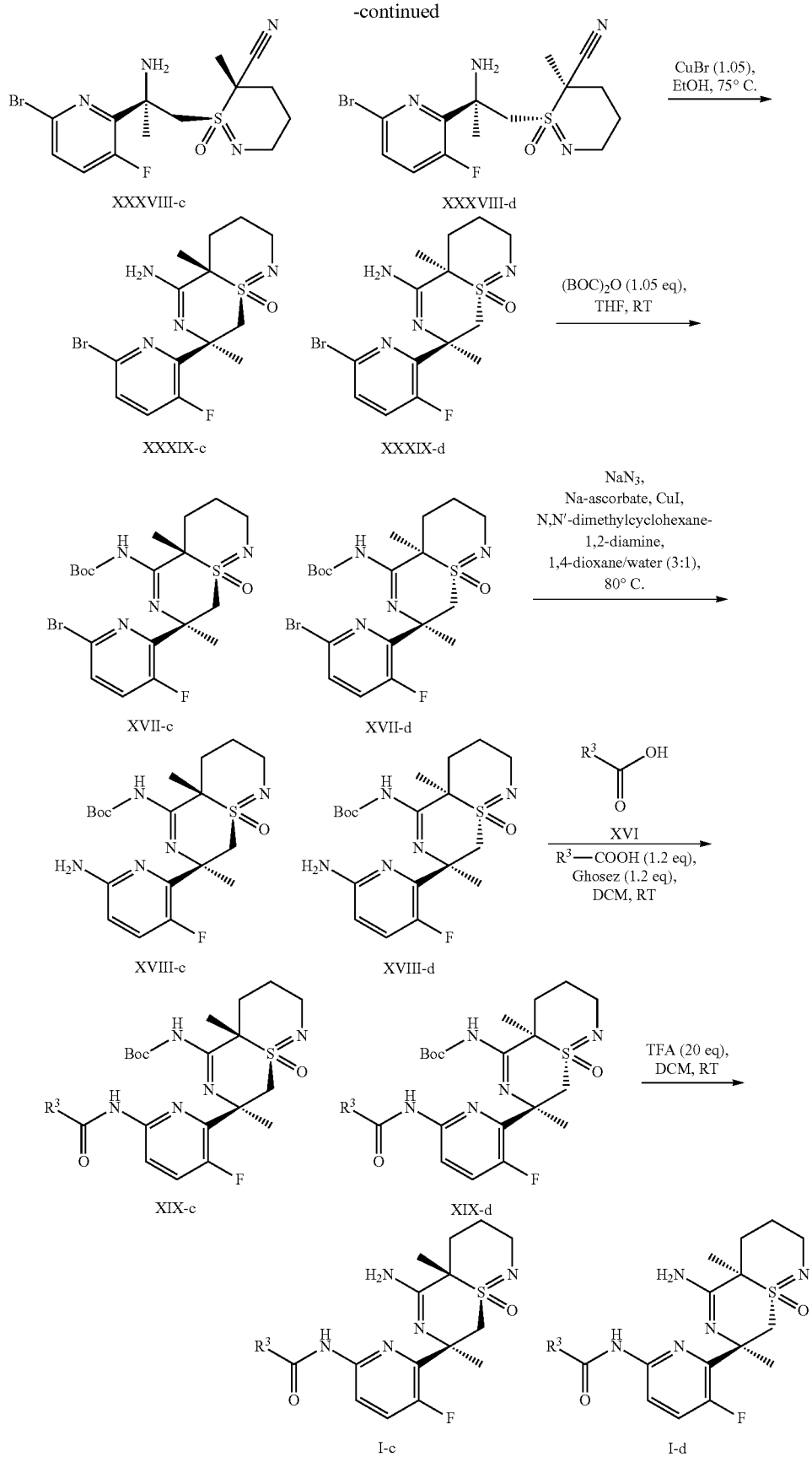

Compounds of formula I-c and I-d can be prepared in analogy to the chemistry described above in Scheme 11 for the synthesis of compounds I-a and I-b, starting from a ketimine intermediate of formula XII and a sulfoximine intermediate of formula VIII-b.
Scheme 13: general scheme M
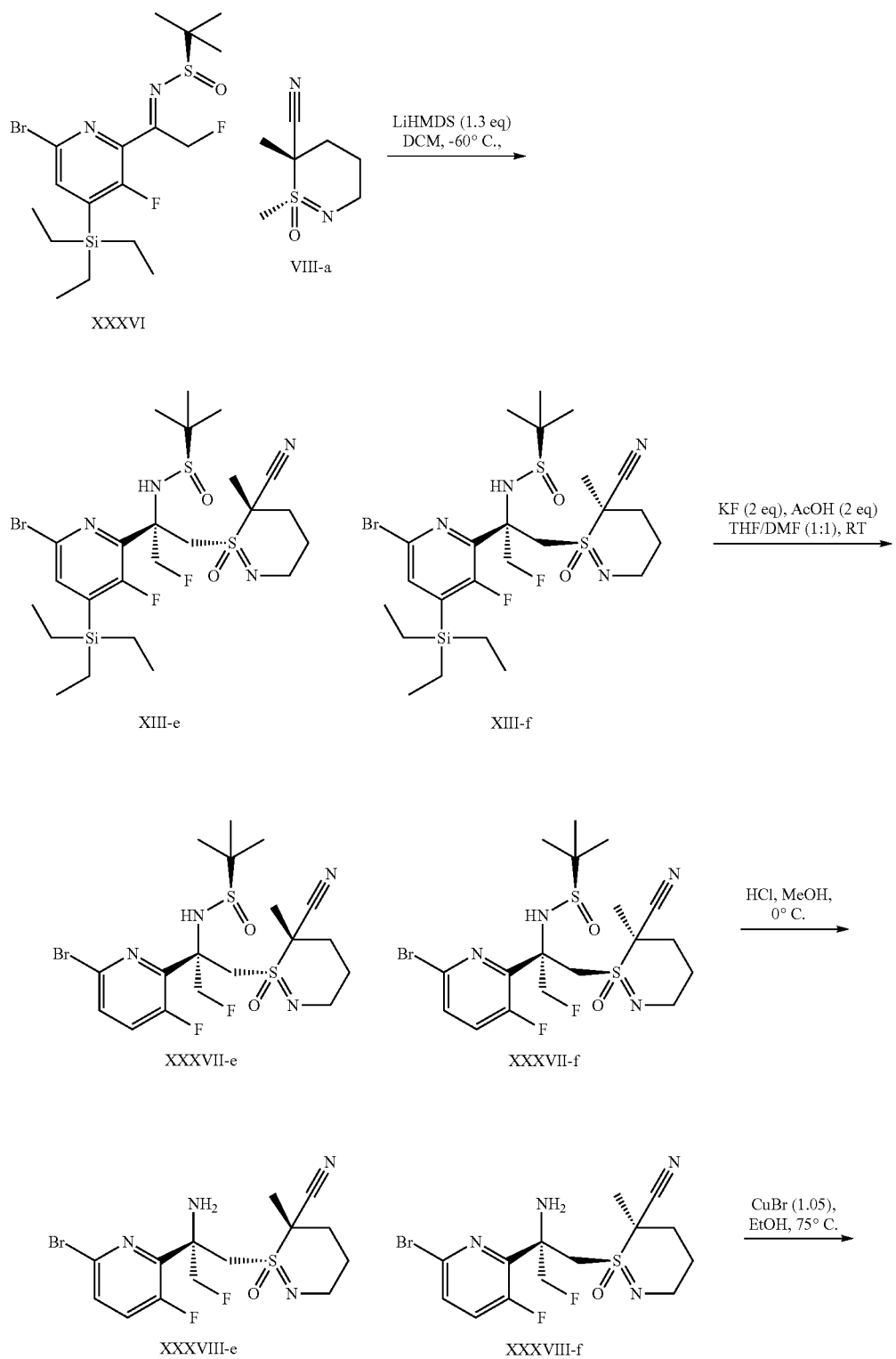

-continued

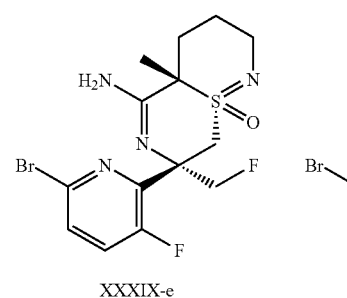

XXXIX-e     XXXIX-f (BOC)₂O (1.05 eq), THF, RT →

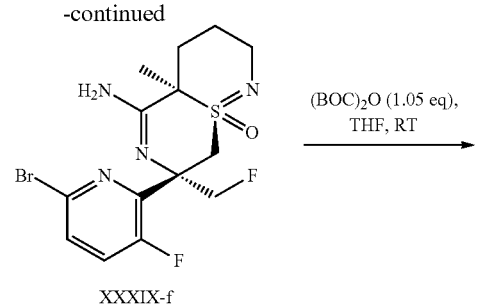

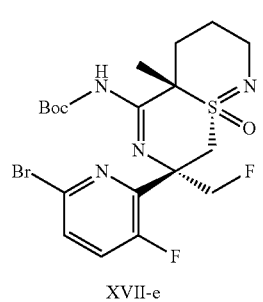

XVII-e

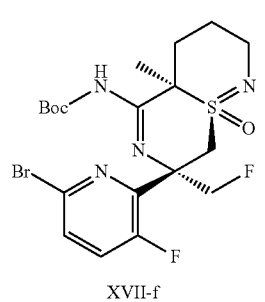

XVII-f

NaN₃, Na-ascorbate, CuI, N,N'-dimethylcyclohexane-1,2-diamine, 1,4-dioxane/water (3:1), 80° C. →

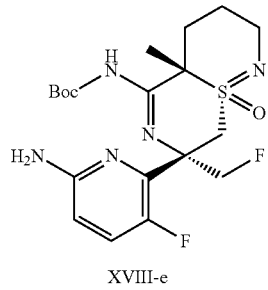

XVIII-e

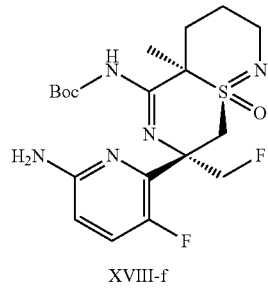

XVIII-f

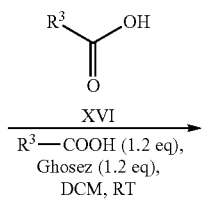

XVI
$R^3$—COOH (1.2 eq), Ghosez (1.2 eq), DCM, RT →

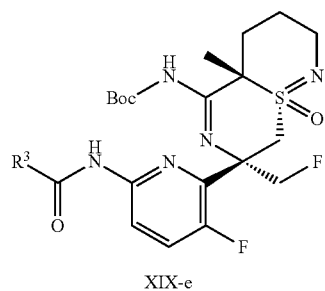

XIX-e

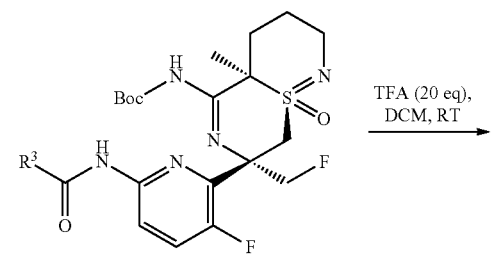

XIX-f

TFA (20 eq), DCM, RT →

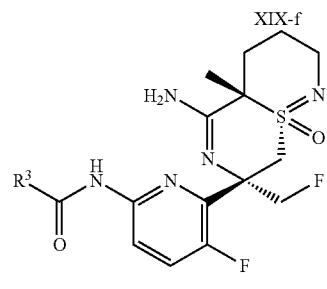

I-e

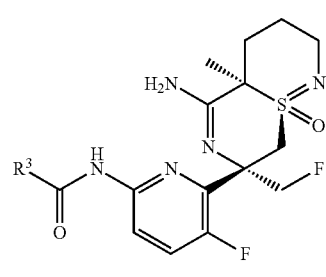

I-f

Compounds of formula I-e and I-f can be prepared in analogy to the chemistry described above in Scheme 11 for the synthesis of compounds I-a and I-b, starting from a ketimine intermediate of formula XXXVI and a sulfoximine intermediate of formula VIII-a.

Scheme 14: general scheme N
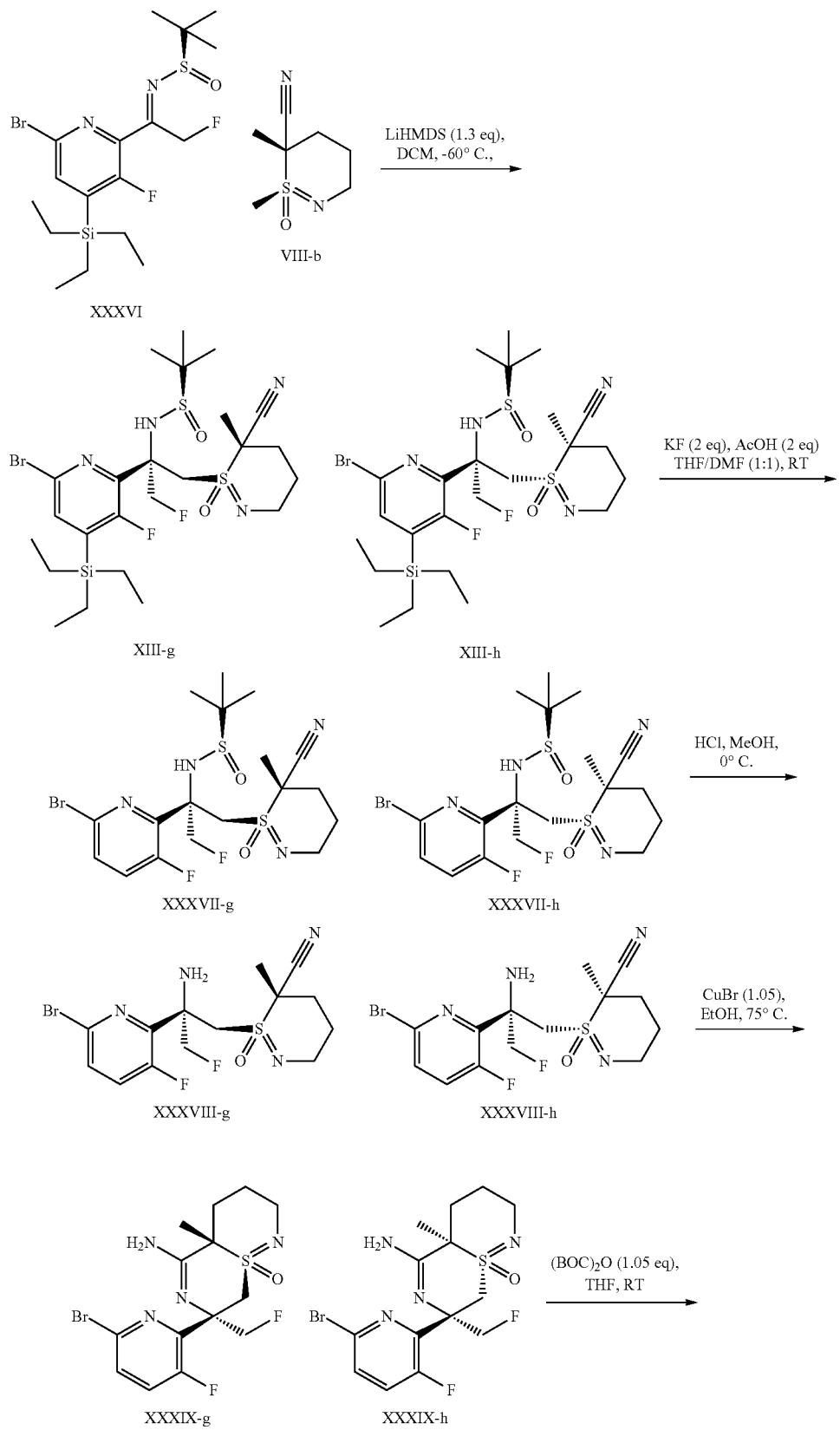

-continued

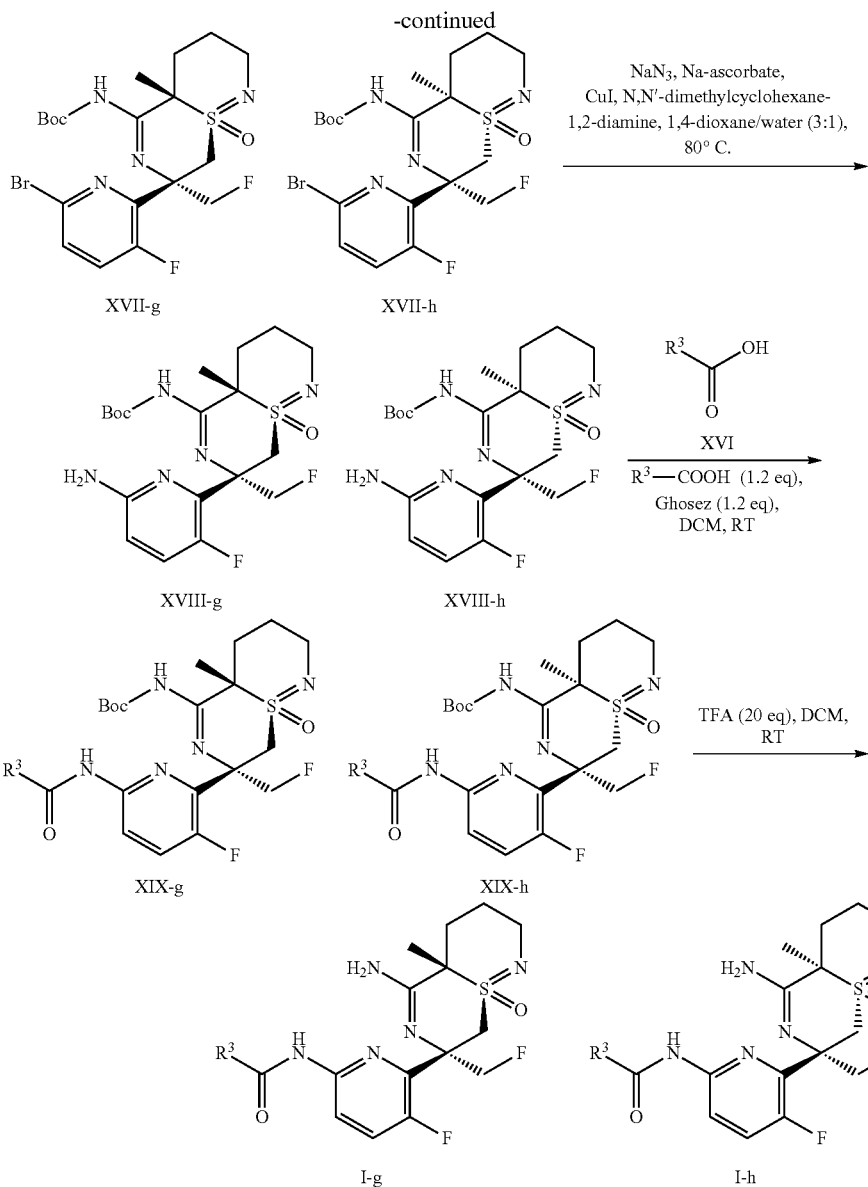

Compounds of formula I-g and I-h can be prepared in analogy to the chemistry described above in Scheme 11 for the synthesis of compounds I-a and I-b, starting from a ketimine intermediate of formula XXXVI and a sulfoximine intermediate of formula VIII-b.

The corresponding pharmaceutically acceptable salts with acids can be obtained by standard methods known to the person skilled in the art, e.g. by dissolving the compound of formula I in a suitable solvent such as e.g. dioxane or tetrahydrofuran and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation. Particular salts are hydrochloride, formate and trifluoroacetate.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of general formula I in this invention may be derivatised at functional groups to provide derivatives which are capable of conversion back to the parent compound in vivo.

Pharmacological Tests

The compounds of formula I and their pharmaceutically acceptable salts possess valuable pharmacological properties. It has been found that the compounds of the present invention are associated with inhibition of BACE1 activity. The compounds were investigated in accordance with the test given hereinafter.

Cellular Aβ-lowering Assay:

The Abeta 40 AlphaLISA Assay can be used. The HEK293 APP cells were seeded in 96 well Microtiter plates in cell culture medium (Iscove's, plus 10% (v/v) fetal bovine serum, penicillin/streptomycin) to about 80% confluency and the compounds were added at a 3× concentration in ⅓ volume of culture medium (final DMSO concentration was kept at 1% v/v). After 18-20 hrs incubation at 37° C. and 5% $CO_2$ in a humidified incubator, the culture supernatants were harvested for the determination of Aβ40 concentrations using Perkin-Elmer Human Amyloid beta 1-40 (high specificity) Kit (Cat# AL275C).

In a Perkin-Elmer White Optiplate-384 (Cat# 6007290), 2 ul culture supernatants were combined with 2 μl of a 10× AlphaLISA Anti-hAβAcceptor beads+Biotinylated Antibody Anti-Aβ1-40 Mix (50 μg/mL/5 nM). After 1 hour room temperature incubation, 16 μl of a 1.25 × preparation of Streptavidin (SA) Donor beads (25 μg/mL) were added and incubated for 30 minutes in the Dark. Light Emission at 615 nm was then recorded using EnVision-Alpha Reader. Levels of Aβ 40 in the culture supernatants were calculated as percentage of maximum signal (cells treated with 1% DMSO without inhibitor). The $IC_{50}$ values were calculated using the Excel XLfit software.

Lowering of Aβ40 in Brain of Wild-Type Mice:

Animals and Housing Conditions. Animals were maintained in a 12/12 h light/dark cycle, with lights starting at 6 a.m., and experiments were conducted during the light phase. Animal housing and experimental procedures were in line with ethical and legal guidelines and were authorized by local veterinary authorities.

Experiment. Female C57B1/6J mice were treated with a dose of 30 mg/kg of the compounds, 3-4 animals per treatment group. The test compound was dissolved in 5% EtOH, 10% Solutol, and was applied per os at 10 mL/kg. After 4 h, the animals were sacrificed and brain and plasma were collected. The brain was cut into halves and immediately frozen on dry ice. Brain was used for measurement of Aβ40 and plasma was used for determination of compound exposure. The method for Aβ40 determination in brain lysates followed the known procedure (Lanz, T. A.; Schachter, J. B. Demonstration of a common artifact in immunosorbent assays of brain extracts: development of a solidphase extraction protocol to enable measurement of amyloid-β from wild-type rodent brain. J. Neurosci. Methods 2006, 157, 71-81.). Brain tissue was homogenized in 2% DEA buffer in a Roche MagnaLyser (20", 4000 rpm) and subsequently centrifuged for 1 h at 100000 g. DEA was reduced to 0.2% in 50 mM NaCl and one-half of the DEA lysate was passed over an Oasis Solid phase extraction plate (Waters; cat. no. 186000679), which had been activated with MeOH and equilibrated in dH2O (1 mL each). After washes in 10% and 30% MeOH (1 mL each), the Aβ-peptides were eluted in 0.8 mL of 2% NH4OH in 90% MeOH. The eluate was dried over a N2 flow, and the dried sample was reconstituted in 30 μL of AlphaLISA assay buffer. Aβ40 was determined by an AlphaLISA assay (Perkin-Elmer). In a white 96-well, half area microplate (Perkin-Elmer cat. no. 6005561), 20 μL of the reconstituted sample were mixed with 5 μL of biotinylated BAP-24 (specific for C-terminus of Aβ40) (Brockhaus, M.; Grunberg, J.; Rohrig, S.; Loetscher, H.; Wittenburg, N.; Baumeister, R.; Jacobsen, H.; Haass, C. Caspasemediated cleavage is not required for the activity of presenilins in amyloidogenesis and NOTCH signaling. NeuroReport 1998, 9, 1481-1486.) stock=4.4 mg/mL, f.c.5.5 μg/mL), and 5 μL 252Q6 acceptor beads (252Q6 antibody, Invitrogen AMB0062) had been previously conjugated with AlphaLISA Acceptor beads (Perkin-Elmer cat. no. 6772002); final dilution 1:500). The mix was incubated for 1 h at RT in the dark. Then 20 μL of Streptavin-coated Donor Beads (Perkin-Elmer cat. no. 6760002, final dilution 1:125) were added and this final mix was incubated in the dark for another 30 min at RT before RFU was measured in an AlphaScreen Reader (Perkin-Elmer Envision 2104). The value obtained for Aβ40 in the treated animals was related to the value in the vehicle group and is given in %. Alternatively a commercial ELISA was used for Aβ40 determination (Wako ELISA: ("Human/Rat β Amyloid (40) ELISA kit Wako II" ; cat nr. 294-64701) following the manufacture's instruction. Also here the Aβ-lowering efficacy was calculated as percentage of the vehicle group.

TABLE 1

| Ex. | Structure | BACE1 cell act. Aβ40 $IC_{50}$ [nM] | Aβ40 (wt mice, brain) [%] |
|---|---|---|---|
| 1 | (structure shown) | 0.2 | 62 | which is

TABLE 1-continued

Pharmacological data

| Ex. | Structure | BACE1 cell act. Aβ40 IC$_{50}$ [nM] | Aβ40 (wt mice, brain) [%] |
|---|---|---|---|
| | (structure) or (structure) | | |
| 2 | (structure) | 0.2 | 48 |
| 3 | (structure) | 13.8 | 95 |
| 4 | (structure) | 0.4 | 83 |

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 5 | | 0.8 | 88 |
| 6 | | 218 | — |

TABLE 1-continued

Pharmacological data

| Ex. | Structure | BACE1 cell act. Aβ40 IC$_{50}$ [nM] | Aβ40 (wt mice, brain) [%] |
| --- | --- | --- | --- |
| 7 | | 46 | — |
| | which is | | |
| | or | | |
| 8 | 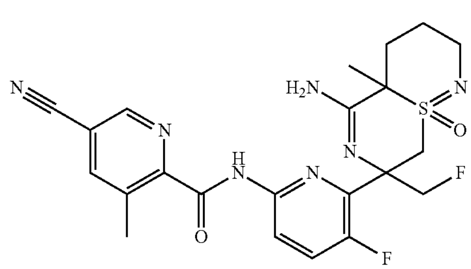 [SMILES: Cc1cc(C#N)cnc1C(=O)Nc1ccc(F)c(C2(CF)CS3(=O)=NCCCC3(C)C(N)=N2)n1] | >200 | — |
| | which is | | |

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 9 | | 98 | 113 | which is or

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 10 | | 2.9 | 89 | which is or

| 11 | | 2.3 | 90 | which is or

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 12 | | 320 | 77 |
| 13 | 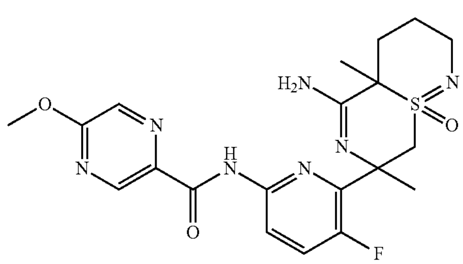 [SMILES: COc1cnc(C(=O)Nc2ccc(F)c(C3(C)CS4(=O)=NCCCC4(C)C(N)=N3)n2)cn1] | — | — |

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 14 | 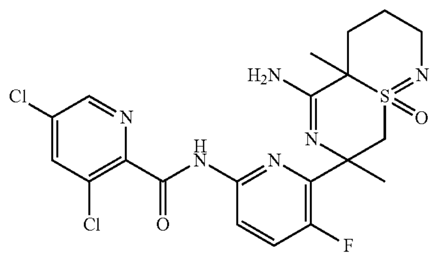 [SMILES: CC1(c2nc(NC(=O)c3ncc(Cl)cc3Cl)ccc2F)CS2(=O)=NCCCC2(C)C(N)=N1] | — | — |
| 15 | 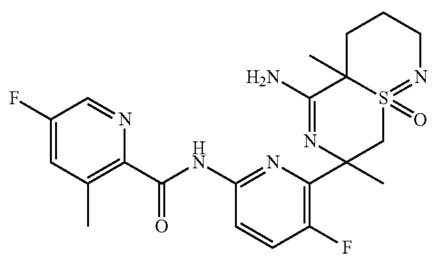 [SMILES: Cc1cc(F)cnc1C(=O)Nc1ccc(F)c(C2(C)CS3(=O)=NCCCC3(C)C(N)=N2)n1] | — | — |
| 16 | 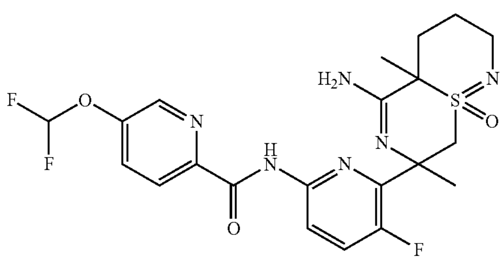 [SMILES: CC1(c2nc(NC(=O)c3ccc(OC(F)F)cn3)ccc2F)CS2(=O)=NCCCC2(C)C(N)=N1] | — | — |
| 17 | 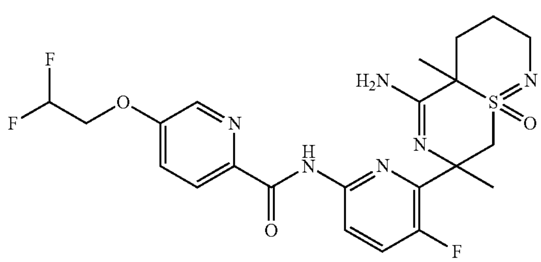 [SMILES: CC1(c2nc(NC(=O)c3ccc(OCC(F)F)cn3)ccc2F)CS2(=O)=NCCCC2(C)C(N)=N1] | — | — |
| 18 | 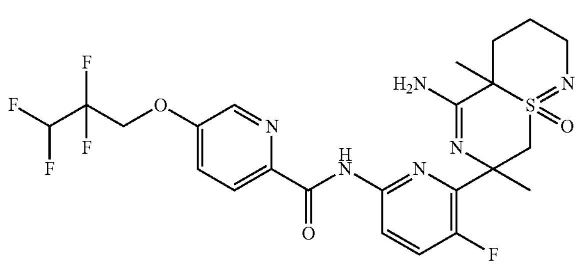 [SMILES: CC1(c2nc(NC(=O)c3ccc(OCC(F)(F)C(F)F)cn3)ccc2F)CS2(=O)=NCCCC2(C)C(N)=N1] | — | — |

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 19 | 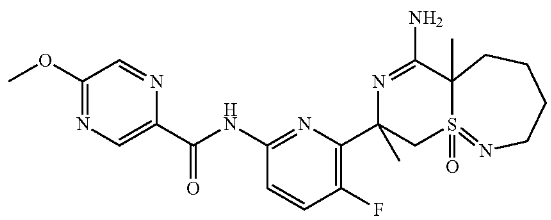 [SMILES: COc1cnc(C(=O)Nc2ccc(F)c(C3(C)CS4(=O)=NCCCCC4(C)C(N)=N3)n2)cn1] | — | — |
| 20 | 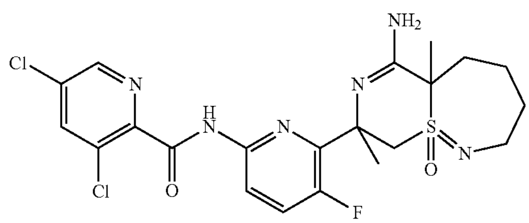 [SMILES: CC1(c2nc(NC(=O)c3ncc(Cl)cc3Cl)ccc2F)CS2(=O)=NCCCCC2(C)C(N)=N1] | — | — |
| 21 | 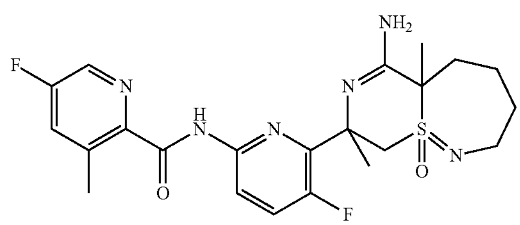 [SMILES: Cc1cc(F)cnc1C(=O)Nc1ccc(F)c(C2(C)CS3(=O)=NCCCCC3(C)C(N)=N2)n1] | — | — |
| 22 | 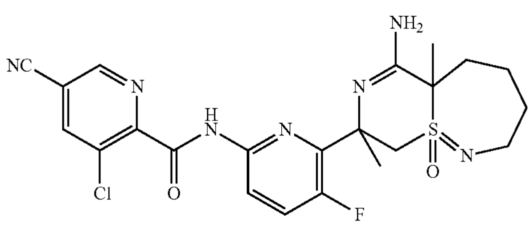 [SMILES: CC1(c2nc(NC(=O)c3ncc(C#N)cc3Cl)ccc2F)CS2(=O)=NCCCCC2(C)C(N)=N1] | — | — |
| 23 | 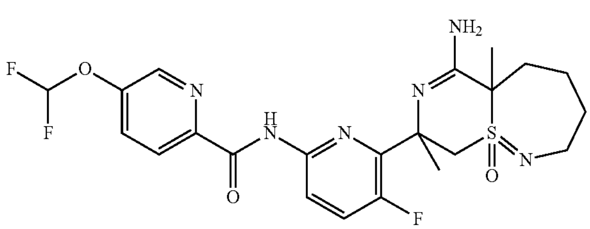 [SMILES: CC1(c2nc(NC(=O)c3ccc(OC(F)F)cn3)ccc2F)CS2(=O)=NCCCCC2(C)C(N)=N1] | — | — |
| 24 | 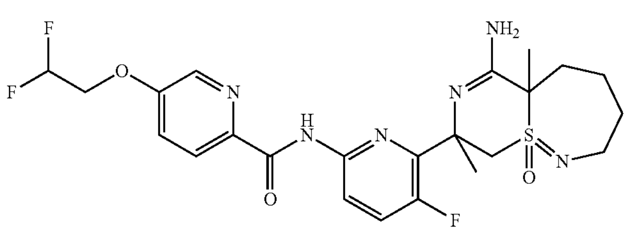 [SMILES: CC1(c2nc(NC(=O)c3ccc(OCC(F)F)cn3)ccc2F)CS2(=O)=NCCCCC2(C)C(N)=N1] | — | — |

TABLE 1-continued

Pharmacological data

| Ex. | Structure | BACE1 cell act. Aβ40 IC$_{50}$ [nM] | Aβ40 (wt mice, brain) [%] |
|---|---|---|---|
| 25 | (structure) | — | — |

Pharmaceutical Compositions

The compounds of formula I and the pharmaceutically acceptable salts can be used as therapeutically active substances, e.g. in the form of pharmaceutical preparations. The pharmaceutical preparations can be administered orally, e.g. in the form of tablets, coated tablets, dragees, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also provided by the present invention, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, particularly 1-100 mg, of a compound of formula I. Examples of compositions according to the invention are:

EXAMPLE A

Tablets of the following composition are manufactured in the usual manner

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |

TABLE 3-continued possible capsule ingredient composition

| ingredient | mg/capsule | | | |
|---|---|---|---|---|
| | 5 | 25 | 100 | 500 |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure

1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

Intermediate of Formula X

2-Bromo-5-fluoro-4-(triethylsilyl)pyridine

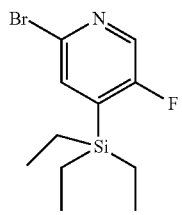

To a solution of diisopropylamine (130 g, 183 ml, 1.28 mol) in tetrahydrofuran (1500 ml) was added 1.6 M n-butyllithium in tetrahydrofuran (800 ml, 1.28 mol) at −20° C. The reaction mixture was allowed to warm to 0° C. and stirred for additional 30 minutes. A solution consisting of 2-bromo-5-fluoropyridine (205 g, 1.16 mol) in tetrahydrofuran (200 ml) was added at −70° C. After 60 minutes triethylchlorosilane (193 g, 217 ml, 1.28 mol) was added drop wise in 30 minutes. Stirring was continued for 1 h at −70° C. and then allowed to warm to −30° C. The reaction mixture was poured onto a mixture of 1 M aqueous hydrogen chloride solution (1000 ml) and 13-% aqueous ammonium chloride solution. The layers were separated. The aqueous layer was extracted with tert-butyl methyl ether (2000 ml). The combined organic layers were washed with one 1500-ml portion of water and concentrated in vacuo to give the crude title compound (345 g, quantitative) as orange oil, which was used in the next step without further purification. MS m/e: 290, 292 ([M+H]$^+$).

Intermediate of Formula XI 1-(6-Bromo-3-fluoro-4-(triethylsilyl)pyridin-2-yl)ethanone

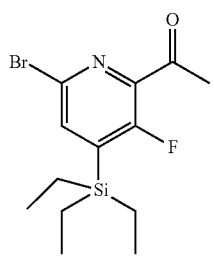 [SMILES: CC[Si](CC)(CC)c1cc(Br)nc(C(C)=O)c1F]

To a solution of diisopropylamine (160 g, 225 ml, 1.55 mol) in tetrahydrofuran (2200 ml) was added 1.6 M n-butyllithium in tetrahydrofuran (950 ml, 1.52 mol) at −20° C. The reaction mixture was allowed to warm to 0° C. and stirred for additional 30 minutes. A solution of 2-bromo-5-fluoro-4-(triethylsilyl)pyridine (338 g, 1.16 mol) in tetrahydrofuran (300 ml) was added drop wise in 30 minutes at −70° C. After 80 minutes N,N-dimethylacetamide (107 g, 115 ml, 1.22 mol) was added drop wise in 10 minutes. The cooling bath was removed and the reaction mixture was poured onto a mixture of 25-% aqueous hydrogen chloride solution (255 g, 227 ml, 1.75 mol), 10-% aqueous sodium chloride solution (2500 ml). The layers were separated. The aqueous layer was extracted with tert-butyl methyl ether (2500 ml). The combined organic layers were concentrated in vacuo to give the crude title compound (392 g, quantitative) as dark brown viscous oil, which was used in the next step without further purification. MS m/e: 332, 334 ([M+H]$^+$).

Intermediate of Formula XXXV 1-(6-Bromo-3-fluoro-4-(triethylsilyl)pyridin-2-yl)-2-fluoroethanone

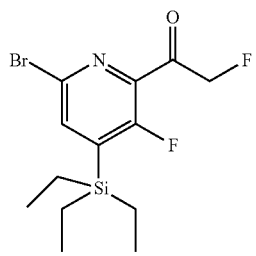 [SMILES: CC[Si](CC)(CC)c1cc(Br)nc(C(=O)CF)c1F]

To a solution of diisopropylamine (3.83 g, 5.4 ml, 37.9 mmol, Eq: 1.1) in tetrahydrofuran (70 ml) was added n-butyllithium, 1.6 M in n-hexanes (23.7 ml, 37.9 mmol, Eq: 1.1) at −40° C. The dry ice/acetone bath was removed and stirring was continued for 20 min at −10° C. Addition of 2-bromo-5-fluoro-4-(triethylsilyl)pyridine (10 g, 34.5 mmol, Eq: 1) as a solution in tetrahydrofuran (10 ml) at −70° C. Stirring was continued for 30 minutes. Addition of methyl 2-fluoroacetate (3.25 ml, 41.3 mmol, Eq: 1.2). Stirring was continued for 30 minutes. The reaction was quenched with saturated ammonium chloride solution (20 ml) at −40° C. The cooling bath was removed and stirring was continued for 45 minutes. The reaction mixture was partitioned between TBME (50 ml) and saturated ammonium chloride solution (50 ml). The layers were separated. The aqueous layer was extracted with one 100-ml portion of TBME. The combined organic layers were washed with one 50-ml portion of brine, dried over anhydrous sodium sulfate, filtered and concentrated in vacuo to give the crude title compound which was used in the next step without further purification. MS m/e: 350, 352 ([M+H]$^+$).

Ketimine of Formula XII (R,E)-N-(1-(6-bromo-3-fluoro-4-(triethylsilyl)pyridin-2-yl)ethylidene)-2-methylpropane-2-sulfinamide

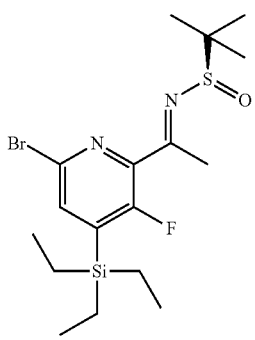 [SMILES: CC[Si](CC)(CC)c1cc(Br)nc(/C(C)=N/[S@](=O)C(C)(C)C)c1F]

To a mixture of 1-(6-bromo-3-fluoro-4-(triethylsilyl)pyridin-2-yl)ethanone (200 g, 512 mmol) and (R)-2-methylpropane-2-sulfinamide (77.5 g, 640 mmol) in ethyl acetate (2000 ml) was added titanium (IV) ethoxide (187 g, 171 ml, 819 mmol). The reaction mixture was heated at 60° C. and stirred overnight. The heating bath was removed and the excess of titanium (IV) ethoxide was quenched by addition of water (24.0 g, 24 ml, 1.33 mol) at 40° C. The solids were removed by filtration and washed with two 500 -ml portions of water. The filtrate was washed with one 1000 -ml portion of 5-% aqueous hydrogen chloride solution and one 5-% aqueous sodium hydrogencarbonate solution. The organic layer was dried over anhydrous sodium sulfate, filtrated and concentrated in vacuo. Purification by flash-chromatography with n-heptane/ethyl acetate as eluent gave the title compound as brown viscous oil. MS m/e: 435, 437 ([M+H]$^+$).

Ketimine of Formula XXXVI (R,E)-N-(1-(6-Bromo-3-fluoro-4-(triethylsilyl)pyridin-2-yl)-2-fluoroethylidene)-2-methylpropane-2-sulfinamide

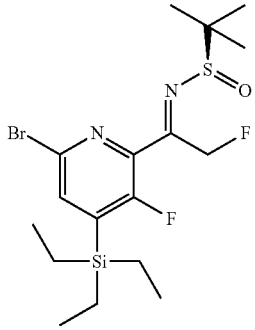 [SMILES: CC[Si](CC)(CC)c1cc(Br)nc(/C(CF)=N/[S@](=O)C(C)(C)C)c1F]

To a mixture of 1-(6-bromo-3-fluoro-4-(triethylsilyl)pyridin-2-yl)-2-fluoroethanone (11.9 g, 34 mmol, Eq: 1) and (R)-2-methylpropane-2-sulfinamide (5.35 g, 44.2 mmol, Eq: 1.3) in ethyl acetate (136 ml) was added titanium(IV) ethoxide (12.4 g, 11.4 ml, 54.4 mmol, Eq: 1.6) at RT. The reaction mixture was heated at 50° C. (Heat-on plate of 50° C.) for 6 h. The heating bath was replaced by a cold water bath and stirring was continued for 5 min. Addition of water (1.59 g, 1.59 ml, 88.3 mmol, Eq: 2.6). Stirring was continued for 1 h. A brown precipitate was formed. The solids were removed by filtration and washed with three 50-ml portions of ethyl acetate. The filtrate was washed with one 100-ml portion of water/brine (1:1) and one 100-ml portion of brine, dried over anhydrous sodium sulfate, filtered and concentrated in vacuo. The crude material was purified by flash chromatography with n-heptane/ethyl acetate as eluent to give the title compound (7.2 g, 47%) as light brown viscous oil. MS m/e: 453, 455 ([M+H]$^+$).

Intermediates of Formula III 2-(Methylthio)propanenitrile

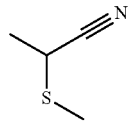

To a solution of 2-chloropropanenitrile (20.2 g, 20 ml, 215 mmol) in acetonitrile (107 ml) was added in small portions sodium thiomethoxide (19.6 g, 279 mmol) at 0-5° C. The cooling bath was removed after the addition and the reaction mixture was heated at reflux for 60 minutes. The heating bath was removed and stirring was continued for 15 h. After 30 minutes a 100-ml portion of tert-butyl methyl ether was added. The solids were removed by filtration and washed with tert-butyl methyl ether. The filtrate was concentrated in vacuo. The residue was triturated in tert-butyl methyl ether (50 ml). The solids were removed by filtration. The filtrate was concentrated in vacuo to give the title compound (21.7 g, quantitative) as light brown oil, which was used in the next step without further purification. MS m/e: 101 ([M]$^+$).

Intermediates of Formula IV

5-Chloro-2-methyl-2-(methylthio)pentanenitrile

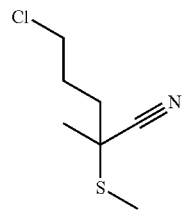

To a solution of 2-(methylthio)propanenitrile (10.0 g, 98.8 mmol) in tetrahydrofuran (99 ml) was added 1.0 M solution lithium bis(trimethylsilyl)amide in tetrahydrofuran/ethylbenzene (109 ml, 109 mmol) at −15 to −10° C. After 1 h, 1-chloro-3-iodopropane (22.2 g, 11.5 ml, 109 mmol) was added in a quick fashion. The cooling bath was removed after the addition and stirring was continued for 2 h. The reaction mixture was partitioned between tert-butyl methyl ether (100 ml) and aqueous saturated ammonium chloride solution (50 ml). The layers were separated. The organic layer was washed with one 100-ml portion of aqueous saturated ammonium chloride solution and one 100 -ml portion of brine, dried over anhydrous sodium sulfate, filtered and concentrated in vacuo. Purification by flash-chromatography with n-heptane/ethyl acetate as eluent gave the title compound (12.4 g, 71%) as light yellow oil. MS m/e: 177 ([M]+).

Sulfoxide intermediates of Formula V

5-Chloro-2-methyl-2-(methylsulfinyl)pentanenitrile

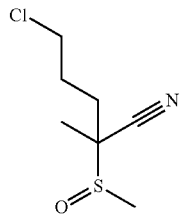

To a solution of 5-chloro-2-methyl-2-(methylthio)pentanenitrile (12.4 g, 69.8 mmol) in 1,4-dioxane (70 ml)/water (140 ml) was added sodium periodate (14.9 g, 69.8 mmol). The reaction mixture was stirred for 4 h. Addition of further sodium periodate (1.49 g, 6.98 mmol) in one portion. The reaction mixture was stirred for 2 h. The solids were removed by filtration and washed with tetrahydrofuran. The solvent was evaporated. The aqueous residue was partitioned between ethyl acetate (100 ml) and brine (100 ml). The layers were separated. The aqueous layer was extracted with two 100-ml portions of ethyl acetate. The combined organic layers were washed with one 100-ml portion of brine, dried over anhydrous sodium sulfate, filtered and concentrated in vacuo to give the crude title compound (13.7 g, quantitative) as orange viscous oil, which was used in the next step without further purification. MS m/e: 194 ([M+H]+).

Intermediates of Formula VI

N-[(5-chloro-2-cyanopentan-2-yl)(methyl)oxido$\lambda^6$-sulfanylidene]-2,2,2-trifluoroacetamide

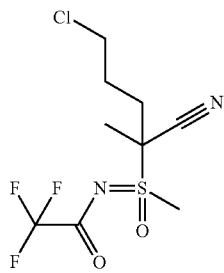 [SMILES: CC(C#N)(CCCCl)S(C)(=O)=NC(=O)C(F)(F)F]

To a suspension of 5-chloro-2-methyl-2-(methylsulfinyl)pentanenitrile (13.4 g, 69.2 mmol), 2,2,2-trifluoroacetamide (15.6 g, 138 mmol), magnesium oxide (11.4 g, 277 mmol) and rhodium (II) acetate dimer (0.764 g, 1.73 mmol) in dichloromethane (692 ml) was added iodobenzene diacetate (33.4 g, 104 mmol). The reaction mixture was stirred for 72 h. The solids were removed by filtration and washed with dichloromethane. The solvent was evaporated. Purification by flash-chromatography with n-heptane/ethyl acetate as eluent gave the title compound (7.1 g, 34%) as brown viscous oil. MS m/e: 303 ([M–H]+).

Intermediate of Formula VIII-a trans-1,6-Dimethyl-3,4,5,6-tetrahydro-1,2-thiazine-6-carbonitrile 1-oxide

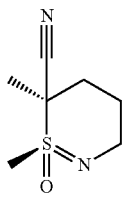

and

Intermediate of Formula VIII-b cis-1,6-Dimethyl-3,4,5,6-tetrahydro-1,2-thiazine-6-carbonitrile 1-oxide

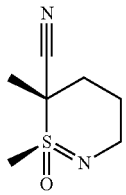

To a solution of N-[(5-chloro-2-cyanopentan-2-yl)(methyl)oxido$\lambda^6$-sulfanylidene]-5 2,2,2- (11.5 g, 37.7 mmol, Eq: 1) in methanol (126 ml) was added potassium carbonate (26.1 g, 189 mmol, Eq: 5) in small portions at 0-5° C. Stirring was continued for 1 h. The reaction mixture was diluted with TBME (100 ml) and stirred for 10 minutes. The solids were removed by filtration over Decalite and washed with methanol/TBME (150 ml). The filtrate was concentrated in vacuo. The residue was partitioned between dichloromethane (100 ml) and 1 M sodium carbonate (50 ml). The layers were separated. The aqueous layer was extracted with two 100-ml portions of dichloromethane. The combined organic layers were dried over anhydrous sodium sulfate, filtered and concentrated in vacuo to give a mixture of the uncyclized intermediate, trans-1,6-dimethyl-3,4,5,6-tetrahydro-1,2-thiazine-6-carbonitrile 1-oxide and cis-1,6-dimethyl-3,4,5,6-tetrahydro-1,2-thiazine-6-carbonitrile 1-oxide. The product mixture, a catalytical amount of tetrabutylammonium iodide and cesium carbonate (24.6 g, 75.5 mmol, Eq: 2) in acetonitrile (126 ml) was heated at 70° C. and stirred for 3 d. The solvent was evaporated. The residue was partitioned between ethyl acetate (100 ml) and water/brine (1:1) (100 ml). The layers were separated. The aqueous layer was extracted with two 100-ml portions of ethyl acetate. The combined organic layers were washed with one 50-ml portion of brine, dried over anhydrous sodium sulfate, filtered and concentrated in vacuo. The crude material was purified by flash chromatography with n-heptane/ethyl acetate as eluent to give trans-1,6-dimethyl-3,4,5,6-tetrahydro-1,2-thiazine-6-carbonitrile 1-oxide and cis-1,6-dimethyl-3,4,5,6-tetrahydro-1,2-thiazine-6-carbonitrile 1-oxide.

trans-1,6-Dimethyl-3,4,5,6-tetrahydro-1,2-thiazine-6-carbonitrile 1-oxide was obtained as light yellow solid in 48% yield. MS m/e: 173 ([M+H]$^+$).

cis-1,6-Dimethyl-3,4,5,6-tetrahydro-1,2-thiazine-6-carbonitrile 1-oxide was obtained as light yellow solid in 22% yield. MS m/e: 173 ([M+H]$^+$).

Intermediates of Formula XIII

General Procedure I: Ketimine Addition

To a solution of an intermediate of formula VIII in dry dichloromethane (0.3 M) is added a commercially available 1M lithium bis(trimethylsilyl)amide solution in tetrahydrofuran/ethylbenzene (1.3 eq) at −60° C. The reaction mixture is stirred for 1 h. A solution of a ketimine intermediate of formula XII or XXXVI in dry dichloromethane (0.5 M) is added dropwise. The reaction mixture is quenched with aqueous saturated ammonium chloride solution after 1-3 h and extracted with two or three portions of an organic solvent such as Cert-butyl methyl ether or dichloromethane. The combined organic layers are dried over anhydrous sodium sulfate and concentrated to dryness. Purification by flash-chromatography gives an intermediate of formula XIII.

Intermediate of Formula XIII-a (R)—N—(R)-2-(6-Bromo-3-fluoro-4-(triethylsilyp-pyridin-2-yl)-1-((1S,6S)-6-cyano-6-methyl-1-oxido-3,4,5,6-tetrahydro-1,2-thiazin-1-yl)propan-2-yl)-2-methylpropane-2-sulflnamide (or diastereomer)

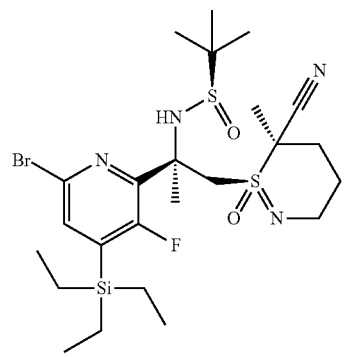 [SMILES: CC[Si](CC)(CC)c1cc(Br)nc([C@](C)(C[S@]2(=O)=NCCC[C@]2(C)C#N)N[S@](=O)C(C)(C)C)c1F]

and

Intermediate of Formula XIII-b (R)—N—(R)-2-(6-Bromo-3-fluoro-4-(triethylsilyp-pyridin-2-yl)-1-((1R,6R)-6-cyano-6-methyl-1-oxido-3,4,5,6-tetrahydro-1,2-thiazin-1-yl)propan-2-yl)-2-methylpropane-2-sulflnamide (or diastereomer)

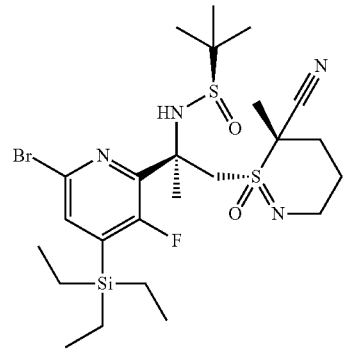 [SMILES: CC[Si](CC)(CC)c1cc(Br)nc([C@](C)(C[S@@]2(=O)=NCCC[C@@]2(C)C#N)N[S@](=O)C(C)(C)C)c1F]

The title compounds were prepared according the general procedure I from trans-(1R,6R)-1,6-dimethyl-3,4,5,6-tetrahydro-1,2-thiazine-6-carbonitrile1-oxide and (R,E)-N-(1-(6-bromo-3-fluoro-4-(triethylsilyl)pyridin-2-yl)ethylidene)-2-methylpropane-2-sulfinamide. Purification by flash-chromatography with n-heptane/ethyl acetate as eluent gave (R)—N—((R)-2-(6-Bromo-3-fluoro-4-(triethylsilyl)pyridin-2-yl)-1-((1S,6S)-6-cyano-6-methyl-1-oxido-3,4,5,6-tetrahydro-1,2-thiazin-1-yl)propan-2-yl)-2-methylpropane-2-sulfinamide (or diastereomer) and (R)—N—((R)-2-(6-bromo-3-fluoro-4-(triethylsilyl)pyridin-2-yl)-1-((1R,6R)-6-cyano-6-methyl-1-oxido-3,4,5,6-tetrahydro-1,2-thiazin-1-yl)propan-2-yl)-2-methylpropane-2-sulfinamide (or diastereomer).

(R)—N—((R)-2-(6-Bromo-3-fluoro-4-(triethylsilyl)pyridin-2-yl)-1-((1S,6S)-6-cyano-6-methyl-1-oxido-3,4,5,6-tetrahydro-1,2-thiazin-1-yl)propan-2-yl)-2-methylpropane-2-sulfinamide (or diastereomer) was obtained as light yellow solid in 58% yield. MS m/e: 607, 609 ([M+H]$^+$).

(R)—N—((R)-2-(6-bromo-3-fluoro-4-(triethylsilyl)pyridin-2-yl)-1-((1R,6R)-6-cyano-6-methyl-1-oxido-3,4,5,6-tetrahydro-1,2-thiazin-1-yl)propan-2-yl)-2-methylpropane-2-sulfinamide (or diastereomer) was obtained as light yellow solid in 25% yield. MS m/e: 607, 609 ([M+H]$^+$).

75

Intermediate of Formula XIII-e and

Intermediate of Formula XIII-f (R)—N-((2S)-2-(6-bromo-3-fluoro-4-(triethylsilyp-pyridin-2-yl)-1-((1S,6S)-6-cyano-6-methyl-1-oxido-3,4,5,6-tetrahydro-1,2-thiazin-1-yl)-3-fluoropropan-2-yl)-2-methylpropane-2-sulfinamide and (R)—N-(2S)-2-(6-bromo-3-fluoro-4-(triethylsilyp-pyridin-2-yl)-1-((1R,6R)-6-cyano-6-methyl-1-oxido-3,4,5,6-tetrahydro-1,2-thiazin-1-yl)-3-fluoropropan-2-yl)-2-methylpropane-2-sulfinamide

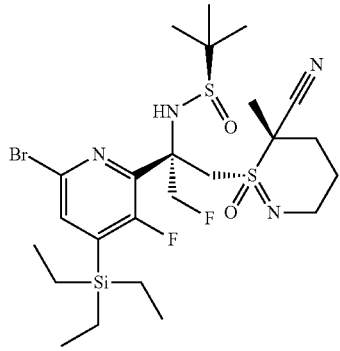

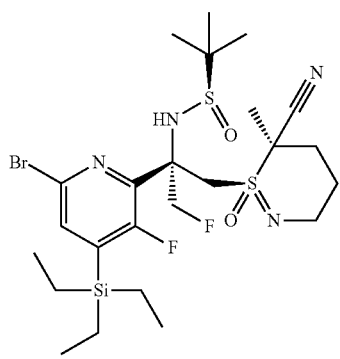

The title compound mixture was prepared according the general procedure I from trans-(1R,6R)-1,6-dimethyl-3,4,5,6-tetrahydro-1,2-thiazine-6-carbonitrile 1-oxide and (R,E)-N-(1-(6-bromo-3-fluoro-4-(triethylsilyl)pyridin-2-yl)-2-fluoroethylidene)-2-methylpropane-2-sulfinamide. Purification by flash-chromatography with n-heptane/ethyl acetate as eluent gave a mixture of the title compounds (3.3 g, 60%) as light yellow viscous oil. MS m/e: 625, 627 ([M+H]+).

76

Intermediate of Formula XIII-g (R)—N—((S)-2-(6-bromo-3-fluoro-4-(triethylsilyp-pyridin-2-yl)-1-((1R,6S)-6-cyano-6-methyl-1-oxido-3,4,5,6-tetrahydro-1,2-thiazin-1-yl)-3-fluoropropan-2-yl)-2-methylpropane-2-sulfinamide (or diastereomer)

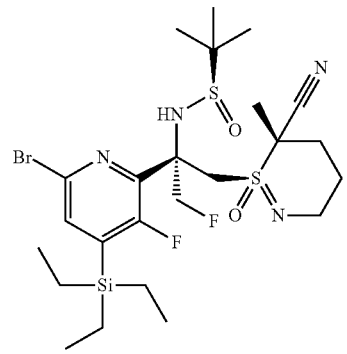 [SMILES: CC[Si](CC)(CC)c1cc(Br)nc([C@](CF)(C[S@]2(=O)=NCCC[C@@]2(C)C#N)N[S@](=O)C(C)(C)C)c1F]

and

Intermediate of Formula XIII-h (R)—N—((S)-2-(6-bromo-3-fluoro-4-(triethylsilyp-pyridin-2-yl)-1-((1S,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer)

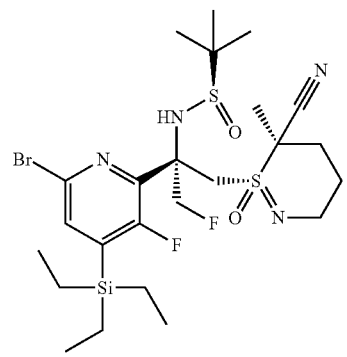 [SMILES: CC[Si](CC)(CC)c1cc(Br)nc([C@](CF)(C[S@@]2(=O)=NCCC[C@]2(C)C#N)N[S@](=O)C(C)(C)C)c1F]

The title compounds were prepared according the general procedure I from cis (1R,6S)-1,6-dimethyl-3,4,5,6-tetrahydro-1,2-thiazine-6-carbonitrile 1-oxide and (R,E)-N-(1-(6-bromo-3-fluoro-4-(triethylsilyl)pyridin-2-yl)-2-fluoroethylidene)-2-methylpropane-2-sulfinamide. Purification by flash-chromatography with n-heptane/ethyl acetate as eluent gave (R)—N—((S)-2-(6-bromo-3-fluoro-4-(triethylsilyl)pyridin-2-yl)-1-((l1R,6 S)-6-cyano-6-methyl-1-oxido-3,4,5,6-tetrahydro-1,2-thiazin-1-yl)-3-fluoroprop an-2-yl)-2-methylprop ane-2-sulfinamide (or diastereomer) and (R)—N—((S)-2-(6-bromo-3-fluoro-4-(triethylsilyl)pyridin-2-yl)-1-((1S,6R)-6-cyano-6-methyl-1-oxido-3,4,5,6-tetrahydro-1, 2-thiazin-1-yl)-3-fluoropropan-2-yl)-2-methylpropane-2-sulfinamide (diastereomer b) (or enantiomer).

(R)—N—((S)-2-(6-bromo-3-fluoro-4-(triethylsilyl)pyridin-2-yl)-1-((1R,6S)-6-cyano-6-methyl-1-oxido-3,4,5,6-tetrahydro-1,2-thiazin-1-yl)-3-fluoropropan-2-yl)-2-methylpropane-2-sulfinamide (or diastereomer) was obtained as light yellow amorphous solid in 27% yield. MS m/e: 625, 627 ([M+H]$^+$).

(R)—N—((S)-2-(6-bromo-3-fluoro-4-(triethylsilyl)pyridin-2-yl)-1-((1S,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer) was obtained as light yellow viscous oil in 27% yield. MS m/e: 625, 627 ([M+H]$^+$).

Intermediates of Formula XXXVII

General Procedure II: TES-deprotection

To a solution of an intermediate of formula XIII in a mixture of tetrahydrofuran and N,N-dimethylformamide (1:1, 0.3 M) is added potassium fluoride (2 eq) and acetic acid (2 eq) at RT. The reaction mixture is stirred for 2-24 h. The reaction mixture is partitioned between 1 M aqueous sodium bicarbonate solution and a solvent such as ethyl acetate. The layers are separated. The aqueous layer is extracted with one or two portions of an organic solvent such as ethyl acetate. The combined organic layers are dried over anhydrous sodium sulfate and concentrated to dryness. Purification by flash-chromatography gives an intermediate of formula XXXVII.

Intermediate of Formula XXXVII-a (R)—N—(R)-2-(6-bromo-3-fluoropyridin-2-yl)-1-((1S,6S)-6-cyano-6-methyl-1-oxido-3,4,5,6-tetrahydro-1,2-thiazin-1-yl)propan-2-yl)-2-methylpropane-2-sulfinamide (or diastereomer)

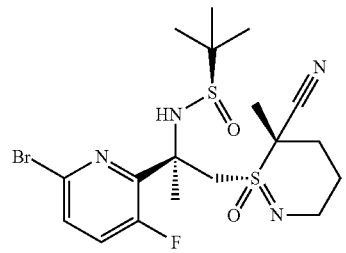 [SMILES: CC(C)(C)[S@@](=O)N[C@@](C)(C[S@@]1(=O)=NCCC[C@@]1(C)C#N)c1nc(Br)ccc1F]

The title compound was obtained as off-white solid in 95% yield according the general procedure II from (R)—N—((R)-2-(6-bromo-3-fluoro-4-(triethylsilyl)pyridin-2-yl)-1-((1S,6S)-6-cyano-6-methyl-1-oxido-3,4,5,6-tetrahydro-1,2-thiazin-1-yl)propan-2-yl)-2-methylpropane-2-sulfinamide (or diastereomer). MS m/e: 493, 495 ([M+H]$^+$).

Intermediate of Formula XXXVII-b (R)—N—(R)-2-(6-bromo-3-fluoropyridin-2-yl)-1-((1R,6R)-6-cyano-6-methyl-1-oxido-3,4,5,6-tetrahydro-1,2-thiazin-1-yl)propan-2-yl)-2-methylpropane-2-sulfinamide (or diastereomer)

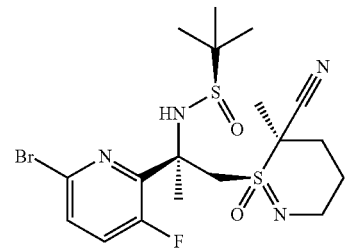 [SMILES: CC(C)(C)[S@@](=O)N[C@@](C)(C[S@]1(=O)=NCCC[C@]1(C)C#N)c1nc(Br)ccc1F]

The title compound was obtained as off-white solid in 92% yield according the general procedure II from (R)—N4R)-2-(6-bromo-3-fluoro-4-(triethylsilyl)pyridin-2-yl)-1-((1R,6R)-6-cyano-6-methyl-1-oxido-3,4,5,6-tetrahydro-1,2-thiazin-1-yl)propan-2-yl)-2-methylpropane-2-sulfinamide (or diastereomer). MS m/e: 493, 495 ([M+H]$^+$).

Intermediate of Formula XXXVII-e (R)—N—((S)-2-(6-bromo-3-fluoropyridin-2-yl)-1-((1S,6S)-6-cyano-6-methyl-1-oxido-3,4,5,6-tetrahydro-1,2-thiazin-1-yl)-3-fluoropropan-2-yl)-2-methylpropane-2-sulfinamide (or diastereomer)

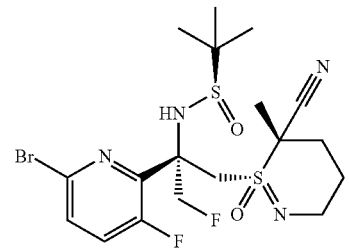 [SMILES: CC(C)(C)[S@@](=O)N[C@@](CF)(C[S@@]1(=O)=NCCC[C@@]1(C)C#N)c1nc(Br)ccc1F]

and

Intermediate of Formula XXXVII-f (R)—N—((S)-2-(6-bromo-3-fluoropyridin-2-yl)-1-
((1R,6R)-6-cyano-6-methyl-1-oxido-3,4,5,6-tetra-
hydro-1,2-thiazin-1-yl)-3-fluoropropan-2-yl)-2-
methylpropane-2-sulfinamide (or diastereomer)

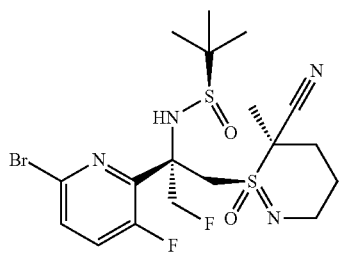 [SMILES: CC(C)(C)[S@@](=O)N[C@@](CF)(C[S@]1(=O)=NCCC[C@]1(C)C#N)c1nc(Br)ccc1F]

The title compounds were obtained according the general procedure II from (R)—N—((2S)-2-(6-bromo-3-fluoro-4-(triethylsilyl)pyridin-2-yl)-1-(6-cyano-6-methyl-1-oxido-3,4,5,6-tetrahydro-1,2-thiazin-1-yl)-3-fluoropropan-2-yl)-2-methylpropane-2-sulfinamide.

(R)—N—((S)-2-(6-bromo-3-fluoropyridin-2-yl)-1-((1S,6S)-6-cyano-6-methyl-1-oxido-3,4,5,6-tetrahydro-1,2-thiazin-1-yl)-3-fluoroprop an-2-yl)-2-methylpropane-2-sulfinamide (or diastereomer) was obtained as white solid in 23% yield with an ee-purity of 80%. MS m/e: 511, 513 ([M+H]$^+$).

(R)—N—((S)-2-(6-bromo-3-fluoropyridin-2-yl)-1-((1R,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer) was obtained as light red solid in 70% yield with an ee-purity of 100%. MS m/e: 511, 513 ([M+H]$^+$).

Intermediate of Formula XXXVII-g (R)—N—((S)-2-(6-bromo-3-fluoropyridin-2-yl)-1-((1R,6S)-6-cyano-6-methyl-1-oxido-3,4,5,6-tetrahydro-1,2-thiazin-1-yl)-3-fluoropropan-2-yl)-2-methylpropane-2-sulfinamide (or diastereomer)

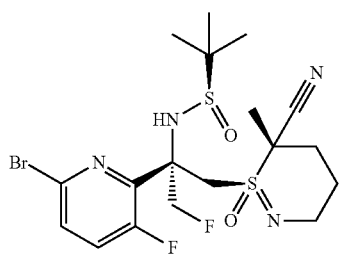 [SMILES: CC(C)(C)[S@@](=O)N[C@@](CF)(C[S@]1(=O)=NCCC[C@@]1(C)C#N)c1nc(Br)ccc1F]

The title compound was obtained as light brown viscous oil in quantitative yield according the general procedure II from (R)—N—((S)-2-(6-bromo-3-fluoro-4-(triethylsilyl) pyridin-2-yl)-1-((1R,6S)-6-cyano-6-methyl-1-oxido-3,4,5, 6-tetrahydro-1,2-thiazin-1-yl)-3-fluoropropan-2-yl)-2-methylpropane-2-sulfinamide (or diastereomer). MS m/e: 511, 513 ([M+H]$^+$).

Intermediate of Formula XXXVII-h (R)—N—((S)-2-(6-bromo-3-fluoropyridin-2-yl)-1-((1S,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer)

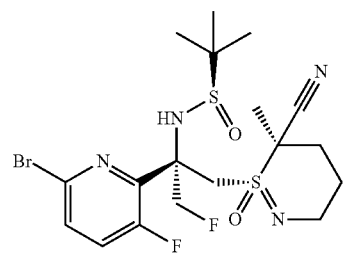 [SMILES: CC(C)(C)[S@@](=O)N[C@@](CF)(C[S@@]1(=O)=NCCC[C@]1(C)C#N)c1nc(Br)ccc1F]

The title compound was obtained as brown viscous oil in quantitative yield according the general procedure II from (R)—N—((S)-2-(6-bromo-3-fluoro-4-(triethylsilyl)pyridin-2-yl)-1-((1S,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer). MS m/e: 511, 513 ([M+H]$^+$).

Intermediates of Formula XXVIII

General Procedure III: Sulfinamide Hydrolyzation

To a solution of an intermediate of formula XXXVII in methanol (0.5 M) is added 4M hydrogen chloride solution in 1,4-dioxane (10 eq) at 0-5° C. Stirring is continued for 30-90 minutes. The reaction mixture is partitioned between 1 M aqueous sodium carbonate solution and a solvent such as ethyl acetate. The layers are separated. The aqueous layer is extracted with one or two portions of an organic solvent such as ethyl acetate. The combined organic layers are dried over anhydrous sodium sulfate and concentrated to dryness. Purification by flash-chromatography gives an intermediate of formula XXXVIII.

Intermediate of Formula XXVIII-a (1S,6S)-14(R)-2-Amino-2-(6-bromo-3-fluoropyridin-2-yl)propyl)-6-methyl-3,4,5,6-tetrahydro-1,2-thiazine-6-carbonitrile 1-oxide (or diastereomer)

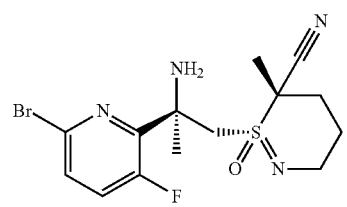 [SMILES: C[C@](N)(C[S@@]1(=O)=NCCC[C@@]1(C)C#N)c1nc(Br)ccc1F]

The title compound was obtained as light yellow solid in 93% yield according the general procedure III from (R)—

N—((R)-2-(6-bromo-3-fluoropyridin-2-yl)-1-((1S,6S)-6-cyano-6-methyl-1-oxido-3,4,5,6-tetrahydro-1,2-thiazin-1-yl)propan-2-yl)-2-methylpropane-2-sulfinamide (or diastereomer). MS m/e: 389, 391 ([M+H]+).

Intermediate of Formula XXVIII-b (1R,6R)-14(R)-2-amino-2-(6-bromo-3-fluoropyridin-2-yl)propyl)-6-methyl-3,4,5,6-tetrahydro-1,2-thiazine-6-carbonitrile 1-oxide (or diastereomer)

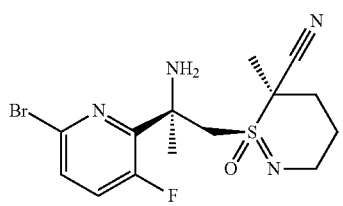 [SMILES: C[C@](N)(C[S@]1(=O)=NCCC[C@]1(C)C#N)c1nc(Br)ccc1F]

The title compound was obtained as light yellow viscous oil in 83% yield according the general procedure III from (R)—N—((R)-2-(6-bromo-3-fluoropyridin-2-yl)-1-((1R,6R)-6-cyano-6-methyl-1-oxido-3,4,5,6-tetrahydro-1,2-thiazin-1-yl)propan-2-yl)-2-methylpropane-2-sulfinamide (or diastereomer). MS m/e: 389, 391 ([M+H]+).

Intermediate of Formula XXVIII-e (1S,6S)-14(S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer)

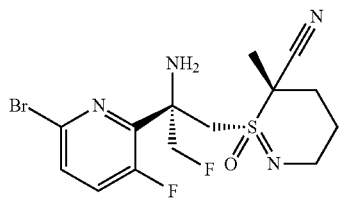 [SMILES: C[C@@]1(C#N)CCCN=[S@]1(=O)C[C@@](N)(CF)c1nc(Br)ccc1F]

The title compound was obtained as off-white solid in 83% yield according the general procedure III from (R)—N—((S)-2-(6-bromo-3-fluoropyridin-2-yl)-1-((1S,6S)-6-cyano-6-methyl-1-oxido-3,4,5,6-tetrahydro-1,2-thiazin-1-yl)-3-fluoropropan-2-yl)-2-methylpropane-2-sulfinamide (or diastereomer). MS m/e: 407, 409 ([M+H]+).

Intermediate of Formula XXVIII-f (1R,6R)-14(S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer)

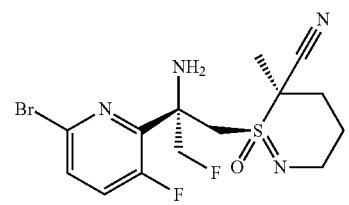 [SMILES: C[C@]1(C#N)CCCN=[S@@]1(=O)C[C@@](N)(CF)c1nc(Br)ccc1F]

The title compound was obtained as light yellow solid in 77% yield according the general procedure III from (R)—N—((S)-2-(6-bromo-3-fluoropyridin-2-yl)-1-((1R,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer). MS m/e: 407, 409 ([M+H]+).

Intermediate of Formula XXVIII-g (1R,6S)-14(S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer)

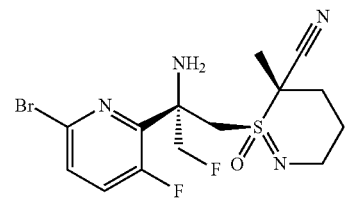 [SMILES: C[C@@]1(C#N)CCCN=[S@@]1(=O)C[C@@](N)(CF)c1nc(Br)ccc1F]

The title compound was obtained as light yellow solid in quantitative yield according the general procedure III from (R)—N—((S)-2-(6-bromo-3-fluoropyridin-2-yl)-1-((1R,6S)-6-cyano-6-methyl-1-oxido-3,4,5,6-tetrahydro-1,2-thiazin-1-yl)-3-fluoropropan-2-yl)-2-methylpropane-2-sulfinamide (or diastereomer). MS m/e: 407, 409 ([M+H]+).

Intermediate of Formula XXVIII-h (1S,6R)-14(S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer)

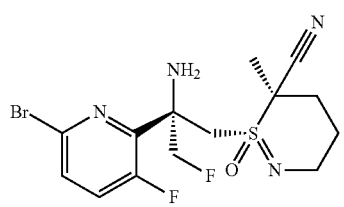 [SMILES: C[C@]1(C#N)CCCN=[S@]1(=O)C[C@@](N)(CF)c1nc(Br)ccc1F]

The title compound was obtained as light yellow viscous oil in quantitative yield according the general procedure III from (R)—N—((S)-2-(6-bromo-3-fluoropyridin-2-yl)-1-((1S,6R)-6-cyano-6-methyl-1-oxido-3,4,5,6-tetrahydro-1,2-thiazin-1-yl)-3-fluoropropan-2-yl)-2-methylpropane-2-sulfinamide (or diastereomer). MS m/e: 407, 409 ([M+H]+).

Intermediates of Formula XVII

General Procedure IV: Cyclization and N-BOC-protection

A mixture of an intermediate of formula XVIII in ethanol (0.1 M) and copper(I) bromide is heated at reflux for 6-24 h. The solvent is evaporated to give the crude intermediate of formula XXXIX. To a solution of an intermediate of formula XXXIX in tetrahydrofuran (0.1 M) and 1 M aqueous sodium bicarbonate solution (2 eq) is added di-tert-butyl dicarbonate (1 eq) and a catalytical amount of DMAP at RT. Stirring is continued for 2-24 h. The reaction mixture is partitioned between 1 M aqueous sodium bicarbonate solution and a solvent such as ethyl acetate. The layers are separated. The aqueous layer is extracted with one or two portions of an organic solvent such as ethyl acetate. The combined organic layers are dried over anhydrous sodium sulfate and concentrated to dryness. Purification by flash-chromatography gives an intermediate of formula XVII.

Intermediate of Formula XVII-a tert-butyl ((4aS,7R,9S)-7-(6-bromo-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer)

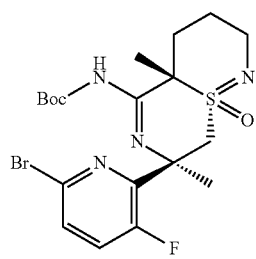 [SMILES: CC(C)(C)OC(=O)NC1=N[C@](C)(c2nc(Br)ccc2F)C[S@@]2(=O)=NCCC[C@@]12C]

The title compound was obtained as light yellow solid in 8% yield according the general procedure IV from (1S,6S)-1-((R)-2-amino-2-(6-bromo-3-fluoropyridin-2-yl)propyl)-6-methyl-3,4,5,6-tetrahydro-1,2-thiazine-6-carbonitrile 1-oxide (or diastereomer). MS m/e: 489, 491 ([M+H]+).

Intermediate of Formula XVII-b tert-butyl ((4aR,7R,9R)-7-(6-bromo-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer)

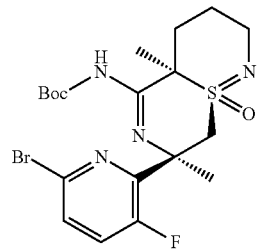 [SMILES: CC(C)(C)OC(=O)NC1=N[C@](C)(c2nc(Br)ccc2F)C[S@]2(=O)=NCCC[C@]12C]

The title compound was obtained as off-white solid in 30% yield according the general procedure IV from (1R,6R)-1-((R)-2-amino-2-(6-bromo-3-fluoropyridin-2-yl)propyl)-6-methyl-3,4,5,6-tetrahydro-1,2-thiazine-6-carbonitrile 1-oxide (or diastereomer). MS m/e: 489, 491 ([M+H]+).

Intermediate of Formula XVII-e tert-butyl ((4aS,7S,9S)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer)

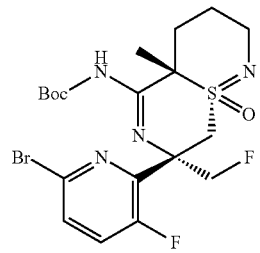 [SMILES: CC(C)(C)OC(=O)NC1=N[C@](CF)(c2nc(Br)ccc2F)C[S@@]2(=O)=NCCC[C@@]12C]

The title compound was obtained as light yellow solid in 24% yield according the general procedure IV from (1S,6S)-1-((S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer). MS m/e: 507, 509 ([M+H]+).

85

Intermediate of Formula XVII-f tert-butyl ((4aR,7S,9R)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer)

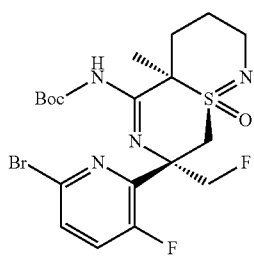 [SMILES: CC(C)(C)OC(=O)NC1=N[C@](CF)(c2nc(Br)ccc2F)C[S@]2(=O)=NCCC[C@]12C]

The title compound was obtained as light yellow solid in 25% yield according the general procedure IV from (1R,6R)-1-((S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer). MS m/e: 507, 509 ([M+H]$^+$).

Intermediate of Formula XVII-g tert-butyl ((4aS,7S,9R)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate

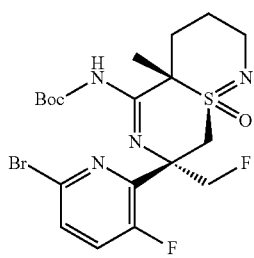 [SMILES: CC(C)(C)OC(=O)NC1=N[C@](CF)(c2nc(Br)ccc2F)C[S@]2(=O)=NCCC[C@@]12C]

The title compound was obtained as white solid in 13% yield according the general procedure IV from (1R,6S)-1-((S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer). MS m/e: 507, 509 ([M+H]$^+$).

86

Intermediate of Formula XVII-h tert-butyl ((4aR,7S,9S)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate

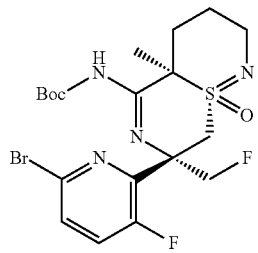 [SMILES: CC(C)(C)OC(=O)NC1=N[C@](CF)(c2nc(Br)ccc2F)C[S@@]2(=O)=NCCC[C@]12C]

The title compound was obtained as white solid in 6% yield according the general procedure IV from (1S,6R)-1-((S)-2-amino-2-(6-bromo-3-fluoropyridin-2-yl)-3-fluoropropyl)-6-methyl-3,4,5,6-tetrahydro-1,2-thiazine-6-carbonitrile 1-oxide (or diastereomer). MS m/e: 507, 509 ([M+H]$^+$).

Intermediates of Formula XVIII

General Procedure V: Amination of Bromopyridine

To a solution of a bromopyridine intermediate of formula XVII in a mixture of 1,4-dioxane/water (3:1, 0.1 M) are added sodium azide (10 eq), copper (I) iodide (0.56 eq), sodium ascorbate (0.28 eq) and trans-N,N'-dimethylcyclohexane-1,2-diamine (0.89 eq). The reaction mixture is heated at 70° C. and stirred for 2-6 h. The reaction mixture is partitioned between 1 M aqueous sodium hydroxide solution and a solvent such as ethyl acetate. The layers are separated. The aqueous layer is extracted with one or two portions of an organic solvent such as ethyl acetate. The combined organic layers are dried over anhydrous sodium sulfate and concentrated to dryness. Purification by flash-chromatography gives an intermediate of formula XVIII.

Intermediate of Formula XVIII-a tert-butyl ((4aS,7R,9S)-7-(6-amino-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer)

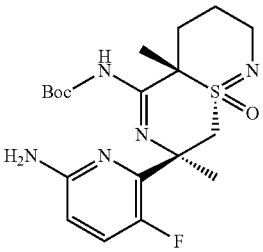 [SMILES: CC(C)(C)OC(=O)NC1=N[C@](C)(c2nc(N)ccc2F)C[S@@]2(=O)=NCCC[C@@]12C]

The title compound was obtained as light yellow solid in 31% yield according the general procedure V from tert-butyl ((4aS,7R,9S)-7-(6-bromo-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer). MS m/e: 426 ([M+H]+).

Intermediate of Formula XVIII-b tert-butyl ((4aR,7R,9R)-7-(6-amino-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer)

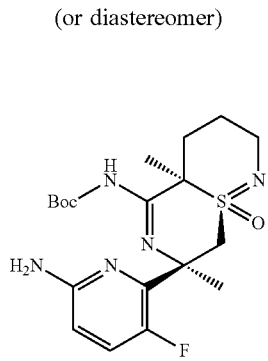

The title compound was obtained as light yellow solid in 55% yield according the general procedure V from tert-butyl ((4aR,7R,9R)-7-(6-bromo-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer). MS m/e: 426 ([M+H]+).

Intermediate of Formula XVIII-e tert-butyl ((4aS,7S,9S)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer)

The title compound was obtained as light yellow solid in 41% yield according the general procedure V from tert-butyl ((4aS,7S,9S)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer). MS m/e: 444 ([M+H]+).

Intermediate of Formula XVIII-f tert-butyl ((4aR,7S,9R)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer)

The title compound was obtained as light yellow solid in 53% yield according the general procedure V from tert-butyl ((4aR,7S,9R)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer). MS m/e: 444 ([M+H]+).

Intermediate of formula XVIII-g tert-butyl 44aS,7S,9R)-7-(6-amino-3-fluoropyridin-2-yl)-7-(fluoromethyl)-4a-methyl-9-oxido-2,3,4,4a,7,8-hexahydro-11,41thiazino[2,1-f][1,2]thiazin-5-yl)carbamate (or diastereomer)

The title compound was obtained as off-white solid in 75% yield according the general procedure V from tert-butyl ((4aS,7S,9R)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer). MS m/e: 444 ([M+H]+).

Intermediate of Formula XVIII-h tert-butyl 44aR,7S,9S)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer)

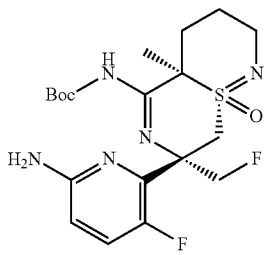 [SMILES: CC(C)(C)OC(=O)NC1=N[C@](CF)(c2nc(N)ccc2F)C[S@@]2(=O)=NCCC[C@]12C]

The title compound was obtained as off-white solid in 75% yield according the general procedure V from tert-butyl ((4aR,7S,9S)-7-(6-bromo-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer). MS m/e: 444 ([M+H]$^+$).

Intermediate of Formula XX 1-(6-Bromo-3-fluoro-2-pyridyl)ethanone

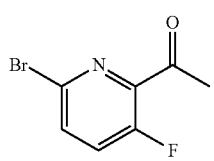

To a solution of 2-bromo-5-fluoropyridine (16.78 g, 95.3 mmol) in diethyl ether (348 ml) was slowly added butyllithium (1.6 M in hexane) (65.6 ml, 105 mmol) at −78° C. under argon atmosphere. The resulting yellow reaction mixture was stirred at −78° C. for two hours and n-methoxy-n-methylacetamide (10.8 g, 11.2 ml, 105 mmol) was added. The reaction mixture was stirred at −78° C. for another hour before quenching with 10 ml of a 4.0M aqueous solution of hydrochloric acid and the reaction was let to warm up to room temperature. The pH of the mixture was ajusted to 7 by addition of 2M aqueous solution of hydrochloric acid. The reaction mixture was washed with 50 ml of brine and the organic phase was collected. The aqueous layer was back-extracted twice with ethyl acetate. Combined organic phases were dried over sodium sulfate and concentrated in vacuo. The crude material was purified by flash chromatography (silica gel, 20 g, gradient 0% to 7% of ethyl acetate in heptane) to give the title compound (10.76 g, 51.8%) as light yellow oil. MS m/e: 220.0 ([M+H]$^+$).

Intermediate of Formula XXI (R,E)-N-[1-(6-Bromo-3-fluoro-2-pyridyl)ethylidene]-2-methyl-propane-2-sulfinamide

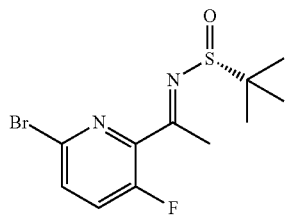 [SMILES: C/C(=N\[S@](=O)C(C)(C)C)c1nc(Br)ccc1F]

To a solution of 1-(6-bromo-3-fluoropyridin-2-yl)ethanone (int-XX, 1.76 g, 7.76 mmol) in dry tetrahydrofuran (15.5 ml) under an argon atmosphere at room temperature was added (R)-2-methylpropane-2-sulfinamide (959 mg, 7.76 mmol) and titanium(IV) ethoxide (3.54 g, 3.28 ml, 15.5 mmol). The reaction solution was then stirred at 50° C. for 48 hours. The reaction mixture was diluted with 20 ml of ethyl acetate and quenched by addition of 2 ml of water. After stirring for 10 minutes the formed slurry was filtered off through a pad of Celite®. The organic layer was dried over sodium sulfate and evaporated to give a crude yellow oil. The crude material was purified by flash chromatography on silica gel eluting with a gradient 0% to 10% of ethyl acetate in heptane to yield the title compound (2.143 g, 86.0%) as light yellow oil. MS m/e: 323.1 ([M+H]$^+$).

Intermediates of Formula XXII

2-Methylsulfinylpropanenitrile

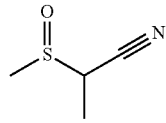

To a solution of 2-(methylthio)propanenitrile (int-III, 15 g, 141 mmol) in dichloromethane (400 ml) cooled at 0° C. was added m-CPBA (31.6 g, 141 mmol) by portions and the reaction mixture was stirred at 0° C. for two hours. The cold suspension was filtered through a pad of Celite° and the filter pad was washed with dichloromethane. The filtrate was extracted with 100 ml of a 2.0M aqueous solution of sodium carbonate (+ little bit of sodium thiosulfate). Organic phase was collected and the aqueous phase was back-extracted with dichloromethane. The combined organic phases were dried over sodium sulfate and evaporated down to dryness to give the title compound (15.8 g, 96%) that was used without any futher purification. MS m/e: 118.0 ([M+H]$^+$).

Intermediates of Formula XXIII

2-Methyl-2-methylsulfinyl-pent-4-enenitrile

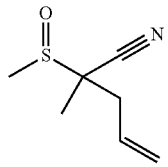

To a solution of 2-(methylsulfinyl)propanenitrile (int-XXII, 10 g, 85.3 mmol) in dry tetrahydrofuran (250 ml) cooled down to 0° C. under an argon atmosphere was added sodium hydride (3.93 g, 98.1 mmol) by portions and the reaction was stirred at 0° C. for 15 minutes and 45 minutes at room temperature. Addition of 3-bromoprop-1-ene (11.9 g, 8.49 ml, 98.1 mmol) to the reaction mixture which was then stirred at room temperature for 14 hours. The reaction was quenched by addition of water and the reaction mixture was diluted with ethyl acetate. The organic phase was extracted with water and was collected. The aqueous phase was back-extracted with ethyl acetate. The combined organic phases were dried over sodium sulfate and evaporated down to dryness to give the title compound (14.1 gr, 95%, purity: 90%) as a crude oil which was used without any further purification. MS m/e: 158.0 ([M+H]$^+$).

Intermediates of Formula XXIV

N-(2-Cyanopent-4-en-2-yl-methyl-oxo$\lambda^6$-sulfanylidene)-4-nitrobenzenesulfonamide

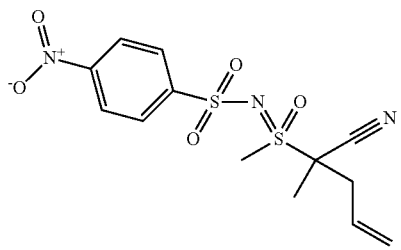

To a solution of 2-methyl-2-(methylsulfinyl)pent-4-enenitrile (int-XXIII, 7.8 g, 44.6 mmol) in acetonitrile (300 ml) was added 4-nitrobenzenesulfonamide (10.8 g, 53.6 mmol), iodobenzene diacetate (21.6 g, 67 mmol), 4,4',4"-tri-tert-butyl-2,2':6',2"-terpyridine (1.79 g, 4.46 mmol) and silver nitrate (758 mg, 4.46 mmol). The reaction was then stirred at 60° C. for 24 hours and the reaction was concentrated in vacuo and the residue was dissolved in ethyl acetate. The organic phase was extracted with a 1.0M aqueous solution of sodium hydrogenocarbonate and the organic phase was collected. The aqueous phase was back-extracted with ethyl acetate. The combined organic phases were dried over sodium sulfate and evaporated down to dryness. The crude material was purified by flash chromatography on silica gel eluting with dichloromethane to yield the title compound (9.51g, 59%) as light yellow solid. MS m/e: 358.1 ([M+H]$^+$).

Intermediates of Formula XXV

2-Methyl-2-(methylsulfonimidoyl)pent-4-enenitrile

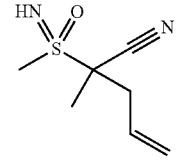

To a solution of N-(2-cyanopent-4-en-2-yl-methyl-oxo$\lambda^6$-sulfanylidene)-4-nitrobenzenesulfonamide (int-XXIV, 8.2 g, 22.9 mmol) in acetonitrile (190 ml) was added cesium carbonate (13.5 g, 41.3 mmol) followed by addition of thiophenol (4.04 g, 3.78 ml, 36.7 mmol). The reaction was then stirred at room temperature for 16 hours and the insolubles were removed by filtration over Celite®. The filter pad was washed with acetonitrile and the filtrate was concentrated in vacuo. The obtained residue was dissolved in ethyl acetate and extracted with brine. The organic phase was collected and the aqueous phase was back-extracted with ethyl acetate. The combined organic phases were dried over sodium sulfate and evaporated down to dryness. The crude material was purified by flash chromatography on silica gel eluting with a gradient of dichloromethane and methanol (0% to 4%) to give the title compound (3.21 g, 81%) as light yellow oil. MS m/e: 173.1 ([M+H]$^+$).

Intermediates of Formula XXVI 2-(N-Allyl-S-methylsulfonimidoyl)-2-methylpent-4-enenitrile

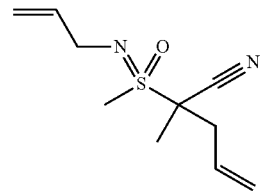

To a solution of 2-methyl-2-(S-methylsulfonimidoyl)pent-4-enenitrile (int-XXV, 3.2 g, 18.6 mmol) in dry dimethoxyethane (90 ml) cooled down to 0° C. under an argon atmosphere was added sodium hydride (892 mg, 22.3 mmol) and the reaction mixture was stirred at 0° C. for 20 minutes followed by 40 minutes at room temperature. To the reaction mixture was added 3-iodoprop-1-ene (3.74 g, 2.04 ml, 22.3 mmol) and the reaction was stirred at room temperature for 14 hours. The reaction was stopped by quenching it with water and was stirred for 5 minutes. The reaction was then diluted with ethyl acetate and extracted with a saturated aqueous solution of ammonium chloride. The organic phase was collected and the aqueous phase was back-extracted with ethyl acetate. The combined organic phases were dried over sodium sulfate and evaporated down to dryness. The crude material was purified by flash chromatography on silica gel eluting with a gradient of heptane and ethyl acetate to yield the title compound (2.85 g, 72%) as alight yellow oil. MS m/e: 213.2 ([M+H]$^+$).

Intermediates of Formula XXVII-A 1,7-Dimethyl-6,7-dihydro-3H-1,2-thiazepine-7-carbonitrile 1-oxide (racemate A)

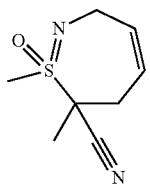

To a solution of 2-(N-allyl-S-methylsulfonimidoyl)-2-methylpent-4-enenitrile (int-XXVI, 2.83 g, 13.3 mmol) in dichloromethane (280 ml) under an argon atmosphere was added Grubbs second generation catalyst (905 mg, 1.07 mmol) and the reaction was then stirred at 50° C. for 14 hours. The reaction mixture was then concentrated in vacuo and the obtained crude residue was directly purified by flash chromatography on silica eluting with a mixture of heptane and ethyl acetate. The two racemic mixtures could be separated to give the title compound as the least polar racemic mixture (1.192 g, 48%). MS m/e: 185.1 ([M+H]⁺).

Intermediates of Formula XXVII-B 1,7-Dimethyl-6,7-dihydro-3H-1,2-thiazepine-7-carbonitrile 1-oxide (racemate B)

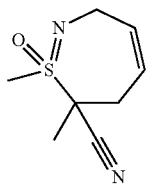

The title compound was synthesized in analogy to preparation of intermediate XXVII-A, using 2-(N-allyl-S-methylsulfonimidoyl)-2-methyl-pent-4-enenitrile (int-XXVI) as starting material, and isolated by chromatography as the more polar racemic mixture (720 mg, 29%); MS m/e: 185.1 ([M+H]+).

Intermediates of Formula XXVIII-A 1,7-Dimethyl-4,5,6,7-tetrahydro-3H-1,2-thiazepine-7-carbonitrile 1-oxide (racemate A)

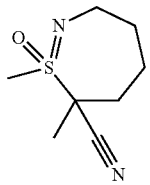

To a solution of 1,7-dimethyl-6,7-dihydro-3H-1,2-thiazepine-7-carbonitrile 1-oxide (racemate A) (int-XXVII-A, 1.19 g, 6.46 mmol) in ethanol (20 ml) under an argon atmosphere was added palladium on charcoal 10% (10% w/w) (119 mg, 1.12 mmol) .The atmosphere of the reaction vessel was then changed to hydrogen atmosphere and the reaction was stirred under a pressure of 2.5 bar of hydrogen for 8 hours. The reaction mixture was filtered through a pad of Celite® and the filter pad was washed with ethanol three times. The filtrate was concentrated in vacuo to a crude product which was purified by flash chromatography on silica eluting with a mixture of heptane and ethyl acetate to yield the title compound (92 1 mg, 77%) as light yellow oil.MS m/e: 187.1 ([M+H]⁺).

Intermediates of Formula XXVIII-B 1,7-Dimethyl-4,5,6,7-tetrahydro-3H-1,2-thiazepine-7-carbonitrile 1-oxide (racemate B)

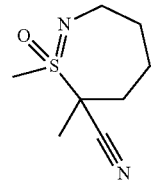

The title compound was synthesized in analogy to preparation of intermediate XXVIII-A, using 1,7-dimethyl-6,7-dihydro-3H-1,2-thiazepine-7-carbonitrile 1-oxide (racemate B) (int-XXVII-B) as starting material, and isolated (640 mg, 88%) as a light yellow oil; MS m/e: 187.1 ([M+H]+).

Intermediates of Formula XXIX-A (R)—N-(2-(6-Bromo-3-fluoropyridin-2-yl)-1-(7-cyano-7-methyl-1-oxido-4,5,6,7-tetrahydro-3H-1,2-thiazepin-1-yl)propan-2-yl)-2-methylpropane-2-sulfinamide (stereoisomer A)

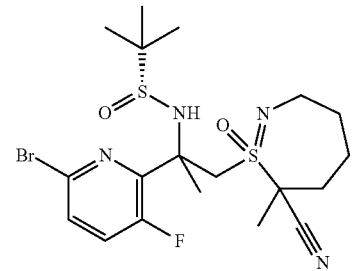 [SMILES: CC(CS1(=O)=NCCCCC1(C)C#N)(N[S@](=O)C(C)(C)C)c1nc(Br)ccc1F]

To a solution of 1,7-dimethyl-4,5,6,7-tetrahydro-3H-1,2-thiazepine-7-carbonitrile 1-oxide (racemate A) (int-XXVIII-A, 913 mg, 4.9 mmol) in dry tetrahydrofurane (12 ml) under an argon atmosphere was added at −70° C. n-butyllithium 1.6M solution in hexane (3.06 ml, 4.9 mmol).

The reaction mixture was stirred at −73° C. for 90 minutes. A solution of (R,E)-N-(1-(6-bromo-3-fluoropyridin-2-yl)ethylidene)-2-methylpropane-2-sulfinamide (intXXI, 1.05 g, 3.27 mmol, Eq: 1) in dry tetrahydrofurane (6 ml) was then added to the reaction mixture at −73° C. The stirring was continued for 3hours at −75° C. and then the reaction mixture was quenched with acetic acid (353 mg, 337 μl 5.88 mmol) at −70° C. The reaction was stirred at −70° C. for 10 minutes, then let to warm up to 0° C. and poured into a separatory funnel with ethyl acetate. The organic phase was extracted with an 2.0M aqueous solution of sodium carbonate and the organic phase was collected. The aqueous phase was back-extracted with ethyl acetate. The combined organic layers were dried over sodium sulfate and evaporated down to dryness to give a crude yellow oil as a mixture of stereoisomers. The crude material was purified by flash chromatography on silica eluting with a mixture of heptane and ethyl acetate to yield the title compound, which is the least polar stereoisomer, (1.19 g, purity: 65%, 47%) as a light yellow oil and contaminated with the sulfoximine reactant. The compound was used without any further purification. MS m/e: 509.2 ([M+H]$^+$).

Intermediates of Formula XXIX-B (R)—N-(2-(6-Bromo-3-fluoropyridin-2-yl)-1-(7-cyano-7-methyl-1-oxido-4,5,6,7-tetrahydro-3H-1,2-thiazep in-1-yl)propan-2-yl)-2-methylpropane-2-sulfinamide (stereoisomer B)

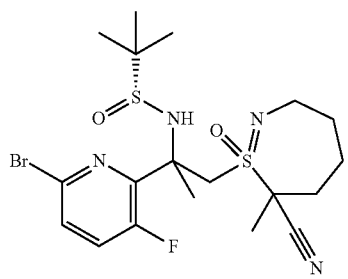 [SMILES: CC(CS1(=O)=NCCCCC1(C)C#N)(N[S@](=O)C(C)(C)C)c1nc(Br)ccc1F]

The title compound was synthesized in analogy to preparation of intermediate XXIX-A, using 1,7-dimethyl-4,5,6,7-tetrahydro-3H-1,2-thiazepine-7-carbonitrile 1-oxide (racemate A) (XXVIII-A) and (R,E)-N-(1-(6-bromo-3-fluoropyridin-2-yl)ethylidene)-2-methylpropane-2-sulfinamide (int-XXI) as starting materials, and was the more polar stereoisomer isolated by chromatography (535 mg, 29%) as a light yellow oil; MS m/e: 509.2 ([M+H]+).

Intermediates of Formula mix-XXIX (R)—N-(2-(6-Bromo-3-fluoropyridin-2-yl)-1-(7-cyano-7-methyl-1-oxido-4,5,6,7-tetrahydro-3H-1,2-thiazep in-1-yl)prop an-2-yl)-2-methylpropane-2-sulfinamide

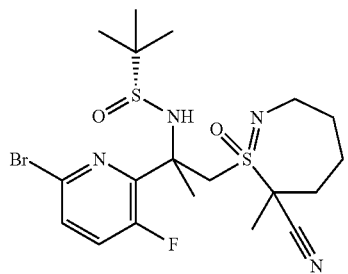 [SMILES: CC(CS1(=O)=NCCCCC1(C)C#N)(N[S@](=O)C(C)(C)C)c1nc(Br)ccc1F]

To a solution of 1,7-dimethyl-4,5,6,7-tetrahydro-3H-1,2-thiazepine-7-carbonitrile 1-oxide (racemate B) (int-XXVIII-B, 635 mg, 3.41 mmol) in dry tetrahydrofurane (10 ml) was added at −70° C. n-butlylithium 1.6M solution in hexane (2.13 ml, 3.41 mmol, Eq: 1.5). The reaction mixture was stirred at −73° C. for 90 minutes. A solution of (R,E)-N-(1-(6-bromo-3-fluoropyridin-2-yl)ethylidene)-2-methylpropane-2-sulfinamide (int-XXI, 730 mg, 2.27 mmol) in dry tetrahydrofurane (5 ml) at −73° C. was then added. The reaction mixture was stirred for 6 hours at −75° C. The reaction mixture was then quenched with acetic acid (246 mg, 234 μl, 4.09 mmol) at −70° C. and the mixture was stirred at −70° C. for 10 minutes. The reaction was let to warm up to 0° C. and poured into a separatory funnel containing ethyl acetate and a 2.0M aqueous solution of sodium carbonate. After the extraction the organic phase was collected and the aqueous phase was back-extracted with ethyl acetate. The combined organic layers were dried over sodium sulfate and evaporated to dryness. The crude material was purified by chromatography on silica eluting with a mixture of heptane and ethyl acetate to yield the title compound (1.08 g, 70%, purity : 75%) as a mixture of two major stereoisomers and contaminated with the sulfoximine reactant. The product was used for the next step without any further purification. MS m/e: 509.2 ([M+H]$^+$).

Intermediates of Formula XXX-A 1-(2-Amino-2-(6-bromo-3-fluoropyridin-2-yl)propyl)-7-methyl-4,5,6,7-tetrahydro-3H-1,2-thiazepine-7-carbonitrile 1-oxide (stereoisomer A)

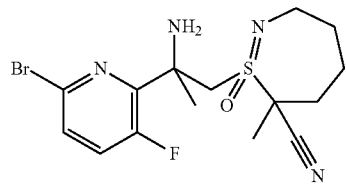 [SMILES: CC(N)(CS1(=O)=NCCCCC1(C)C#N)c1nc(Br)ccc1F]

To a solution of (R)—N-(2-(6-bromo-3-fluoropyridin-2-yl)-1-(7-cyano-7-methyl-1-oxido-4,5,6,7-tetrahydro-3 H-1,2-thiazepin-1-yl)propan-2-yl)-2-methylpropane-2-sulfinamide (stereoisomer A) (int-XXIX-A, 1.19 g, 1.52 mmol) in methanol (10 ml) was added a 4.0M solution of hydrochloric acid in dioxane (1.14 ml, 4.57 mmol). The reaction mixture was stirred at room temperature for one hour. The volatiles were removed in vacuo and the obtained residue was suspended in ethyl acetate. The organic phase was extracted with a 2.0M aqueous solution of sodium carbonate and the organic phase was collected. The aqueous phase was back-extracted with ethyl acetate. The combined organic phases were dried over sodium sulfate and evaporated down to dryness. The crude material was purified by flash chromatography on silica eluting with a mixture of heptane and ethyl acetate to yield the title compound (577 mg, 85%) as a light yellow oil. MS m/e: 405.1 ([M+H]$^+$).

Intermediates of Formula XXX-B 1-(2-Amino-2-(6-bromo-3-fluoropyridin-2-yl)propyl)-7-methyl-4,5,6,7-tetrahydro-3 H-1,2-thiazepine-7-carbonitrile 1-oxide (stereoisomer B)

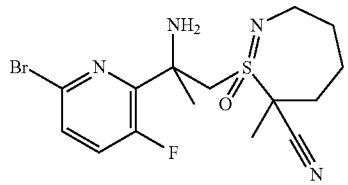 [SMILES: CC(N)(CS1(=O)=NCCCCC1(C)C#N)c1nc(Br)ccc1F]

The title compound was synthesized in analogy to preparation of intermediate XXX-A, using (R)—N-(2-(6-bromo-3-fluoropyridin-2-yl)-1-(7-cyano-7-methyl-1-oxido-4,5,6,7-tetrahydro-3H-1,2-thiazepin-1-yl)propan-2-yl)-2-methylpropane-2-sulfinamide (stereoisomer B) (XXIX-B) as starting material, and isolated (535 mg, 29%) as a light yellow oil; MS m/e: 403.1 ([M+H]+).

Intermediates of Formula XXX-C 1-(2-Amino-2-(6-bromo-3-fluoropyridin-2-yl)propyl)-7-methyl-4,5,6,7-tetrahydro-3H-1,2-thiazepine-7-carbonitrile 1-oxide (stereoisomer C)

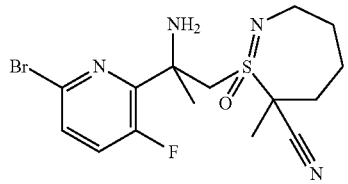 [SMILES: CC(N)(CS1(=O)=NCCCCC1(C)C#N)c1nc(Br)ccc1F]

The title compound was synthesized in analogy to preparation of intermediate XXX-A, using (R)—N-(2-(6-bromo-3-fluoropyridin-2-yl)-1-(7-cyano-7-methyl-1-oxido-4,5,6,7-tetrahydro-3 H-1,2-thiazepin-1-yl)propan-2-yl)-2-methylpropane-2-sulfinamide (int-mix-XXIX) as starting material. Single stereoisomers could be separated and the title compound was the less polar stereoisomer isolated by chromatography (402 mg, purity: ~30%, 14%) as a light yellow oil; MS m/e: 405.1 ([M+H]+).

Intermediates of Formula XXX-D 1-(2-Amino-2-(6-bromo-3-fluoropyridin-2-yl)propyl)-7-methyl-4,5,6,7-tetrahydro-3H-1,2-thiazepine-7-carbonitrile 1-oxide (stereoisomer D)

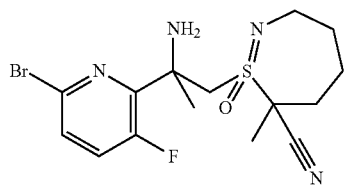 [SMILES: CC(N)(CS1(=O)=NCCCCC1(C)C#N)c1nc(Br)ccc1F]

The title compound was synthesized in analogy to preparation of intermediate XXX-A,using (R)—N-(2-(6-bromo-3-fluoropyridin-2-yl)-1-(7-cyano-7-methyl-1-oxido-4,5,6,7-tetrahydro-3H-1,2-thiazepin-1-yl)propan-2-yl)-2-methylpropane-2-sulfinamide (int-mix-XXIX) as starting material. Single stereoisomers could be separated and the title compound was the more polar stereoisomer isolated by chromatography (506 mg, 53%) as a light yellow oil; MS m/e: 405.1 ([M+H]+).

Intermediates of Formula XXXI-A

6-Amino-8-(6-bromo-3-fluoropyridin-2-yl)-5a,8-dimethyl-3,4,5,5a,8,9-hexahydro-2H-[1,4]thiazino[2,1-g][1,2]thiazepine 10-oxide (stereoisomer A)

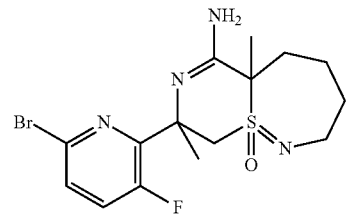 [SMILES: CC1(c2nc(Br)ccc2F)CS2(=O)=NCCCCC2(C)C(N)=N1]

To a solution of 1-(2-amino-2-(6-bromo-3-fluoropyridin-2-yl)propyl)-7-methyl-4,5,6,7-tetrahydro-3H-1,2-thiazepine-7-carbonitrile 1-oxide (stereoisomer A) (int-XXX-A, 555 mg, 1.24 mmol) in dry toluene (15 ml) cooled at 0° C. under an argon atmosphere was added trimethylaluminum 2.0M solution in heptane (681 μl, 1.36 mmol) and the reaction mixture was stirred at 0° C. for 5 minutes followed by 15 minutes at room temperature. The reaction mixture was then stirred at 60° C. for 1 hour. The reaction was quenched by careful addition of water and the reaction was vigorously stirred at room temperature for 25 minutes. A thick suspension formed which was removed by filtration over a pad of Celite®. The filter pad was washed three times with ethyl acetate. The filtrate was extracted with a 2.0M aqueous solution of sodium carbonate. The organic phase was collected and the aqueous phase was back-extracted with ethyl acetate. The combined organic phases were dried over sodium sulfate and evaporated down to dryness. The crude material was purified by flash chromatography on silica eluting with a mixture of dichloromethane and a 3% solution of NH3 in MeOH to yield the title compound (141 mg, 28%) as a light yellow oil. MS m/e: 405.1 ([M+H]+).

Intermediates of Formula XXXI-B

6-Amino-8-(6-bromo-3-fluoropyridin-2-yl)-5 a,8-dimethyl-3,4,5,5 a, 8,9-hexahydro-2H-[1,4]thiazino[2,1-g][1,2]thiazepine 10-oxide (stereoisomer B)

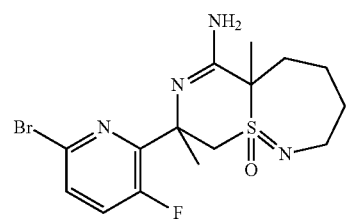 [SMILES: CC1(c2nc(Br)ccc2F)CS2(=O)=NCCCCC2(C)C(N)=N1]

The title compound was synthesized in analogy to preparation of intermediate XXXI-A, 1-(2-amino-2-(6-bromo-3-fluoropyridin-2-yl)propyl)-7-methyl-4,5,6,7-tetrahydro-3H-1,2-thiazepine-7-carbonitrile 1-oxide (stereoisomer B) (int-XXX-B) as starting material and isolated (152 mg, 46%) as a light yellow oil; MS m/e: 405.1 ([M+H]+).

Intermediates of Formula XXXI-D

6-Amino-8-(6-bromo-3-fluoropyridin-2-yl)-5a,8-dimethyl-3,4,5,5a,8,9-hexahydro-2H-[1,4]thiazino[2,1-g][1,2]thiazepine 10-oxide (stereoisomer D)

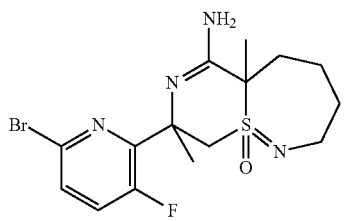 [SMILES: CC1(c2nc(Br)ccc2F)CS2(=O)=NCCCCC2(C)C(N)=N1]

The title compound was synthesized in analogy to preparation of intermediate XXXI-A, using 1-(2-amino-2-(6-bromo-3-fluoropyridin-2-yl)propyl)-7-methyl-4,5,6,7-tetrahydro-3H-1,2-thiazepine-7-carbonitrile1-oxide (stereoisomer D) (int-XXX-D) as starting material and isolated (154 mg, 31%) as a light yellow oil; MS m/e: 405.1 ([M+H]+).

Intermediates of Formula X,XXIII-A tert-Butyl (8-(6-amino-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer A)

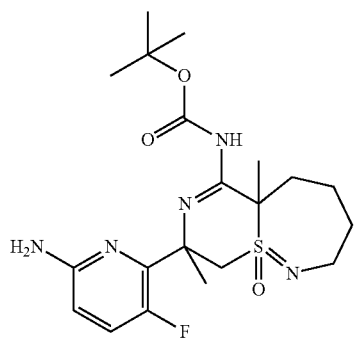 [SMILES: CC(C)(C)OC(=O)NC1=NC(C)(c2nc(N)ccc2F)CS2(=O)=NCCCCC12C]

To a solution of 6-amino-8-(6-bromo-3-fluoropyridin-2-yl)-5a,8-dimethyl-3,4,5,5a,8,9-hexahydro-2H-[1,4]thiazino[2,1-g][1,2]thiazepine 10-oxide (stereoisomer A) (int-XXXI-A, 141 mg, 350 µmol) in dichloromethane (2.5 ml) was added triethylamine (46 mg, 63.3 µl, 454 µmol,) and di-tert-butyl dicarbonate (83.9 mg, 89.3 µl, 385 µmol). The reaction was then stirred at room temperature for one hour. The reaction was then diluted with dichloromethane and extracted with a 2.0M aqueous solution of sodium carbonate. The organic phase was collected and the aqueous phase was back-extracted with dichloromethane. The combined organic phase were dried over sodium sulfate and evaporated down to dryness to give 164 mg of the crude intermediate XXXII-A as a light yellow oil, which was used without any further purification. To a solution of crude intermediate XXXII-A (164 mg) in a mixture of dioxane (2.5 ml)/water (0.5 ml) was added sodium azide (68.2 mg, 1.05 mmol) copper (I) iodide (26.6 mg, 140 µmol), trans-n,n'-dimethylcyclohexane-1,2-diamine (19.9 mg, 140 µmol) and sodium ascorbate (55.4 mg, 280 µmol) . The reaction mixture was stirred at 70° C. for one hour and the reaction was cooled down to room temperature followed by diluted with ethyl acetate. The organic phase was extracted with a 2.0M aqueous solution of sodium carbonate and the organic phase was collected. The aqueous phase was back-extracted with ethyl acetate. The combined organic phases were dried over sodium sulfate and evaporated down to dryness. The crude material was purified by flash chromatography on silica eluting with a mixture of heptane and ethyl acetate to yield the title compound (55 mg, 36%) as an off-white solid. MS m/e: 440.3 ([M+H]$^+$).

Intermediates of Formula XXXIII-B tert-Butyl (8-(6-amino-3-fluoropyridin-2-yl)-5 a,8-dimethyl-10-oxido-3,4,5,5 a,8,9-hexahydro-2H-[1,4]thiazino[2,1-g][1,2]thiazepin-6-yl)carbamate (stereoisomer B)

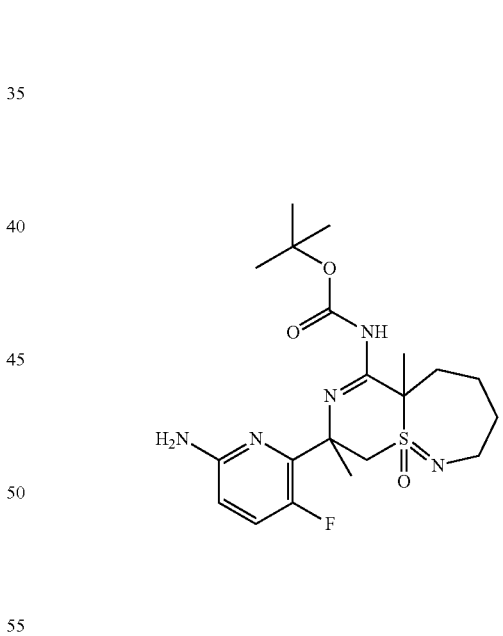

The title compound was synthesized in analogy to preparation of intermediate XXXIII-A, using 6-amino-8-(6-bromo-3-fluoropyridin-2-yl)-5a,8-dimethyl-3,4,5,5a,8,9-hexahydro-2H-[1,4]thiazino[2,1-g][1,2]thiazepine 10-oxide (stereoisomer B) (int-XXXI-B) as starting material and isolated (87 mg, 66%) as an off-white solid; MS m/e: 440.3 ([M+H]$^+$).

101

Intermediates of Formula X,XXIII-D tert-Butyl (8-(6-amino-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer D)

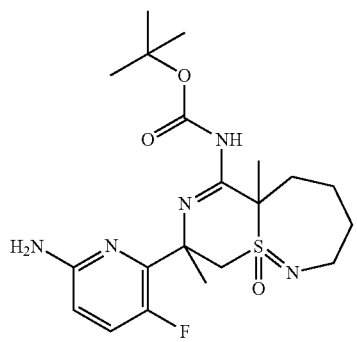 [SMILES: CC(C)(C)OC(=O)NC1=NC(C)(c2nc(N)ccc2F)CS2(=O)=NCCCCC12C]

The title compound was synthesized in analogy to preparation of intermediate XXXIII-A, using 6-amino-8-(6-bromo-3-fluoropyridin-2-yl)-5 a, 8-dimethyl-3,4,5,5 a,8,9-hexahydro-2H-[1,4]thiazino[2,1-g][1,2]thiazepine 10-oxide (stereoisomer D) (int-XXXI-D) as starting material and isolated (91 mg, 55%) as an off-white powder; MS m/e: 440.3 ([M+H]$^+$).

EXAMPLES

General Procedure VI: Amide Coupling and N-BOC Deprotection

To a solution of an acid derivative of formula XVI (1.3 eq) in dichloromethane (0.1 M) is added 1-chloro-N,N,2-trimethyl-1-propenylamine (1.3 eq) at RT. The reaction mixture is stirred for 30 minutes. A solution of an aminopyridine intermediate of formula XVIII (1 eq) and an organic base such as triethylamine or Hunig's Base (1 eq) is added to the acid chloride solution at 0-5° C. Stirring is continued for 1 h. The reaction mixture is partitioned between 1 M aqueous sodium carbonate solution and a solvent such as ethyl acetate or dichloromethane. The layers are separated. The aqueous layer is extracted with one or two portions of an organic solvent such as ethyl acetate or dichloromethane. The combined organic layers are dried over anhydrous sodium sulfate, filtrated and concentrated to dryness. Purification by flash-chromatography gives an intermediate of formula XIX. To a solution of the an intermediate of formula XIX in dichloromethane (0.1 M) is added trifluoroacetic acid (20 eq) at RT. Stirring is continued for 1-6 h. The reaction mixture is concentrated to dryness. The residue is partitioned between 1 M aqueous sodium bicarbonate solution and a solvent such as ethyl acetate or dichloromethane. The layers are separated. The aqueous layer is extracted with one or two portions of an organic solvent such as ethyl acetate or dichloromethane. The combined organic layers are dried over anhydrous sodium sulfate, filtrated and concentrated to dryness to give the title compound of formula I.

102

Example 1

N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-cyano-3-methylpyridine-2-carboxamide that is N-{6-1(4aS,7R)-5-Amino-4a,7-dimethyl-9-oxido-2,3,4,4a,7,8-hexahydro-9$\lambda^4$-[1,4]thiazino[2,1-f][1,2]thiazin-7-yl]-5-fluoropyridin-2-yl1-5-cyano-3-methylpyridine-2-carboxamide or N-{6-1(4aR,7R)-5-amino-4a,7-dimethyl-9-oxido-2,3,4,4a,7,8-hexahydro-9$\lambda^4$-[1,4]thiazino[2,1-f][1,2]thiazin-7-yl}-5-fluoropyridin-2-yl}-5-cyano-3-methylpyridine-2-carboxamide The title compound was obtained as off-white solid (0.023 g, 52%) with an ee of 100% from tert-butyl ((4aS,7R,9S)-7-(6-amino-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer) and 5-cyano-3-methylpicolinic acid. MS m/e: 470 ([M+H]$^+$).

Example 2

N-[6-(6-amino-5a,8-dimethyl-10-oxido-3,4,5,5a,8,9-hexahydro-2H-1M$^4$-[1,4]thiazino[2,1-g][1,2]thiazepin-8-yl)-5-fluoropyridin-2-yl]-5-cyano-3-methylpyridine-2-carboxamide (stereoisomer A)

a) tert-Butyl (8-(6-(5-cyano-3-methylpicolinamido)-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer A)

To a suspension of 5-cyano-3-methylpicolinic acid (26.4 mg, 0.163 mmol) in dry dichloromethane (1 ml) under an argon atmosphere was added 1-chloro-n,n,2-trimethylpropenylamine (21.7 mg, 0.163 mmol) and the reaction mixture was stirred at room temperature for 30 minutes followed by addition of a solution of tert-butyl (8-(6-amino-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer A) (int-XXXIII-A, 55 mg, 125 µmol) and triethylamine (19 mg, 0.026 ml, 0.188 mmol) in dichloromethane. The reaction was stirred at room temperature for one hour. The reaction was diluted with dichloromethane and extracted with a 2.0M aqueous solution of sodium carbonate. The organic phase was collected and the aqueous phase was back-extracted with dichloromethane. The combined organic phases were dried over sodium sulfate and evaporated down to dryness. The crude material was purified by flash chromatography on silica eluting with a mixture of heptane and ethyl acetate to yield the title compound (75 mg , 88%) as a white solid. MS m/e: 584.3 ([M+H]$^+$).

b) N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-5-cyano-3-methylpyridine-2-carboxamide (stereoisomer A)

To a solution of tert-butyl (8-(6-(5-cyano-3-methylpicolinamido)-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer A) (example 2a, 75 mg, 0.128 mmol) in dry dichloromethane (1 ml) cooled down to 0° C. under an argon atmosphere was added 1,3-dimethoxybenzene (35.5 mg, 0.034 ml, 0.257 mmol) and trimethylsilyl trifluoromethanesulfonate (85.7 mg, 0.070 ml, 0.385 mmol). The reaction was then stirred at 0° C. for 2 hours. The reaction was diluted with dichloromethane and the mixture was poured into a separatory funnel and the organic phase was extracted with a 2.0M aqueous solution of sodium carbonate. The organic phase was collected and the aqueous phase was back-extracted with dichloromethane. The combined organic phase were dried over sodium sulfate and evaporated down to dryness. The crude material was purified by preparative HPLC to yield the title compound (34 mg, 55%) as a white powder. MS m/e: 484.3 ($[M+H]^+$).

Example 3

N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl]-5-fluoropyridin-2-yl]-5-cyano-3-methylpyridine-2-carboxamide (stereoisomer B)

a) tert-Butyl (8-(6-(5-cyano-3-methylpicolinamido)-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer B)

The title compound was synthesized in analogy to Example 2a, using tert-butyl (8-(6-amino-3-fluoropyridin-2-yl)-5a,8-dimethyl-10-oxido-3,4,5,5 a,8,9-hexahydro-2H-[1,4]thiazino[2,1-g][1,2]thiazepin-6-yl)carbamate (stereoisomer B) (int-XXXIII-B) as starting material and isolated (53 mg, 78%) as a white powder; MS m/e: 584.3 ($[M+H]^+$).

b) N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-5-cyano-3-methylpyridine-2-carboxamide (stereoisomer B)

The title compound was synthesized in analogy to Example 2b, using tert-butyl (8-(6-(5-cyano-3-methylpicolinamido)-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer B) as starting material and isolated (28 mg, 64%) as a white powder; MS m/e: 484.3 ($[M+H]^+$).

Example 4

N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-5-cyano-3-methylpyridine-2-carboxamide (stereoisomer D)

a) tert-Butyl (8-(6-(5-cyano-3-methylpicolinamido)-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer D)

The title compound was synthesized in analogy to Example 2a, using tert-butyl (8-(6-amino-3-fluoropyridin-2-yl)-5a,8-dimethyl-10-oxido-3,4,5,5a,8,9-hexahydro-2H-[1,4]thiazino[2,1-g][1,2]thiazepin-6-yl)carbamate (stereoisomer D) (int-XXXIII-D) as starting material and isolated (37 mg, 62%) as a white powder; MS m/e: 584.3 ($[M+H]^+$).

b) N-[6-(6-amino-5a,8-dimethyl-10-oxido-3,4,5,5a,8,9-hexahydro-2H-10$\lambda^4$-[1,4]thiazino[2,1-g][1,2]thiazepin-8-yl)-5-fluoropyridin-2-yl]-5-cyano-3-methylpyridine-2-carboxamide (stereoisomer D)

The title compound was synthesized in analogy to Example 2b, using tert-butyl (8-(6-(5-cyano-3-methylpicolinamido)-3-fluoropyridin-2-yl)-5 a,8-dimethyl-10-oxido-3,4,5,5a,8,9-hexahydro-2H-[1,4]thiazino[2,1-g][1,2]thiazepin-6-yl)carbamate (stereoisomer D) as starting material and isolated (15 mg, 53%) as a white powder; MS m/e: 484.3 ($[M+H]^+$).

Example 5

N-{6-1(4aS,7S)-5-Amino-7-(fluoromethyl)-4a-methyl-9-oxido-2,3,4,4a,7,8-hexahydro-9$\lambda^4$-[1,4]thiazino[2,1-f][1,2] thiazin-7-yl]-5-fluoropyridin-2-yl}-5-cyano-3-methylpyridine-2-carboxamide or N-{6-1(4aS,7S)-5-amino-7-(fluoromethyl)-4a-methyl-9-oxido-2,3,4,4a,7,8-hexahydro-9$\lambda^4$-[1,4]thiazino[2,1-f][1,2] thiazin-7-yl]-5-fluoropyridin-2-yl}-5-cyano-3-methylpyridine-2-carboxamide

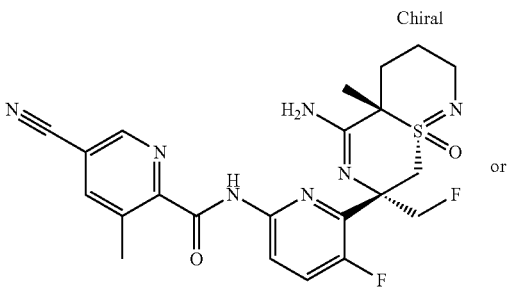

or

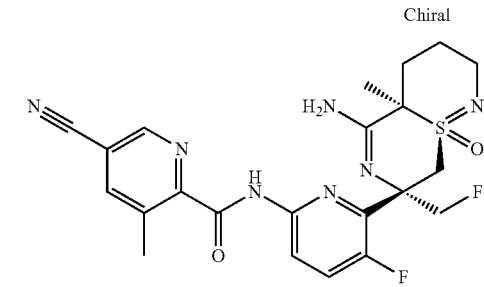

The title compound was obtained as light yellow solid in 74% with an ee purity of 81% from tert-butyl ((4aS,7S,9S)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer) and 5-cyano-3-methylpicolinic acid. MS m/e: 488 ($[M+H]^+$).

Example 6

N-{6-1(4aR,7S)-5-Amino-7-(fluoromethyl)-4a-methyl-9-oxido-2,3,4,4a,7,8-hexahydro-9$\lambda^4$-[1,4]thiazino[2,1-f][1,2] thiazin-7-yl]-5-fluoropyridin-2-yl}-5-cyano-3-methylpyridine-2-carboxamide or N-{6-1(4aS,7S)-5-Amino-7-(fluoromethyl)-4a-methyl-9-oxido-2,3,4,4a,7,8-hexahydro9$\lambda^4$-[1,4]thiazino[2,1-f][1,2]thiazin-7-yl]-5-fluoropyridin-2-yl}-5-cyano-3-methylpyridine-2-carboxamide

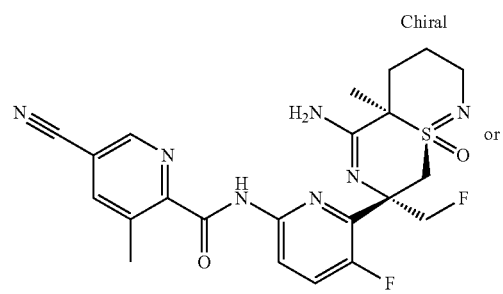

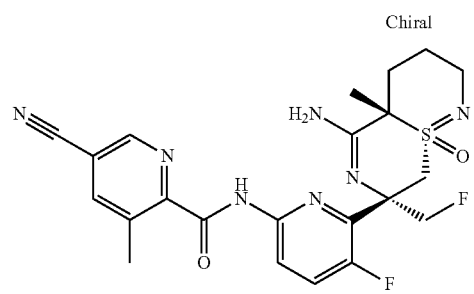

The title compound was obtained as light yellow solid in 64% with an ee purity of 100% from tert-butyl ((4aR,7S,9R)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer) and 5-cyano-3-methylpicolinic acid. MS m/e: 488 ([M+H]$^+$).

Example 7

N-{6-1(4aR,7S)-5-amino-7-(fluoromethyl)-4a-methyl-9-oxido-2,3,4,4a,7,8-hexahydro-9$\lambda^4$-[1,4]thiazino[2,1-f][1,2]thiazin-7-yl]-5-(2,2,3,3-tetrafluoropropoxy)pyridine-2-carboxamide or N-{6-1(4aS,7S)-5-amino-7-(fluoromethyl)-4a-methyl-9-oxido-2,3,4,4a,7,8-hexahydro-9$\lambda^4$-[1,4]thiazino[2,1-f][1,2]thiazin-7-yl]-5-(2,2,3,3-tetrafluoropropoxy)pyridine-2-carboxamide

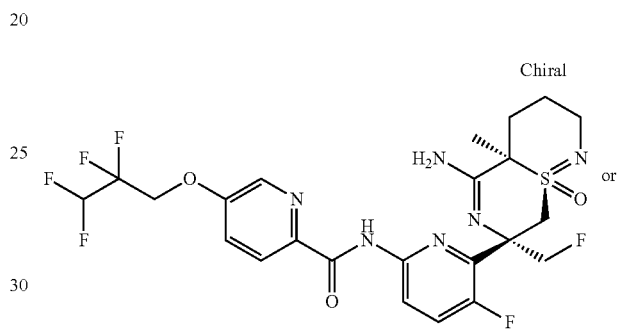

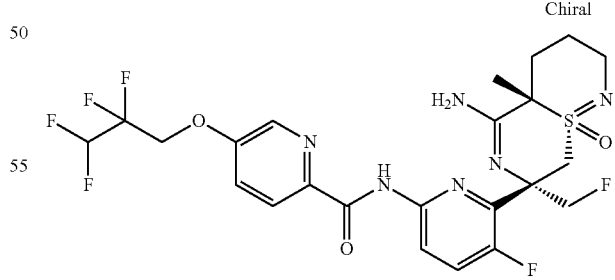

The title compound was obtained as off-white solid in 69% from tert-butyl ((4aR,7S,9R)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer) and 5-(2,2,3,3-tetrafluoropropoxy)picolinic acid. MS m/e: 579 ([M+H]$^+$).

Example 8

N-{6-1(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl}-5-fluoropyridin-2-yl}-5-cyano-3-methylpyridine-2-carboxamide or N-{6-1(4aR,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl}-5-fluoropyridin-2-yl}-5-cyano-3-methylpyridine-2-carboxamide

Example 9

N-{6-1(4aR,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl}-5-fluoropyridin-2-yl}-5-cyano-3-methylpyridine-2-carboxamide or N-{6-1(4aS,7S)-5-amino-7-(fluoromethyl)-4a-methyl-9-oxido-2,3,4,4a,7,8-hexahydro-9λ⁴-[1,4]thiazino[2,1-f][1,2]thiazin-7-yl}-5-fluoropyridin-2-yl}-5-cyano-3-methylpyridine-2-carboxamide

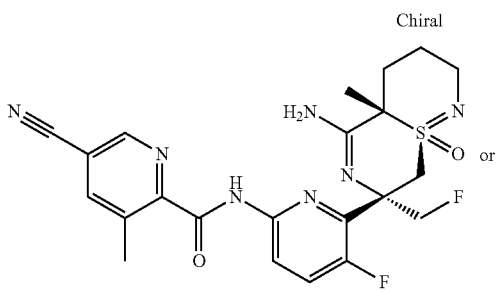

or

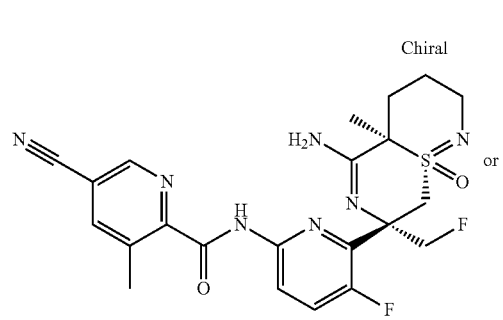

or

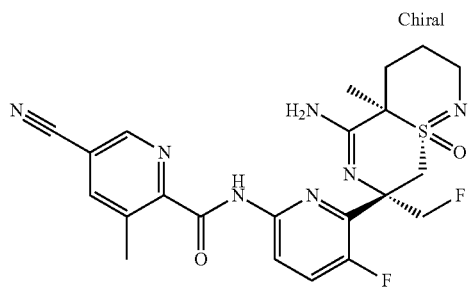

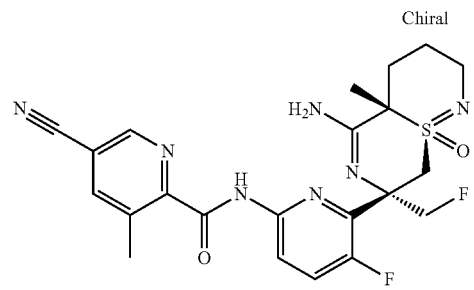

The title compound was obtained as off-white solid in 77% with an ee-purity of 100% from tert-butyl ((4aS,7S,9R)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer) and 5-cyano-3-methylpicolinic acid. MS m/e: 488 ([M+H]⁺).

The title compound was obtained as off-white solid in 65% with an ee-purity of 100% from tert-butyl ((4aR, 7S, 9S)-7-(6-amino-3-fluoropyridin-2-yl)-7-(fluoromethyl)-4a-methyl-9-oxido-2,3,4,4a,7,8-hexahydro-[1,4]thiazino[2,1-f][1,2]thiazin-5-yl)carbamate (or diastereomer) and 5-cyano-3-methylpicolinic acid. MS m/e: 488 ([M+H]⁺).

Example 10

N-{6-1(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-cyano-3-methylpyridine-2-carboxamide or N-{6-1(4aS,7R)-5-Amino-4a,7-dimethyl-9-oxido-2,3,4,4a,7,8-hexahydro-9λ⁴-[1,4]thiazino12,1-f][1,2]thiazin-7-yl]-5-fluoropyridin-2-yl}-5-cyano-3-methylpyridine-2-carboxamide

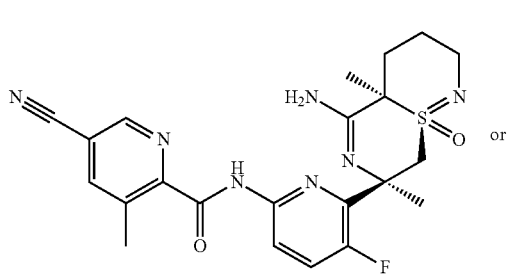

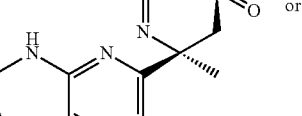

The title compound was obtained as off-white solid in 54% with from tert-butyl ((4aR,7R,9R)-7-(6-amino-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer) and 5-cyano-3-methylpicolinic acid. MS m/e: 470 ([M+H]⁺).

Example 11

N-{6-1(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-3-chloro-5-cyanopyridine-2-carboxamide or N-{6-1(4aS,7R)-5-amino-4a,7-dimethyl-9-oxido-2,3,4a,7,8-hexahydro-9λ⁴-[1,4]thiazino[2,1-f][1,2]thiazin-7-yl]-5-fluoropyridin-2-yl}-3-chloro-5-cyanopyridine-2-carboxamide

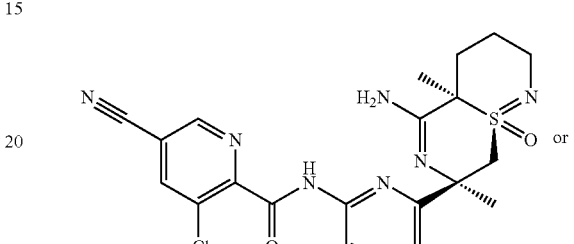

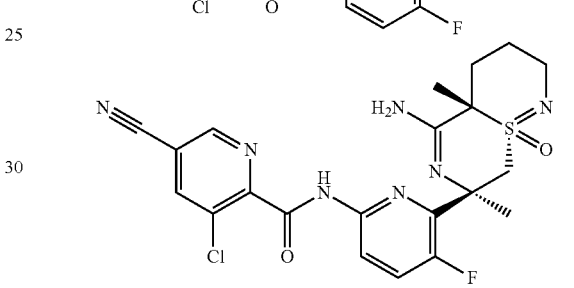

The title compound was obtained as light brown solid in 62% with from tert-butyl ((4aR,7R,9R)-7-(6-amino-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer) and 3-chloro-5-cyanopicolinic acid. MS m/e: 490 ([M+H]⁺).

Example 12

N-{6-1(4aR,7R)-5-amino-4a,7-dimethyl-9-oxido-2,3,4,4a,7,8-hexahydro-9λ⁴-[1,4]thiazino[2,1-f][1,2]thiazin-7-yl]-5-fluoropyridin-2-yl}-5-(2,2,3,3-tetrafluoropropoxy)pyridine-2-carboxamide or N-{6-1(4aS,7R)-5-amino-4a,7-dimethyl-9-oxido-2,3,4a,7,8-hexahydro-9λ⁴-[1,4]thiazino[2,1-f][1,2]thiazin-7-yl]-5-fluoropyridin-2-yl}-5-(2,2,3,3-tetrafluoropropoxy)pyridine-2-carboxamide

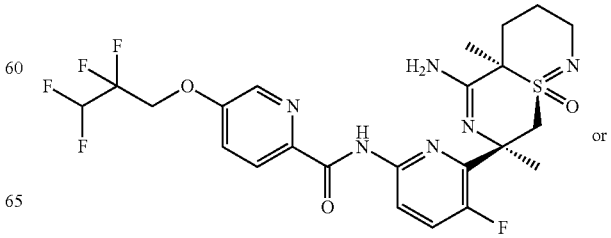

-continued

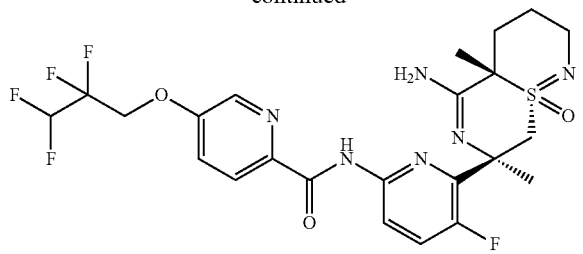

The title compound was obtained as white solid in 61% with from tert-butyl ((4aR,7R,9R)-7-(6-amino-3-fluoropyridin-2-yl)-4a,7-dimethyl-9-oxido-2,3,4,4a,7,8-hexahydro-[1,4]thiazino[2,1-f][1,2]thiazin-5-yl)carbamate (or diastereomer) and 5-(2,2,3,3-tetrafluoropropoxy)picolinic acid. MS m/e: 561 ([M+H$^+$).

Examples 13-25 can be prepared analogously.

The invention claimed is:

1. A compound of formula I:

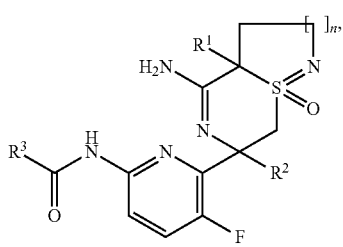

wherein:
n is 2 or 3;
$R^1$ is selected from the group consisting of
  i) H,
  ii) halogen,
  iii) $C_{1-6}$-alkyl, and
  iv) halogen-$C_{1-6}$-alkyl;
$R^2$ is selected from the group consisting of
  i) H,
  ii) halogen,
  iii) $C_{1-6}$-alkyl, and
  iv) halogen-$C_{1-6}$-alkyl;
$R^3$ is selected from the group consisting of
  i) aryl,
  ii) aryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
  iii) heteroaryl, and
  iv) heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy;
or a pharmaceutically acceptable salt thereof.

2. The compound according to claim 1, wherein $R^1$ is $C_{1-6}$-alkyl.

3. The compound according to claim 1, wherein $R^1$ is methyl.

4. The compound according to claim 1, wherein $R^2$ is $C_{1-6}$-alkyl or halogen-$C_{1-6}$-alkyl.

5. The compound according to claim 1, where $R^2$ is methyl or —$CH_2F$.

6. The compound according to claim 1, wherein $R^3$ is heteroaryl substituted by 1-4 substituents individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxy, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy.

7. The compound according to claim 1, wherein $R^3$ is heteroaryl substituted by cyan and $C_{1-6}$-alkyl.

8. The compound according to claim 1, wherein $R^3$ pyridinyl substituted by cyano and methyl.

9. The compound according to claim 1, which is of formula Ia, wherein n, $R^1$ and $R^2$ are as described in claim 1 and $R^4$ is individually selected from amino, cyano, halogen, halogen-$C_{1-6}$-alkyl, halogen-$C_{1-6}$-alkoxy, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl, $C_{1-6}$-alkyl, $C_{3-6}$-cycloalkyl, $C_{3-6}$-cycloalkyl that is optionally substituted by 1 to 4 substituents individually selected from the group consisting of halogen, cyano, $C_{1-6}$-alkyl and $C_{1-6}$-alkoxyl, $C_{3-6}$-cycloalkyl-$C_{1-6}$-alkoxy and $C_{3-6}$-cycloalkyl-$C_{1-6}$-alkoxy, wherein the cycloalkyl unit is substituted by 1 to 4 substituents individually selected from the group consisting of halogen, cyano, $C_{1-6}$-alkyl and $C_{1-6}$-alkoxy

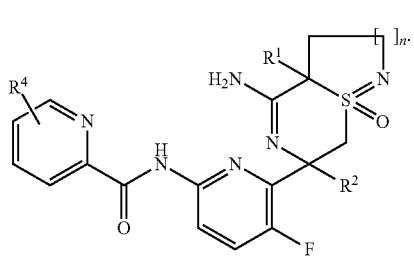

or a pharmaceutically acceptable salt thereof.

10. The compound according to claim 1, selected from the group consisting of:
N-[6-(5-amino-4a,7-dimethyl-9-oxido-2,3,4,4a,7,8-hexahydro-9$\lambda^4$-[1,4]thiazino[2,1-f][1,2]thiazin-7-yl)-5-fluoropyridin-2-yl]-5-methoxypyrazine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-3,5-dichloropyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-fluoro-3-methylpyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-(difluoromethoxy)pyridine-2-carboxamide, N-[6-(5-amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-(2,2-difluoroethoxy)pyridine-2-carboxamide, N-[6-(5amino-4a,7-dimethyl-9-oxido-2,3,4,4a,7,8-hexahydro-9λ$^4$-[1,4]thiazino[2,1-f][1,2]thiazin-7-yl)-5-fluoropyridin-2-yl]-5-(2,2,3,3-tetrafluoropropoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-cyano-3-methylpyridine-2-carboxamide (stereoisomer A), N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-cyano-3-methylpyridine-2-carboxamide (stereoisomer B), N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-cyano-3-methylpyridine-2-carboxamide (stereoisomer D), N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-methoxypyrazine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-3,5-dichloropyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-fluoro-3-methylpyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-3-chloro-5-cyanopyridine-2-carboxamide N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-(difluoromethoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-(2,2-difluoroethoxy)pyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-(2,2,3,3-tetrafluoropropoxy)pyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide N-{6-[(4aS,7R)-5-Amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-3-chloro-5-cyanopyridine-2-carboxmide, N-{6-[(4aS,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-3-chloro-5-cyanopyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-2,2,3,3-tetrafluoropropoxy)pyridine-2carboxamide, N-{6-[(4aS,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-Amino-7-(fluoromethyl)-4a-methyl-9-oxido-2,3,4,4a,7,8-hexahydro-9λ$^4$-[1,4]thiazino[2,1-f][1,2thiazin-7-yl]-5-fluoropyridin-2-yl}{-5-cyano-3-methylpyridine-2-carboxamide, N-{6-[(4aS,7S)-5-Amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aR,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aS,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7R)-5-Amino-4a,7-dimethyl-9-oxido-2,3,4,4a7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-Amino-7-(fluoromethyl)-4a-methyl-9-oxido-2,3,4,4a,7,8- hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-amino-7-(fluoromethyl)-4a-methyl-9-oxido-2,3,4,4a,7,8-hexahydro-9λ$^4$-[1,4]thiazino[2,1-f][1,2thiazin-7-yl]-5-fluoropyridin-2-yl}-5-cyano-3-methylpyridine-2-carboxamide, N-{6-[(4aS,7S)-5-amino-7-(fluoromethyl)4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, and N-{6-[(4aR,7S)-5-amino-7-(fluoromethyl)-4a-methyl-9-oxido-2,3,4,4a,7,8-hexahydro-9λ$^4$-[1,4]thiazino[2,1-f]

[1,2]thiazin-7-yl]-5-fluoropyridin-2-yl}-5-cyano-3-methylpyridine-2-carboxamide, or a pharmaceutically acceptable salt thereof.

11. The compound according to claim 1, selected from the group consisting of:

N-{6-[(4aS,7R)-5-Amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-cyano-3-methylpyridine-2-carboxamide (stereoisomer A), N-[6-(6-amino-5a,8-dimethyl-10-oxido-3,4,5,5a,8,9-hexahydro-2H-10λ$^4$-[1,4]thiazino[2,1-g][1,2]thiazepin-8-yl)-5-fluoropyridin-2-yl]-5-cyano-3-methylpyridine-2-carboxamide (stereoisomer B), N-[6-(6-amino-5a,8-dimethyl-10-oxide-3,4,5,5a,8,9-hexahydro-2H-10λ$^4$-[1,4]thiazino[2,1-g][1,2]thiazepin-8-yl)-5-fluoropyridin-2-yl]-5-cyano-3-methylpyridine-2-carboxamide (stereoisomer D), N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide N-{6-[(4aS,7R)-5-Amino-4a,7-dimethyl-9-oxide-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-3-chloro-5-cyanopyridine-2-carboxamide, N-{6-[(4aS,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-3-chloro-5-cyanopyridine-2-carboxamide, N-{6-[(4aR,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aS,7R)-5-amino-4a,7-dimethyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{[6-[(4aR,7S)-5-Amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{[6-[(4aS,7S)-5-Amino-7-(fluoromethyl)-4a-methyl-9-oxido-2,3,4,4a,7,8-hexahydro-9λ$^4$-[1,4]thiazino[2,1-f][1,29 thiazin-7-yl]-5-fluoropyridin-2-yl}-5-cyano-3-methylpyridine-2-carboxamide, N-{[6-[(4aR,7S)-5-amino-7-(fluoromethyl)-4a-methyl-9-oxido-2,3,4,4a,7,8-hexahydro-9λ$^4$-[1,4]thiazino[2,1-][1,2]thiazin-7-yl]-5-fluoropyridin-2-yl}5-(2,2,3,3-tetrafluoropropoxy)pyridine-2-carboxamide, N-{6-[(4aS,7S)-5-amino-7-(fluorormethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-(2,2,3,3-tetrafluoropropoxy)pyridine-2-carboxamide, N-{6-[(4aR,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-Amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-amino-7-(fluoromethyl)-4a-methyl-9-oxide-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, N-{6-[(4aS,7S)-5-amino-7-(fluoromethyl)-4a-methyl-9-oxide-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, and N-{6-[(4aR,7S)-5-amino-7-(fluoromethyl)-4a-methyl-9-oxido-2,3,4,4a,7,8-hexahydro-9λ$^4$-[1,4]thiazino[2,1-f][1,2]thiazin-7-yl]-5-fluoropyridin-2-yl}-5-cyano-3-methylpyridine-2-carboxamide, or a pharmaceutically acceptable salt thereof.

12. A method of treating diseases and disorders characterized by elevated β-amyloid levels and/or β-amyloid oligomers and/or β-amyloid plaques and further deposits or Alzheimer's disease, comprising step of administering a therapeutically effective amount of a compound according to claim 1, or a pharmaceutically acceptable salt thereof, to a patient in need thereof.

13. A pharmaceutical composition, comprising a therapeutically effective amount of a compound according to claim 1, or a pharmaceutically acceptable salt thereof, and an excipient.

* * * * *